(12) United States Patent
Kim

(10) Patent No.: US 10,995,363 B2
(45) Date of Patent: *May 4, 2021

(54) NUCLEOTIDE ANALOGS

(71) Applicant: ABBOTT MOLECULAR INC., Des Plaines, IL (US)

(72) Inventor: Dae Hyun Kim, Northbrook, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,865

(22) Filed: Jan. 27, 2020

(65) Prior Publication Data

US 2020/0157606 A1 May 21, 2020

Related U.S. Application Data

(63) Continuation of application No. 15/944,553, filed on Apr. 3, 2018, now Pat. No. 10,577,646, which is a continuation of application No. 14/463,412, filed on Aug. 19, 2014, now Pat. No. 9,932,623.

(60) Provisional application No. 61/867,202, filed on Aug. 19, 2013.

(51) Int. Cl.
| | | |
|---|---|---|
| C12Q 1/68 | (2018.01) | |
| C07H 19/10 | (2006.01) | |
| C07H 19/20 | (2006.01) | |
| C12Q 1/6806 | (2018.01) | |
| C12N 15/10 | (2006.01) | |
| C07H 21/04 | (2006.01) | |
| C12Q 1/6869 | (2018.01) | |

(52) U.S. Cl.
CPC .......... *C12Q 1/6806* (2013.01); *C07H 19/10* (2013.01); *C07H 19/20* (2013.01); *C07H 21/04* (2013.01); *C12N 15/1065* (2013.01); *C12N 15/1093* (2013.01); *C12Q 1/6869* (2013.01)

(58) Field of Classification Search
CPC ...... C12Q 1/6806; C07H 19/10; C07H 19/20; C07H 21/04
See application file for complete search history.

(56) References Cited

U.S. PATENT DOCUMENTS

| | | | |
|---|---|---|---|
| 3,927,193 A | 12/1975 | Hansen et al. | |
| 4,036,945 A | 7/1977 | Haber | |
| 4,331,647 A | 5/1982 | Goldenberg | |
| 4,348,376 A | 9/1982 | Goldenberg | |
| 4,361,544 A | 11/1982 | Goldenberg | |
| 4,444,744 A | 4/1984 | Goldenberg | |
| 4,460,459 A | 7/1984 | Shaw et al. | |
| 4,460,561 A | 7/1984 | Goldenberg | |
| 4,468,457 A | 8/1984 | Goldenberg et al. | |
| 4,624,846 A | 11/1986 | Goldenberg | |
| 4,735,210 A | 4/1988 | Goldenberg | |
| 4,818,709 A | 4/1989 | Primus et al. | |
| 4,889,818 A | 12/1989 | Gelfand et al. | |
| 5,374,553 A | 12/1994 | Gelfand et al. | |
| 5,420,029 A | 5/1995 | Gelfand et al. | |
| 5,455,170 A | 10/1995 | Abramson et al. | |
| 5,466,591 A | 11/1995 | Abramson et al. | |
| 5,558,991 A | 9/1996 | Trainor | |
| 5,604,097 A | 2/1997 | Brenner | |
| 5,618,711 A | 4/1997 | Gelfand et al. | |
| 5,624,833 A | 4/1997 | Gelfand et al. | |
| 5,636,400 A | 6/1997 | Young | |
| 5,674,738 A | 10/1997 | Abramson et al. | |
| 5,695,934 A | 12/1997 | Brenner | |
| 5,744,305 A | 4/1998 | Fodor et al. | |
| 5,744,595 A | 4/1998 | Srivastava et al. | |
| 5,789,224 A | 8/1998 | Gelfand et al. | |
| 5,795,762 A | 8/1998 | Abramson et al. | |
| 5,846,719 A | 12/1998 | Brenner et al. | |
| 5,863,722 A | 1/1999 | Brenner | |
| 5,939,292 A | 8/1999 | Gelfand et al. | |
| 6,138,077 A | 10/2000 | Brenner | |
| 6,150,516 A | 11/2000 | Brenner et al. | |
| 6,172,214 B1 | 1/2001 | Brenner | |
| 6,172,218 B1 | 1/2001 | Brenner | |
| 6,235,475 B1 | 5/2001 | Brenner et al. | |
| 6,329,178 B1 | 12/2001 | Patel et al. | |
| 6,352,828 B1 | 3/2002 | Brenner | |
| 6,395,524 B2 | 5/2002 | Loeb et al. | |
| 6,602,695 B2 | 8/2003 | Patel et al. | |
| RE39,793 E | 8/2007 | Brenner | |
| 7,393,665 B2 | 7/2008 | Brenner | |
| 7,537,897 B2 | 5/2009 | Brenner et al. | |

(Continued)

FOREIGN PATENT DOCUMENTS

| | | |
|---|---|---|
| EP | 0517262 | 12/1992 |
| EP | 2535423 | 12/2012 |

(Continued)

OTHER PUBLICATIONS

Allawi H.T., et al., "Thermodynamics and NMR of Internal G.T. Mismatches in DNA," Biochemistry, 1997, vol. 36 (34), pp. 10581-10594.

Anderson M.L.M., "Quantitative Filter Hybridization" in: Nucleic Acid Hybridization, Hames B.D., ed., IRL Press, 1985, pp. 73-111.

Ausubel F.M., et al., "Current Protocols in Molecular Biology," 1996, vol. 1, pp. 1-14.

Auzzas L., et al., "Targeting Alphavbeta3 Integrin: Design and Applications of Mono-and Multifunctional RGD-Based Peptides and Semipeptides," Current Medicinal Chemistry, 2010, vol. 17 (13), pp. 1255-1299.

(Continued)

*Primary Examiner* — Jezia Riley
(74) *Attorney, Agent, or Firm* — Casimir Jones, S.C.; Kirk Hogan

(57) ABSTRACT

Provided herein is technology relating to the manipulation and detection of nucleic acids, including but not limited to compositions, methods, and kits related to nucleotides comprising a chemically reactive linking moiety.

20 Claims, 30 Drawing Sheets

Specification includes a Sequence Listing.

(56) References Cited

U.S. PATENT DOCUMENTS

| | | | |
|---|---|---|---|
| 7,544,473 | B2 | 6/2009 | Brenner |
| 7,935,822 | B2 | 5/2011 | Arden-Jacob et al. |
| 9,932,623 | B2 | 4/2018 | Kim |
| 10,036,013 | B2 * | 7/2018 | Kim .................. C12N 15/1086 |
| 2002/0012970 | A1 | 1/2002 | Smith et al. |
| 2003/0003486 | A1 | 1/2003 | Sauer et al. |
| 2004/0005599 | A1 | 1/2004 | Schoenbrunner et al. |
| 2005/0037398 | A1 | 2/2005 | Gelfand et al. |
| 2005/0090732 | A1 | 4/2005 | Ivkov et al. |
| 2006/0179585 | A1 | 8/2006 | Zilles et al. |
| 2007/0048748 | A1 | 3/2007 | Williams et al. |
| 2008/0038559 | A1 | 2/2008 | True |
| 2008/0050731 | A1 * | 2/2008 | Agnew ................ C12Q 1/6806 435/6.1 |
| 2009/0149340 | A1 | 6/2009 | True |
| 2011/0039259 | A1 | 2/2011 | Ju et al. |
| 2011/0045489 | A1 | 2/2011 | Gardner et al. |
| 2011/0172420 | A1 | 7/2011 | Zilles et al. |
| 2011/0190486 | A1 | 8/2011 | Zilles et al. |
| 2011/0223677 | A1 | 9/2011 | Arden-Jacob et al. |
| 2011/0270533 | A1 | 11/2011 | Zhang et al. |
| 2013/0046084 | A1 | 2/2013 | Brown et al. |
| 2013/0130919 | A1 | 5/2013 | Chen et al. |
| 2015/0051113 | A1 | 2/2015 | Kim |
| 2018/0320219 | A1 | 11/2018 | Kim |

FOREIGN PATENT DOCUMENTS

| | | |
|---|---|---|
| RU | 2337141 | 10/2008 |
| WO | WO 2015026845 | 2/2015 |

OTHER PUBLICATIONS

Barnes W.M., et al., "DNA Sequencing by Partial Ribosubstitution," Journal of Molecular Biology, 1978, vol. 119 (1), pp. 83-99.

Beer A.J., et al., "Pet Imaging of Integrin Avβ3 Expression," Theranostics, 2011, vol. 1, pp. 48-57.

Beer A.J., et al., "Pet Imaging of Avβ3 Expression in Cancer Patients," Methods in Molecular Biology (Clifton, N.J.), 2011, Vol, 680, pp. 183-200.

Bentley D.R., et al., "Accurate Whole Human Genome Sequencing Using Reversible Terminator Chemistry," Nature, 2008, vol. 456 (7218), pp. 53-59.

Daniels T.R., et al., "The Transferrin Receptor Part I: Biology and Targeting with Cytotoxic Antibodies for the Treatment of Cancer," Clinical Immunology (Orlando, Fla.), 2006, vol. 121 (2), pp. 144-158.

Efimov V.A., et al., "Synthesis of Polyacrylamides N-Substituted with Pna-Like Oligonucleotide Mimics for Molecular Diagnostic Applications," Nucleic Acids Research, 1999, vol. 27 (22), pp. 4416-4426.

El-Sagheer A.H., et al., "Biocompatible Artificial DNA Linker that is Read through by DNA Polymerases and is Functional in *Escherichia coli*," Proceedings of the National Academy of Sciences of the United States of America, 2011, vol. 108 (28), pp. 11338-11343.

Gardner A.F., et al., "Acyclic and Dideoxy Terminator Preferences Denote Divergent Sugar Recognition by Archaeon and Taq DNA Polymerases," Nucleic Acids Research, 2002, vol. 30 (2), pp. 605-613.

Gardner A.F., et al., "Determinants of Nucleotide Sugar Recognition in an Archaeon DNA Polymerase," Nucleic Acids Research, 1999, vol. 27 (12), pp. 2545-2553.

Gennaro A.R., Eds., Remington's Pharmaceutical Sciences, 1985, 17th edition, Mack Publishing Co, Table of contents.

Gennaro A.R., Eds., Remington's Pharmaceutical Sciences, 1990, 18 th edition, Mack Publishing Co.

Haff L.A., et al., "Single-Nucleotide Polymorphism Identification Assays Using a Thermostable DNA Polymerase and Delayed Extraction Maldi-Tof Mass Spectrometry," Genome Research, 1997, vol. 7 (4), pp. 378-388.

Haugland R.P., "The Handbook: A Guide to Fluorescent Probes and Labeling Technologies," in: Molecular Probes, 10th Edition, Spence M.T.Z., ed., Invitrogen Detection Technologies, United States of America, 2005, Table of Contents.

Huisgen R., et al., "Centenary Lecture—1,3-Dipolar Cycloadditions," Proceedings of the Chemical Society of London, 1961, pp. 357-396.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Kolb H.C., et al., "Click Chemistry: Diverse Chemical Function from a Few Good Reactions," Angewandte Chemie (International Ed. in English), 2001, vol. 40 (11), pp. 2004-2021.

Lochmann D., et al., "Drug Delivery of Oligonucleotides by Peptides," European Journal of Pharmaceutics and Biopharmaceutics : Official Journal of Arbeitsgemeinschaft Fur Pharmazeutische Verfahrenstechnik E.V, 2004, vol. 58 (2), pp. 237-251.

Morrison M., et al., "Integrin Imaging to Evaluate Treatment Response," Theranostics, 2011, vol. 1, pp. 149-153.

Nam H.Y., et al., "Primary Cardiomyocyte-Targeted Bioreducible Polymer for Efficient Gene Delivery to the Myocardium," Biomaterials, 2010, vol. 31 (31), pp. 8081-8087.

Paunesku T., et al., "Gadolinium-Conjugated Tio2-DNA Oligonucleotide Nanoconjugates Show Prolonged Intracellular Retention Period and T1-Weighted Contrast Enhancement in Magnetic Resonance Images," Nanomedicine : Nanotechnology, Biology, and Medicine, 2008, vol. 4 (3), pp. 201-207.

Qian Z.M., et al., "Targeted Drug Delivery via the Transferrin Receptor-Mediated Endocytosis Pathway," Pharmacological Reviews, 2002, vol. 54 (4), pp. 561-587.

Ruparel H., et al., "Design and Synthesis of a 3'-o-allyl Photocleavable Fluorescent Nucleotide as a Reversible Terminator for Dna Sequencing by Synthesis," Proceedings of the National Academy of Sciences of the United States of America, 2005, vol. 102 (17), pp. 5932-5937.

Sambrook J., et al., Molecular Cloning: A Laboratory Manual, 2nd Edition, Cold Spring Harbor Laboratory Press, Cold Spring Harbor, 1989.

Sanger F., et al., "DNA Sequencing with Chain-Terminating Inhibitors," Proceedings of the National Academy of Sciences, 1977, vol. 74 (12), pp. 5463-5467.

Sawhney H.S., et al., "Hubell in Macromolecules," Macromolecules, 1993, vol. 26 (4), pp. 581-587.

Southworth M.W., et al., "Cloning of Thermostable DNA Polymerases from Hyperthermophilic Marine Archaea with Emphasis on *Thermococcus* sp. 9 Degrees N-7 and Mutations Affecting 3'-5' Exonuclease Activity," Proceedings of the National Academy of Sciences of the United States of America, 1996, vol. 93 (11), pp. 5281-5285.

Sudimack J., et al., "Targeted Drug Delivery via the Folate Receptor," Advanced Drug Delivery Reviews, 2000, vol. 41 (2), pp. 147-162.

Zhou Y., et al., "Radiolabeled Cyclic Rgd Peptides as Radiotracers for Imaging Tumors and Thrombosis by Spect," Theranostics, 2011, vol. 1, pp. 58-82.

International Search Report and Written Opinion for Application No. PCT/US2014/051726, dated Mar. 10, 2015, 10 pages.

Meldal M., et al., "Cu-Catalyzed Azide-Alkyne Cycloaddition," Chemical Reviews, 2008, vol. 108 (8), pp. 2952-3015.

Andre Dallmann et al: 11 Structure and Dynamics of Triazole-Linked DNA: Biocompatibility Explained . . . Chemistry—A European Journal., val. 17, No. 52, Nov. 30, 2011 (Nov. 30, 2011), pp. 14714-14717.

Hassan Said et al: "Two-Step Synthesis of 1-7 a 5'-Azidothymidine Building Block for the Assembly of Oligonucleotides for Triazole-Forming Ligations", SYNLETT, vol. 23, No. 20, Nov. 16, 2012 (Nov. 16, 2012), pp. 2923-2926.

Pareek Chandra Shekhar et al: 11 Sequencing technologies and genome sequencing, Journal of Applied Genetics., vol. 52, No. 4, Nov. 1, 2011 (Nov. 1, 2011), pp. 413-435.

Extended European Search report of corresponding European application No. 14837595.9 dated Jan. 17, 2017.

(56) References Cited

OTHER PUBLICATIONS

El-Sagheer A.H., et al., "New strategy for the synthesis of chemically modified RNA constructs exemplified by hairpin and hammerhead ribozymes" PNAS, 2010, v.107. No. 35, pp. 15329-15334.
El-Sagheer A.H., et al.,"Synthesis and polymerase chain reaction amplification of DNA strands containing an unnatural triazole linkage", J. Am. Chem. Soc., 2009, v.131 No. 11, pp. 3958-3964.
Gardner, et al., "Rapid incorporation kinetics and improved fidelity of a novel class of 3'-OH unblocked reversible terminators", Nucleic Acids Research, 2012, v.40, No. 15, pp. 7404-7415.
Office Action issued in corresponding Russian Application No. 2016107198, dated Sep. 1, 2018, 9 pages.
Lu, Wen-Sheng, Biochemistry, Southest University Press, 2006, pp. 176-178.
Office Action issued in corresponding Chinese Application No. 201480057284.6, dated Jun. 29, 2018, 9 pages.

* cited by examiner

NUCLEOTIDE ANALOGS

This Application is a continuation of U.S. patent application Ser. No. 15/944,553, filed Apr. 3, 2018, which is a continuation of U.S. application Ser. No. 14/463,412 filed Aug. 19, 2014, now U.S. Pat. No. 9,932,623, issued Apr. 3, 2018, which claims priority to U.S. provisional patent application Ser. No. 61/867,202, filed Aug. 19, 2013, each of which are herein incorporated by reference in their entirety.

FIELD OF INVENTION

Provided herein is technology relating to the manipulation and detection of nucleic acids, including but not limited to compositions, methods, and kits related to nucleotides comprising a chemically reactive linking moiety.

BACKGROUND

Nucleic acid detection methodologies continue to serve as a critical tool in the field of molecular diagnostics. The ability to manipulate biomolecules specifically and efficiently provides the basis for many successful detection technologies. For example, linking a chemical, biological, or physical moiety (e.g., adding a "tag") to a biomolecule of interest is one key technology related to the subsequent manipulation, detection, and/or identification of the biomolecule.

Conventional linking technologies often rely on enzyme-assisted methods. For example, some methods to append a desired tag onto a target DNA use a ligase enzyme to join the target DNA to the tag (e.g., another DNA fragment comprising the tag, another DNA fragment to serve as the tag itself, etc.). In another method, a polymerase enzyme incorporates a tag-modified substrate of the polymerase (e.g., a dNTP or a modified-dNTP) into a nucleic acid. An advantage of these enzyme-assisted methods is that the links joining the biomolecule to the moiety are "natural" linkages that allow further manipulation of the conjugated product. However, some important drawbacks include low product yields, inefficient reactions, and low specificity due to multiple reactive groups present on a target biomolecule that the enzyme can recognize. In addition, conventional methods have high costs in both time and money.

SUMMARY

Accordingly, provided herein is technology related to linking moieties to biomolecules using chemical conjugation. These linkage reactions are more specific and efficient that conventional technologies because the reactions are designed to include a mechanism of conjugation between specific chemical moieties.

While most conventional chemical covalent linkages are not recognized and/or processed by biological catalysts (e.g., enzymes), thus limiting subsequent manipulation of the conjugated product, the technology described herein provides a chemical linkage that allows downstream manipulation of the conjugated product by standard molecular biological and biochemical techniques.

For example, while there are many nucleotide analogs currently available that can terminate a polymerase reaction (e.g., dideoxynucleotides and various 3' modified nucleotide analogs), these molecules inhibit or severely limit further manipulation of nucleic acids terminated by these analogs. For example, subsequent enzymatic reactions such as the polymerase chain reaction are completely or substantially inhibited by the nucleotide analogs. In addition, some solutions have utilized nucleotide analogs called "reversible terminators" in which the 3' hydroxyl groups are capped with a chemical moiety that can be removed with a specific chemical reaction, thus regenerating a free 3' hydroxyl. Use of these nucleotide analogs, however, requires the additional deprotection (uncapping) step to remove the protecting (capping) moiety from the nucleic acid as well as an additional purification step to remove the released protecting (capping) moiety from the reaction mixture.

In contrast to conventional technologies, provided herein is technology related to the design, synthesis, and use of nucleotide (e.g., ribonucleotide, deoxyribonucleotide) analogs that comprise chemically reactive groups. For example, some embodiments provide a nucleotide analog comprising an alkyne group, e.g., a nucleotide comprising a 3' alkyne group such as provided in embodiments of the technology related to a 3'-O-propargyl deoxynucleotides. The chemical groups and linkages do not impair or significantly limit the use of subsequent molecular biological techniques to manipulate compounds (e.g., nucleic acids, conjugates, and other biomolecules) comprising the nucleotide analogs. As such, the compounds (e.g., nucleic acids, conjugates, and other biomolecules) comprising the described nucleotide analogs are useful for many applications.

In some embodiments, nucleotide analogs find use as functional nucleotide terminators, that is, the nucleotide analogs terminate synthesis of a nucleic acid by a polymerase and additionally comprise a functional reactive group for subsequent chemical and/or biochemical processing, reaction, and/or manipulation. In particular, some embodiments provide a nucleotide analog in which the 3' hydroxyl group is capped by a chemical moiety comprising, e.g., an alkyne (e.g., a carbon-carbon triple bond, e.g., C≡C). When the 3' alkyne nucleotide analog is incorporated into a nucleic acid by a polymerase (e.g., a DNA and/or RNA polymerase) during synthesis, further elongation of the nucleic acid is halted ("terminated") because the nucleic acid does not have a free 3' hydroxyl to provide the proper substrate for subsequent nucleotide addition.

While the nucleotide analogs are not a natural substrate for conventional molecular biological enzymes, the alkyne chemical moiety is a well-known chemical conjugation partner reactive with particular functional moieties. For example, an alkyne reacts with an azide group (e.g., N₃, e.g., N=N=N) in a copper (I)-catalyzed azide-alkyne cycloaddition ("CuAAC") reaction to form two new covalent bonds between azide nitrogens and alkyl carbons. The covalent bonds form a chemical link (e.g., comprising a five-membered triazole ring) between a first component and a second component that comprised the azide and the alkyne moieties before linkage. This type of cycloaddition reaction is one of the foundational reactions of "click chemistry" because it provides a desirable chemical yield, is physiologically stable, and exhibits a large thermodynamic driving force that favors a "spring-loaded" reaction that yields a single product (e.g., a 1,4-regioisomer of 1,2,3-triazole). See, e.g., Huisgen (1961) "Centenary Lecture-1,3-Dipolar Cycloadditions", *Proceedings of the Chemical Society of London* 357; Kolb, Finn, Sharpless (2001) "Click Chemistry: Diverse Chemical Function from a Few Good Reactions", *Angewandte Chemie International Edition* 40(11): 2004-2021. For example:

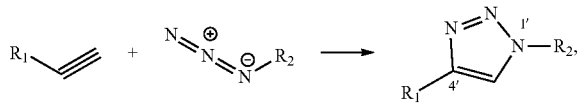

where $R_1$ and $R_2$ are individually any chemical structure or chemical moiety.

The reaction can be performed in a variety of solvents, including aqueous mixtures, compositions comprising water and/or aqueous mixtures, and a variety of organic solvents including compositions comprising alcohols, dimethyl sulfoxide (DMSO), dimethylformamide (DMF), tert-butyl alcohol (TBA or tBuOH; also known as 2-methyl-2-propanol (2M2P)), and acetone. In some embodiments, the reaction is performed in a milieu comprising a copper-based catalyst such as Cu/Cu(OAc)$_2$, a tertiary amine such as tris-(benzyltriazolylmethyl)amine (TBTA), and/or tetrahydrofuran and acetonitrile (THF/MeCN).

In some embodiments, the triazole ring linkage has a structure according to:

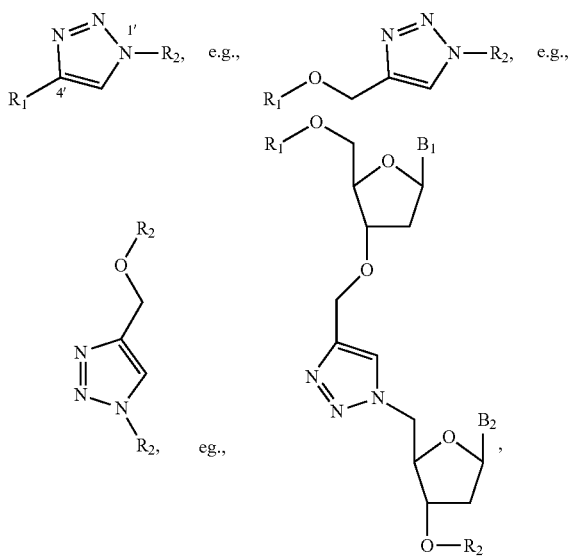

where $R_1$ and $R_2$ are individually any chemical structure or chemical moiety (and may be the same or different chemical structures or chemical moieties in different structures) and B, $B_1$, and $B_2$ individually indicate the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

The triazole ring linkage formed by the alkyne-azide cycloaddition has similar characteristics (e.g., physical, biological, biochemical, chemical characteristics, etc.) as a natural phosphodiester bond present in nucleic acids and therefore is a nucleic acid backbone mimic. Consequently, conventional enzymes that recognize natural nucleic acids as substrates also recognize as substrates the products formed by alkyne-azide cycloaddition as provided by the technology described herein. See, e.g., El-Sagheer et al. (2011) "Biocompatible artificial DNA linker that is read through by DNA polymerases and is functional in *Escherichia coli*", Proc Natl Acad Sci USA 108(28): 11338-43.

In some embodiments, the use of nucleotide analogs comprising an alkyne (e.g., a 3'-O-propargyl nucleotide analog) produces nucleic acids (e.g., DNA or RNA polynucleotide fragments) that have a terminal 3' alkyne group. For example, in some embodiments, nucleotide analogs comprising an alkyne (e.g., a 3'-O-propargyl nucleotide analog) are incorporated into a growing strand of a nucleic acid in a polymerase extension reaction; once incorporated, the nucleotide analogs halt the polymerase reaction. These terminated nucleic acids are an appropriate chemical reactant for a click chemistry reaction (e.g., alkyne-azide cycloaddition), e.g., for a chemical ligation to an azide-modified molecule such as a 5'-azide modified nucleic acid, a labeling moiety comprising an azide, a solid support comprising an azide, a protein comprising an azide, etc., including, but not limited to moieties, entities, and components discussed herein. In some embodiments, for example, the 3'-O-propargyl group at the 3' terminal of the nucleic acid product is used in a tagging reaction with an azide-modified tag using chemical ligation, e.g., as provided by a click chemistry reaction. The covalent linkage created using this chemistry mimics that of a natural nucleic acid phosphodiester bond, thereby providing for the use of the chemically ligated nucleic acids in subsequent enzymatic reactions, such as a polymerase chain reaction, with the triazole chemical linkage causing minimal, limited, or undetectable (e.g., no) inhibition of the enzymatic reaction.

In some embodiments, the nucleotide analog comprising an alkyne is reacted with a reactant comprising a phosphine moiety in a Staudinger ligation. In a Staudinger ligation, an electrophilic trap (e.g., a methyl ester) is placed on a triarylphosphine aryl group (usually ortho to the phosphorus atom) and reacted with the azide to yield an aza-ylide intermediate, which then rearranges (e.g., in aqueous media) to produce a compound with amide group and a phosphine oxide function. The Staudinger ligation ligates (attaches and covalently links) the two starting molecules together.

Accordingly, provided herein is technology related to a composition comprising a nucleotide analog having a structure according to:

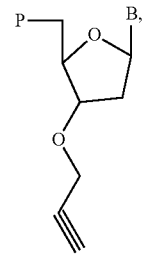

wherein B is a base and P comprises a phosphate moiety. In some embodiments, P comprises a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate.

In some embodiments, P comprises an azide (e.g., $N_3$, e.g., N=N=N), thus providing, in some embodiments, a directional, bi-functional polymerization agent as described herein.

In some embodiments, B is a cytosine, guanine, adenine, thymine, or uracil base. That is, in some embodiments, B is a purine or a pyrimidine or a modified purine or a modified pyrimidine. The technology is not limited in the bases B that find use in the nucleotide analogs. For example, B can be any synthetic, artificial, or natural base; thus, in some embodiments B is a synthetic base; in some embodiments, B is an artificial base; in some embodiments, B is a natural base. In some embodiments, compositions comprise a nucleotide analog and a nucleic acid (e.g., a polynucleotide). Compositions in some embodiments further comprise a polymerase and/or a nucleotide (e.g., a conventional nucleotide). In compositions comprising a nucleotide and a nucleotide analog, in some embodiments the number ratio of the nucleotide analog to the nucleotide is 1:1, 1:2, 1:3, 1:4, 1:5, 1:10, 1:15, 1:20, 1:25, 1:30, 1:50, 1:75, 1:100, 1:200, 1:300, 1:400, 1:500, 1:600, 1:700, 1:800, 1:900, 1:1000, 1:5000, or 1:10000.

In some embodiments, a nucleic acid comprises a nucleotide analog as provided herein. In some embodiments, the nucleic acid comprises the nucleotide analog at its 3' end (e.g., the nucleotide analog is at the 3' end of the nucleic acid). The technology, in some embodiments relates to the synthesis of a nucleic acid comprising a nucleotide analog by a biological enzyme. That is, the biological enzyme recognizes the nucleotide analog as a substrate and incorporates the nucleotide analog into the nucleic acid. For example, in some embodiments, the nucleic acid is produced by a polymerase.

In some embodiments, the compositions further comprise an azide, e.g., a component, entity, molecule, surface, biomolecule, etc., comprising an azide.

In some embodiments, the compositions comprise multiple nucleic acids; accordingly, in some embodiments, compositions comprise a second nucleic acid (e.g., in addition to a nucleic acid comprising a nucleotide analog). The technology encompasses functionalized nucleic acids for reacting with a nucleic acid comprising a nucleotide analog. Thus, in some embodiments, the second nucleic acid comprises an azide moiety, e.g., in some embodiments, the second nucleic acid comprises an azide moiety at the 5' end of the second nucleic acid.

The technology is not limited in the entity (e.g., comprising an azide group) reacted with the nucleic acid comprising the nucleotide analog. For instance, in some embodiments, compositions further comprise a label comprising an azide, a tag comprising an azide, a solid support comprising an azide, a nucleotide comprising an azide, a biotin comprising an azide, or a protein comprising an azide. In some embodiments, an alkyne moiety and an azide moiety are reacted using a "click chemistry" reaction catalyzed by a copper-based catalyst. As such, in some embodiments compositions further comprise a copper-based catalyst reagent. The reaction of the azide and alkyne produces, in some embodiments, a triazole moiety. In some embodiments, a nucleic acid comprising an alkyne (e.g., a nucleic acid comprising a nucleotide analog comprising an alkyne) is reacted with a nucleic acid comprising an azide to produce a longer nucleic acid. As such, in some embodiments compositions according to the technology further comprise a nucleic acid comprising a triazole (e.g., that forms a link between the two nucleic acids). In some embodiments, the reaction of the alkyne and azide proceeds with regioselectivity, e.g., in some embodiments the nucleic acid comprises a 1',4' substituted triazole. In some embodiments, the nucleic acid comprising the nucleotide analog is reacted with an adaptor oligonucleotide, an adaptor oligonucleotide comprising a barcode, or a barcode oligonucleotide comprising an azide. Thus, in some embodiments are provided reaction mixtures comprising an adaptor oligonucleotide, an adaptor oligonucleotide comprising a barcode, or a barcode oligonucleotide.

In some embodiments, a nucleic acid (e.g., formed from uniting two nucleic acids by "click chemistry" reaction of an alkyne and an azide) comprises a structure according to:

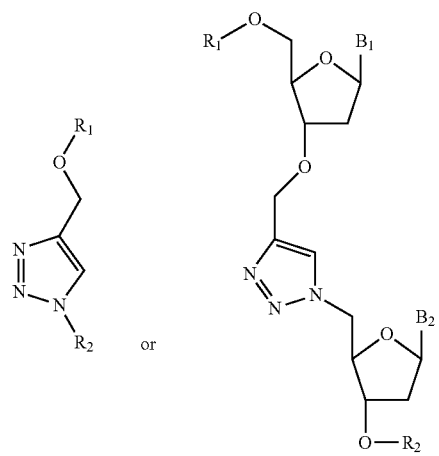

where $R_1$ and $R_2$ are individually any chemical structure or chemical moiety (and may be the same or different chemical structures or chemical moieties in different structures) and $B_1$ and $B_2$ individually indicate the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

Another aspect of the technology relates to embodiments of methods for synthesizing a modified nucleic acid, the method comprising providing a nucleotide analog comprising an alkyne group and linking a nucleic acid to the nucleotide analog to produce a modified nucleic acid comprising the nucleotide analog. In some embodiments, the nucleotide analog has a structure according to:

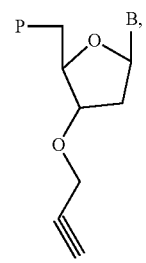

wherein B is a base (e.g., cytosine, guanine, adenine, thymine, or uracil) and P comprises a triphosphate moiety. Embodiments of the method comprise further providing, e.g., a template, a primer, a nucleotide (e.g., a conventional nucleotide), and/or a polymerase. The nucleotide analogs are recognized as a substrate by biological enzymes such as polymerases; thus, in some embodiments, a polymerase catalyzes linking a nucleic acid to the nucleotide analog to produce a modified nucleic acid comprising the nucleotide analog. The modified nucleic acid provides a substrate for reaction with an azide-carrying entity, e.g., to form a conjugated product by a "click chemistry" reaction. Thus, in some embodiments the methods further comprise reacting the modified nucleic acid with an azide moiety. The methods are not limited in the entity that comprises the azide moiety; for example, in some embodiments the methods comprise reacting the modified nucleic acid with a second nucleic acid comprising an azide moiety, e.g., reacting the modified nucleic acid with a second nucleic acid comprising an azide moiety at the 5' end of the second nucleic acid, a label comprising an azide, a tag comprising an azide, a solid support comprising an azide, a nucleotide comprising an azide, and/or a protein comprising an azide.

The methods find use in linking an adaptor oligonucleotide (e.g., for use in next-generation sequencing) to a nucleic acid comprising a nucleotide analog. Accordingly, in some embodiments, the methods further comprise reacting the modified nucleic acid with an adaptor oligonucleotide comprising an azide moiety, an adaptor oligonucleotide comprising a barcode and comprising an azide moiety, and/or a barcode oligonucleotide comprising an azide moiety, e.g., to produce a nucleic acid-oligonucleotide conjugate. In some embodiments, reactions of a nucleotide analog (e.g., a nucleic acid comprising a nucleotide analog) and an azide are catalyzed by a copper-based catalyst reagent. Associated methods, according, in some embodiments comprise reacting the modified nucleic acid with an azide moiety and a copper-based catalyst reagent. As the triazole ring formed by the "click chemistry" reaction does not substantially and/or detectably inhibit biological enzyme activity, the nucleic acid-oligonucleotide conjugate provides a useful nucleic acid for further manipulation, e.g., in some embodiments the modified nucleic acid is a substrate for a biological enzyme, the modified nucleic acid is a substrate for a polymerase, and/or the modified nucleic acid is a substrate for a sequencing reaction.

The nucleotide analogs provided herein are functional terminators, e.g., they act to terminate synthesis of a nucleic acid (e.g., similar to a dideoxynucleotide as used in Sanger sequencing) while also comprising a reactive group for further chemical processing. Accordingly, as described herein, in some embodiments, the methods further comprise terminating polymerization with the nucleotide analog.

Related methods provide, in some embodiments, a method for sequencing a nucleic acid, the method comprising hybridizing a primer to a nucleic acid template to form a hybridized primer/nucleic acid template complex; providing a plurality of nucleotide analogs, each nucleotide analog comprising an alkyne moiety; reacting the hybridized primer/nucleic acid template complex and the nucleotide analog with a polymerase to add the nucleotide analog to the primer by a polymerase reaction to form an extended product comprising an incorporated nucleotide analog; and reacting the extended product with an azide-containing compound to form a structure comprising a triazole ring. In particular embodiments, the nucleotide analogs are 3'-O-propargyl-dNTP nucleotide analogs and N is selected from the group consisting of A, C, G, T and U. As the triazole ring formed by the "click chemistry" reaction does not substantially and/or detectably inhibit biological enzyme activity, the nucleic acid-oligonucleotide conjugate provides a useful nucleic acid for further manipulation. Thus, in some embodiments the structure comprising a triazole ring is used in subsequent enzymatic reactions, e.g., a polymerase chain reaction and/or a sequencing reaction. Polymerization in the presence of nucleotide analogs is performed, in some embodiments, in the presence also of conventional (e.g., non-terminator) nucleotides. Related methods comprise providing conventional nucleotides.

Also provided herein are embodiments of kits. For example, in some embodiments, kits are provided for synthesizing a modified nucleic acid, the kit comprising a nucleotide analog comprising an alkynyl group; and a copper-based catalyst reagent. In some embodiments kits further comprise other components that find use in the processing and/or manipulation of nucleic acids. Thus, in some embodiments kits further comprise a polymerase, an adaptor oligonucleotide comprising an azide moiety, and/or a nucleotide (e.g., a conventional nucleotide).

For example, some embodiments of the technology relate to kits for producing a NGS sequencing library and/or for obtaining sequence information from a target nucleic acid. For example, some embodiments provide a kit comprising a nucleotide analog, e.g., for producing a nucleotide fragment ladder according to the methods provided herein. In some embodiments, the nucleotide analog is a 3'-O-blocked nucleotide analog, e.g., a 3'-O-alkynyl nucleotide analog, e.g., a 3'-O-propargyl nucleotide analog. In some embodiments, conventional A, C, G, U, and/or T nucleotides are provided in a kit as well as one or more (e.g., 1, 2, 3, or 4) A, C, G, U, and/or T nucleotide analogs.

In some embodiments, kits comprise a polymerase (e.g., a natural polymerase, a modified polymerase, and/or an engineered polymerase, etc.), e.g., for amplification (e.g., by thermal cycling, isothermal amplification) or for sequencing, etc. In some embodiments, kits comprise a ligase, e.g., for attaching adaptors to a nucleic acid such as an amplicon or a ladder fragment or for circularizing an adaptor-amplicon. Some embodiments of kits comprise a copper-based catalyst reagent, e.g., for a click chemistry reaction, e.g., to react an azide and an alkynyl group to form a triazole link. Some kit embodiments provide buffers, salts, reaction vessels, instructions, and/or computer software.

In some embodiments, kits comprise primers and/or adaptors. In some embodiments, the adaptors comprise a chemical modification suitable for attaching the adaptor to the nucleotide analog, e.g., by click chemistry. For example, in some embodiments, the kit comprises a nucleotide analog comprising an alkyne group and an adaptor oligonucleotide comprising an azide ($N_3$) group. In some embodiments, a "click chemistry" process such as an azide-alkyne cycloaddition is used to link the adaptor to the fragment via formation of a triazole.

Particular kit embodiments provide a kit for generating a sequencing library, the kit comprising an adaptor oligonucleotide comprising a first reactive group (e.g., an azide), a 3'-O-blocked nucleotide analog (e.g., a 3'-O-alkynyl nucleotide analog or a 3'-O-propargyl nucleotide analog, e.g., comprising an alkyne group, e.g., comprising a second reactive group that forms a chemical bond with the first reactive group, e.g., using click chemistry), a polymerase (e.g., a polymerase for isothermal amplification or thermal cycling), a second adaptor oligonucleotide, one or more compositions comprising a nucleotide or a mixture of nucleotides, and a ligase or a copper-based click chemistry catalyst reagent.

In some embodiments of kits, kits comprise one or more 3'-O-blocked nucleotide analog(s) (e.g., one or more 3'-O-alkynyl nucleotide analog(s) such as one or more 3'-O-propargyl nucleotide analog(s) and one or more adaptor oligonucleotides comprising an azide group (e.g., a 5'-azido oligonucleotide, e.g., a 5'-azido-methyl oligonucleotide). Some kit embodiments further provide a 5'-azido-methyl oligonucleotide comprising a barcode. Some kit embodiments further provide a plurality of 5'-azido-methyl oligonucleotides comprising a plurality of barcodes (e.g., each 5'-azido-methyl oligonucleotide comprises a barcode that is distinguishable from one or more other barcodes of one or more other 5'-azido-methyl oligonucleotide(s) comprising a different barcode). Further kit embodiments comprise a click chemistry catalytic reagent (e.g., a copper(I) catalytic reagent).

Some kit embodiments comprise one or more standard dNTPs in addition to the one or more one or more 3'-O-blocked nucleotide analog(s) (e.g., one or more 3'-O-alkynyl nucleotide analog(s) such as one or more 3'-O-propargyl nucleotide analog(s). For instance, some kit embodiment provide dATP, dCTP, dGTP, and dTTP, either in separate vessels or as a mixture with one or more 3'-O-propargyl-dATP, 3'-O-propargyl-dCTP, 3'-O-propargyl-dGTP, and/or 3'-O-propargyl-dATP.

Some kit embodiments further comprise a polymerase obtained from, derived from, isolated from, cloned from, etc. a *Thermococcus* species (e.g., an organism of the taxonomic lineage Archaea; Euryarchaeota; Thermococci; Thermococcales; Thermococcaceae; *Thermococcus*). In some embodiments, the polymerase is obtained from, derived from, isolated from, cloned from, etc. a *Thermococcus* species 9○N-7. In some embodiments, the polymerase comprises amino acid substitutions that provide for improved incorporation of modified substrates such as modified dideoxynucleotides, ribonucleotides, and acyclonucleotides. In some embodiments, the polymerase comprises amino acid substitutions that provide for improved incorporation of nucleotide analogs comprising modified 3' functional groups such as the 3'-O-propargyl dNTPs described herein. In some embodiments the amino acid sequence of the polymerase comprises one or more amino acid substitutions relative to the *Thermococcus* sp. 9○N-7 wild-type polymerase amino acid sequence, e.g., a substitution of alanine for the aspartic acid at amino acid position 141 (D141A), a substitution of alanine for the glutamic acid at amino acid position 143 (E143A), a substitution of valine for the tyrosine at amino acid position 409 (Y409V), and/or a substitution of leucine for the alanine at amino acid position 485 (A485L). In some embodiments, the polymerase is provided in a heterologous host organism such as *Escherichia coli* that comprises a cloned *Thermococcus* sp. 9○N-7 polymerase gene, e.g., comprising one or more mutations (e.g., D141A, E143A, Y409V, and/or A485L). In some embodiments, the polymerase is a *Thermococcus* sp. 9○N-7 polymerase sold under the trade name THERMINATOR (e.g., THERMINATOR II) by New England BioLabs (Ipswich, Mass.).

Accordingly, some kit embodiments comprise one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP), a mixture of standard dNTPs (e.g., dATP, dCTP, dGTP, and dTTP), one or more 5'-azido-methyl oligonucleotide adaptors, a polymerase obtained from, derived from, isolated from, cloned from, etc. a *Thermococcus* species, and a click chemistry catalyst for forming a triazole from an azide group and an alkyl group. In some embodiments, the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP) are provided together, e.g., the kit comprises a solution comprising the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP). In some embodiments, the solution comprises the one or more 3'-O-propargyl nucleotide analog(s) (e.g., one or more of 3'-O-propargyl-dATP, 3'-O-propargyl-dCTP, 3'-O-propargyl-dGTP, and/or 3'-O-propargyl-dATP) and the mixture of standard dNTPs (e.g., dATP, dCTP, dGTP, and dTTP) at a ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1).

Some embodiments of kits further comprise software for processing sequence data, e.g., to extract nucleotide sequence data from the data produced by a sequencer; to identify barcodes and target subsequences from the data produced by a sequencer; to align and/or assemble subsequences from the data produced by a sequencer to produce a consensus sequence; and/or to align subsequences and/or a consensus sequence to a reference sequence.

In some embodiments, provided herein are compositions comprising a nucleotide analog having a structure according to:

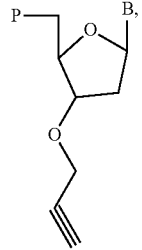

wherein B is a base (e.g., a purine or a pyrimidine such as a cytosine, guanine, adenine, thymine, or uracil; e.g., a modified purine or a modified pyrimidine) and P comprises a phosphate moiety (e.g., a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate); a nucleic acid; a polymerase; and a nucleotide (e.g., comprising the base B, e.g., in a number ratio of the nucleotide analog to the nucleotide that is 1:1, 1:2, 1:3, 1:4, 1:5, 1:10, 1:15, 1:20, 1:25, 1:30, 1:50, 1:75, 1:100, 1:200, 1:300, 1:400, 1:500, 1:600, 1:700, 1:800, 1:900, 1:1000, 1:5000, or 1:10000).

Also provided are embodiments of compositions comprising a nucleic acid (e.g., produced by a polymerase), wherein the nucleic acid comprises a nucleotide analog (e.g., at its 3' end) having a structure according to:

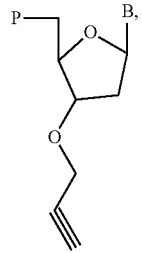

wherein B is a base (e.g., a purine or a pyrimidine such as a cytosine, guanine, adenine, thymine, or uracil; e.g., a modified purine or a modified pyrimidine) and P comprises a phosphate moiety (e.g., a tetraphosphate; a triphosphate; a diphosphate; a monophosphate; a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate); a second nucleic acid (e.g., comprising an azide, e.g., at its 5' end), a label comprising an azide, a tag comprising an azide, a solid support comprising an azide, a nucleotide comprising an azide, a biotin comprising an azide, or a protein comprising an azide; a copper (e.g., copper-based) catalyst reagent; a nucleic acid comprising a triazole (e.g., a 1',4' substituted triazole); and/or a structure such as:

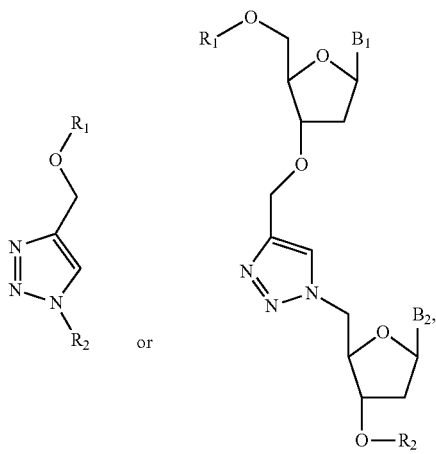

where $R_1$ and $R_2$ are individually any chemical structure or chemical moiety (and may be the same or different chemical structures or chemical moieties in different structures) and $B_1$ and $B_2$ individually indicate the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.); an adaptor oligonucleotide, an adaptor oligonucleotide comprising a barcode, or a barcode oligonucleotide.

In another aspect, the technology provides a method for synthesizing a modified nucleic acid, the method comprising providing a nucleotide analog comprising an alkyne group, e.g., a nucleotide having a structure according to:

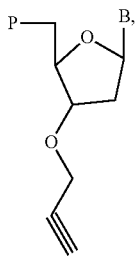

wherein B is a base (e.g., cytosine, guanine, adenine, thymine, or uracil) and P comprises a triphosphate moiety; linking a nucleic acid to the nucleotide analog to produce a modified nucleic acid comprising the nucleotide analog; providing a template; providing a primer; providing a nucleotide; providing a polymerase (e.g., to catalyze the linking of the nucleic acid to the nucleotide analog); terminating polymerization with the nucleotide analog; reacting the modified nucleic acid with an azide moiety (e.g., with a second nucleic acid comprising an azide moiety at its 5' end, a label comprising an azide, a tag comprising an azide, a solid support comprising an azide, a nucleotide comprising an azide, a protein comprising an azide, an adaptor oligonucleotide comprising an azide moiety, an adaptor oligonucleotide comprising a barcode and comprising an azide moiety, or a barcode oligonucleotide comprising an azide moiety), e.g., to produce a nucleic acid-oligonucleotide conjugate (e.g., that is a substrate for a biological enzyme such as a polymerase and/or to provide a substrate for a sequencing reaction); and/or reacting the modified nucleic acid with an azide moiety and a copper-based catalyst reagent.

In some embodiments are provided a method for sequencing a nucleic acid, the method comprising hybridizing a primer to a nucleic acid template to form a hybridized primer/nucleic acid template complex; providing a plurality of nucleotide analogs (e.g., 3'-O-propargyl-dNTP nucleotide analogs wherein N is selected from the group consisting of A, C, G, T, and U), each nucleotide analog comprising an alkyne moiety; providing conventional nucleotides; reacting the hybridized primer/nucleic acid template complex and the nucleotide analog with a polymerase to add the nucleotide analog to the primer by a polymerase reaction to form an extended product comprising an incorporated nucleotide analog; and reacting the extended product with an azide-containing compound to form a structure comprising a triazole ring (e.g., that is used in subsequent enzymatic reactions such as a polymerase chain reaction).

In some embodiments are provided a kit for synthesizing a modified nucleic acid, the kit comprising a nucleotide analog comprising an alkynyl group; a copper-based catalyst reagent; a polymerase; an adaptor oligonucleotide comprising an azide moiety; and a conventional nucleotide.

Particular embodiments are related to generating a nucleic acid fragment ladder using a polymerase reaction comprising standard dNTPs and 3'-O-propargyl-dNTPs at a molar ratio of from 1:500 to 500:1 (standard dNTPs to 3'-O-propargyl-dNTPs). Terminated nucleic acid fragments produced by methods described herein comprise a propargyl group on their 3' ends. Further embodiments are related to attaching an adaptor to the 3' ends of the nucleic acid fragments using chemical conjugation. For example, in some embodiments a 5'-azido-modified oligonucleotide (e.g., a 5'-azido-methyl-modified oligonucleotide) is conjugated to the 3'-propargyl-terminated nucleic acid fragments by click chemistry (e.g., in a reaction catalyzed by a copper (e.g., copper (I)) reagent). In some embodiments, a target region is first amplified (e.g., by PCR) to produce a target amplicon for sequencing. In some embodiments, amplifying the target region comprises amplification of the target region for 5 to 15 cycles (e.g., a "limited cycle" or "low-cycle" amplification).

Further embodiments provide that the target amplicon comprises a tag (e.g., comprises a barcode sequence), e.g., the target amplicon is an identifiable amplicon. In some embodiments, a primer used in the amplification of the target region comprises a tag (e.g., comprising a barcode sequence)

that is subsequently incorporated into the target amplicon (e.g., in a "copy and tag" reaction) to produce an identifiable amplicon. In some embodiments, an adaptor comprising the tag (e.g., comprising a barcode sequence) is ligated to the target amplicon after amplification (e.g., in a ligase reaction) to produce an identifiable adaptor-amplicon. In some embodiments, the primer used to produce an identifiable amplicon in a copy and tag reaction comprises a 3' region comprising a target-specific priming sequence and a 5' region comprising two different universal sequences (e.g., a universal sequence A and a universal sequence B) flanking a degenerate sequence. In some embodiments, an adaptor ligated to an amplicon to produce an identifiable adaptor-amplicon is a double stranded adaptor, e.g., comprising one strand comprising a degenerate sequence (e.g., comprising 8 to 12 bases) flanked on both the 5' end and the 3' end by two different universal sequences (e.g., a universal sequence A and a universal sequence B) and a second strand comprising a universal sequence C (e.g., at the 5' end) and a sequence (e.g., at the 3' end) that is complementary to the universal sequence B and that has an additional T at the 3'-terminal position.

Embodiments of the technology provide for the generation of nucleic acid ladder fragments from an adaptor-amplicon, e.g., to provide a sequencing library for NGS. In particular, the technology provides for the generation of a 3'-O-propargyl-dN terminated nucleic acid ladder for nucleic acid sequencing (e.g., NGS), e.g., by using a polymerase reaction comprising standard dNTPs and 3'-O-propargyl-dNTPs at a molar ratio of from 1:500 to 500:1 (standard dNTPs to 3'-O-propargyl-dNTPs). Then, in some embodiments, the technology provides for attaching an adaptor to the 3' ends of the nucleic acid fragments using chemical conjugation. For example, in some embodiments, a 5'-azido-modified oligonucleotide (e.g., a 5'-azido-methyl-modified oligonucleotide) is conjugated to the 3'-propargyl-terminated nucleic acid fragments by click chemistry (e.g., in a reaction catalyzed by a copper (e.g., copper (I)) reagent).

Some embodiments of the technology provide a composition for use as a next-generation sequencing library to obtain a sequence of a target nucleic acid, the composition comprising n nucleic acids (e.g., a nucleic acid fragment library), wherein each of the n nucleic acids comprises a 3'-O-blocked nucleotide analog (e.g., a 3'-O-alkynyl nucleotide analog such as a 3'-O-propargyl nucleotide analog). In some embodiments, each nucleic acid of the n nucleic acids comprises a nucleotide subsequence of a target nucleotide sequence. In particular, embodiments provide a composition comprising n nucleic acids, wherein each of the n nucleic acids is terminated by a 3'-O-blocked nucleotide analog (e.g., a 3'-O-alkynyl nucleotide analog such as a 3'-O-propargyl nucleotide analog). Further embodiments provide a composition comprising n nucleic acids (e.g., a nucleic acid fragment library), wherein each of the n nucleic acids comprises a 3'-O-blocked nucleotide analog (e.g., a 3'-O-alkynyl nucleotide analog such as a 3'-O-propargyl nucleotide analog) and each of the n nucleic acids is conjugated (e.g., linked) to an oligonucleotide adaptor by a triazole linkage (e.g., a linkage formed from a chemical conjugation of a propargyl group and an azido group, e.g., by a click chemistry reaction). For example, some embodiments provide a composition comprising n nucleic acids (e.g., a nucleic acid fragment library), wherein each of the n nucleic acids comprises a 3'-O-propargyl nucleotide analog (e.g., a 3'-O-propargyl-dA, 3'-O-propargyl-dC, 3'-O-propargyl-dG, and/or a 3'-O-propargyl-dT) conjugated (e.g., linked) to an oligonucleotide adaptor by a triazole linkage (e.g., a linkage formed from a chemical conjugation of a propargyl group and an azido group, e.g., by a click chemistry reaction).

In some embodiments, the composition for use as a next-generation sequencing library to obtain a sequence of a target nucleic acid is produced by a method comprising synthesizing a n nucleic acids (e.g., a nucleic acid fragment library) using a mixture of dNTPs and one or more 3'-O-blocked nucleotide analog(s) (e.g., one or more 3'-O-alkynyl nucleotide analog(s) such as one or more 3'-O-propargyl nucleotide analog(s)), e.g., at a molar ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1). In some embodiments, the composition is produced using a polymerase obtained from, derived from, isolated from, cloned from, etc. a *Thermococcus* species (e.g., an organism of the taxonomic lineage Archaea; Euryarchaeota; Thermococci; Thermococcales; Thermococcaceae; *Thermococcus*). In some embodiments, the polymerase is obtained from, derived from, isolated from, cloned from, etc. a *Thermococcus* species 9∘N-7. In some embodiments, the polymerase comprises amino acid substitutions that provide for improved incorporation of modified substrates such as modified dideoxynucleotides, ribonucleotides, and acyclonucleotides. In some embodiments, the polymerase comprises amino acid substitutions that provide for improved incorporation of nucleotide analogs comprising modified 3' functional groups such as the 3'-O-propargyl dNTPs described herein. In some embodiments the amino acid sequence of the polymerase comprises one or more amino acid substitutions relative to the *Thermococcus* sp. 9∘N-7 wild-type polymerase amino acid sequence, e.g., a substitution of alanine for the aspartic acid at amino acid position 141 (D141A), a substitution of alanine for the glutamic acid at amino acid position 143 (E143A), a substitution of valine for the tyrosine at amino acid position 409 (Y409V), and/or a substitution of leucine for the alanine at amino acid position 485 (A485L). In some embodiments, the polymerase is provided in a heterologous host organism such as *Escherichia coli* that comprises a cloned *Thermococcus* sp. 9∘N-7 polymerase gene, e.g., comprising one or more mutations (e.g., D141A, E143A, Y409V, and/or A485L). In some embodiments, the polymerase is a *Thermococcus* sp. 9∘N-7 polymerase sold under the trade name THERMINATOR (e.g., THERMINATOR II) by New England BioLabs (Ipswich, Mass.).

Accordingly, the technology relates to reaction mixtures comprising a target nucleic acid, a mixture of dNTPs and one or more 3'-O-blocked nucleotide analog(s) (e.g., one or more 3'-O-alkynyl nucleotide analog(s) such as one or more 3'-O-propargyl nucleotide analog(s)), e.g., at a molar ratio of from 1:500 to 500:1 (e.g., 1:500, 1:450, 1:400, 1:350, 1:300, 1:250, 1:200, 1:150, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, or 500:1), and a polymerase for synthesizing a nucleic acid using the dNTPs and one or more 3'-O-blocked nucleotide analog(s) (e.g., a polymerase obtained from, derived from, isolated from, cloned from, etc. a *Thermococcus* species). In some embodiments, the target nucleic acid is an amplicon. In some embodiments, the target nucleic acid comprises a barcode. In some embodiments, the target nucleic acid is an amplicon comprising a barcode. In some embodiments, the target nucleic acid is an amplicon ligated to an adaptor comprising a barcode. Some embodiments provide reaction mixtures that comprises a plurality of target nucleic acids, each target nucleic acid comprising a barcode associated with an identifiable characteristic of the target nucleic acid.

Some embodiments provide a reaction mixture composition comprising a template (e.g., a circular template, e.g., comprising a universal nucleotide sequence and/or a barcode nucleotide sequence) comprising a subsequence of a target nucleic acid, a polymerase, one or more fragments of a ladder fragment library, and a 3'-O-blocked nucleotide analog.

Some embodiments provide a reaction mixture composition comprising a library of nucleic acids, the library of nucleic acids comprising overlapping short nucleotide sequences tiled over a target nucleic acid (e.g., the overlapping short nucleotide sequences cover a region of the target nucleic acid comprising 100 bases, 200 bases, 300 bases, 400 bases, 500 bases, 600 bases, 700 bases, 800 bases, 900 bases, 1000 bases, or more than 1000 bases, e.g., 2000 bases, 2500 bases, 3000 bases, 3500 bases, 4000 bases, 4500 bases, 5000 bases, or more than 5000 bases) and offset from one another by 1-20, 1-10, or 1-5 bases (e.g., 1 base) and each nucleic acid of the library comprising less than 100 bases, less than 90 bases, less than 80 bases, less than 70 bases, less than 60 bases, less than 50 bases, less than 45 bases, less than 40 bases, less than 35 bases, or less than 30 bases.

Additional embodiments are provided below and as variations of the technology described as understood by a person having ordinary skill in the art.

BRIEF DESCRIPTION OF THE DRAWINGS

These and other features, aspects, and advantages of the present technology will become better understood with regard to the following drawings:

FIG. 3A shows $^1$H NMR data for 3'-O-propargyl-dCTP. FIG. 3B shows an enlarged portion of the $^1$H NMR data for 3'-O-propargyl-dCTP shown in FIG. 3A. FIG. 3C shows an enlarged portion of the $^1$H NMR data for 3'-O-propargyl-dCTP shown in FIG. 3A. FIG. 3D shows $^{31}$P NMR data for 3'-O-propargyl-dCTP. FIG. 3E shows an enlarged portion of the $^{31}$P NMR data for 3'-O-propargyl-dCTP shown in FIG. 3D. FIG. 3F shows anion-exchange HPLC data for 3'-O-propargyl-dCTP. FIG. 3G shows high-resolution mass spectrum data for 3'-O-propargyl-dCTP.

FIG. 4A shows $^1$H NMR data for 3'-O-propargyl-dTTP. FIG. 4B shows an enlarged portion of the $^1$H NMR data for 3'-O-propargyl-dTTP shown in FIG. 4A. FIG. 4C shows an enlarged portion of the $^1$H NMR data for 3'-O-propargyl-dTTP shown in FIG. 4A. FIG. 4D shows $^{31}$P NMR data for 3'-O-propargyl-dTTP. FIG. 4E shows an enlarged portion of the $^{31}$P NMR data for 3'-O-propargyl-dTTP shown in FIG. 4D. FIG. 4F shows anion-exchange HPLC data for 3'-O-propargyl-dTTP. FIG. 4G shows high-resolution mass spectrum data for 3'-O-propargyl-dTTP.

FIG. 5A shows $^1$H NMR data for 3'-O-propargyl-dATP. FIG. 5B shows an enlarged portion of the $^1$H NMR data for 3'-O-propargyl-dATP shown in FIG. 5A. FIG. 5C shows an enlarged portion of the $^1$H NMR data for 3'-O-propargyl-dATP shown in FIG. 5A. FIG. 5D shows $^{31}$P NMR data for 3'-O-propargyl-dATP. FIG. 5E shows an enlarged portion of the $^{31}$P NMR data for 3'-O-propargyl-dATP shown in FIG. 5D. FIG. 5F shows anion-exchange HPLC data for 3'-O-propargyl-dATP. FIG. 5G shows high-resolution mass spectrum data for 3'-O-propargyl-dATP.

FIG. 6A shows $^1$H NMR data for 3'-O-propargyl-dGTP. FIG. 6B shows an enlarged portion of the $^1$H NMR data for 3'-O-propargyl-dGTP shown in FIG. 6A. FIG. 6C shows an enlarged portion of the $^1$H NMR data for 3'-O-propargyl-dGTP shown in FIG. 6A. FIG. 6D shows $^{31}$P NMR data for 3'-O-propargyl-dGTP. FIG. 6E shows an enlarged portion of the $^{31}$P NMR data for 3'-O-propargyl-dGTP shown in FIG. 6D. FIG. 6F shows anion-exchange HPLC data for 3'-O-propargyl-dGTP. FIG. 6G shows high-resolution mass spectrum data for 3'-O-propargyl-dGTP.

Figure 1:
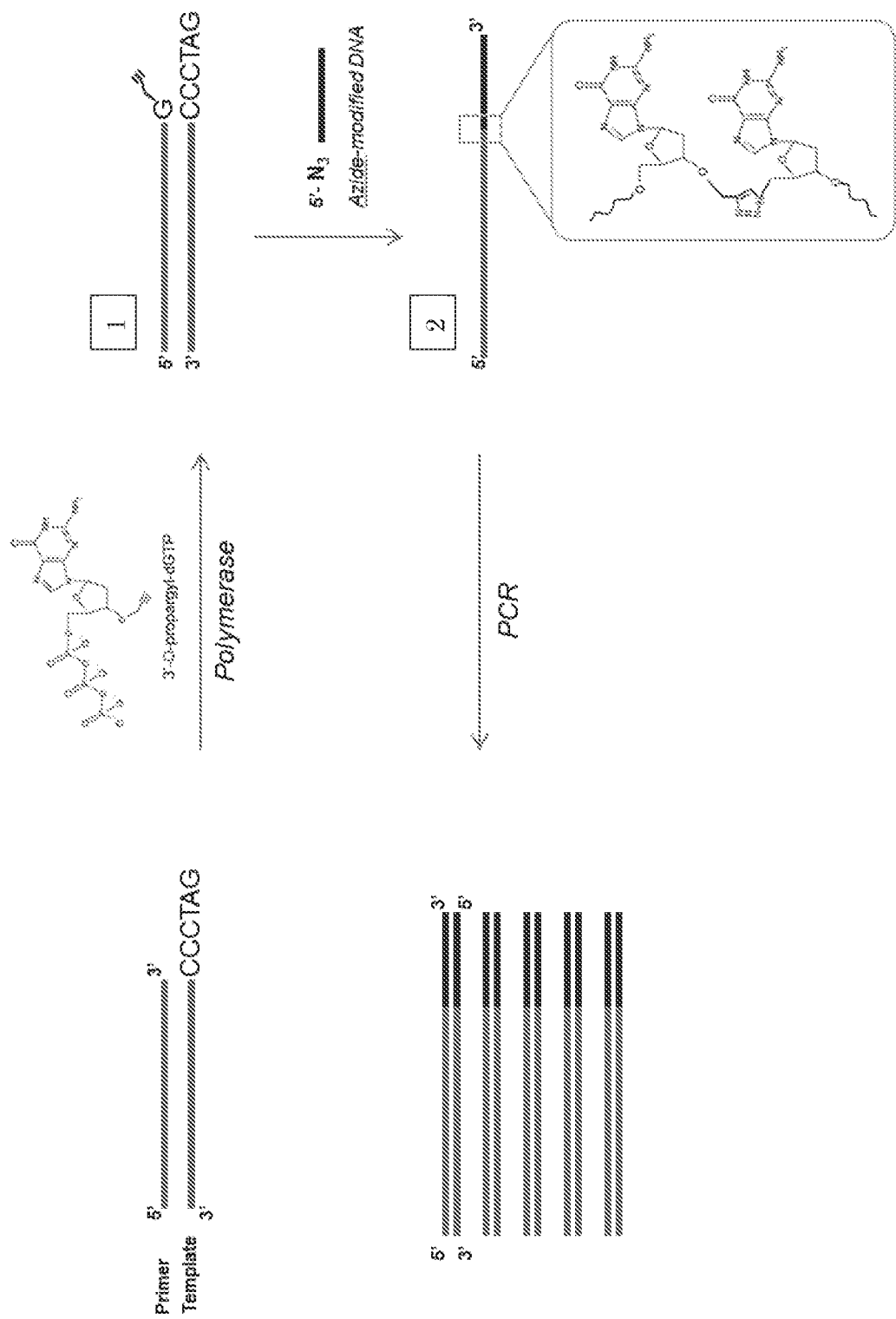
FIG. 1 is a schematic showing a polymerase extension reaction using 3'-O-propargyl-dGTP. The polymerase extension halts after the incorporation of 3'-O-propargyl-dGTP, producing product 1. A 5'-azide-modified DNA fragment is chemically ligated to product 1 using click chemistry producing product 2. The covalent linkage created by the formation of the triazole ring mimics that of the natural DNA backbone phosphodiester linkage. Product 2 is used subsequently in enzymatic reactions (e.g., PCR).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to the manipulation and detection of nucleic acids, including but not limited to compositions, methods, systems, and kits related to nucleotides comprising a chemically reactive linking moiety. In particular embodiments, the technology provides nucleotide analogs comprising a base (e.g., adenine, guanine, cytosine, thymine, or uracil), a sugar (e.g., a ribose or deoxyribose), and an alkyne chemical moiety, e.g., attached to the 3' oxygen of the sugar (e.g., the 3' oxygen of the deoxyribose or the 3' oxygen of the ribose). The nucleotide analogs (e.g., a 3'-alkynyl nucleotide analog, e.g., a 3'-O-propargyl nucleotide analog such as a 3'-O-propargyl dNTP or a 3'-O-propargyl NTP) find use in embodiments of the technology to introduce a particular chemical moiety (e.g., an alkyne) at the end (e.g., the 3' end) of a nucleic acid (e.g., a DNA or RNA) by a polymerase extension reaction, and, consequently, to produce a nucleic acid modification that does not exist in natural biological systems. Chemical ligation between the polymerase extension products and appropriate conjugation partners (e.g., azide modified entities) is achieved with high efficiency and specificity using click chemistry. Embodiments of the functional nucleotide terminators provided herein are used to produce nucleic acids that are useful for various molecular biology, biochemical, and biotechnology applications.

The technology provides several advantages over current technologies. For instance, the technology provides sequence data that is better (e.g., higher quality, longer reads, fewer errors, etc.) or comparable than existing technologies in a shorter run time than existing technologies. Moreover, the technology provides sequence data reads that can be stitched together to provide a longer read of high quality.

The section headings used herein are for organizational purposes only and are not to be construed as limiting the described subject matter in any way. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.
Definitions To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleotide" comprises a "base" (alternatively, a "nucleobase" or "nitrogenous base"), a "sugar" (in particular, a five-carbon sugar, e.g., ribose or 2-deoxyribose), and a "phosphate moiety" of one or more phosphate groups (e.g., a monophosphate, a diphosphate, a triphosphate, a tetraphosphate, etc. consisting of one, two, three, four or more linked phosphates, respectively). Without the phosphate moiety, the nucleobase and the sugar compose a "nucleoside". A nucleotide can thus also be called a nucleoside monophosphate or a nucleoside diphosphate or a nucleoside triphosphate, depending on the number of phosphate groups attached. The phosphate moiety is usually attached to the 5-carbon of the sugar, though some nucleotides comprise phosphate moieties attached to the 2-carbon or the 3-carbon of the sugar. Nucleotides contain either a purine (e.g., in the nucleotides adenine and guanine) or a pyrimidine base (e.g., in the nucleotides cytosine, thymine, and uracil). Some nucleotides contain non-natural bases. Ribonucleotides are nucleotides in which the sugar is ribose. Deoxyribonucleotides are nucleotides in which the sugar is deoxyribose.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA that is complementary DNA produced from an RNA template, for example by the action of a reverse transcriptase. It is well known that DNA (deoxyribonucleic acid) is a chain of nucleotides consisting of 4 types of nucleotides—A (adenine), T (thymine), C (cytosine), and G (guanine)—and that RNA (ribonucleic acid) is a chain of nucleotides consisting of 4 types of nucleotides—A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)) and cytosine (C) pairs with guanine (G), so that each of these base pairs forms a double strand. As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases (e.g., adenine, guanine, cytosine, and thymine/uracil) in a molecule (e.g., a whole genome, a whole transcriptome, an exome, oligonucleotide, polynucleotide, fragment, etc.) of DNA or RNA It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, pore-based (e.g., nanopore), visualization-based systems, etc.

Reference to a base, a nucleotide, or to another molecule may be in the singular or plural. That is, "a base" may refer to a single molecule of that base or to a plurality of the base, e.g., in a solution.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3 to 4, to several hundreds of monomeric units. Whenever a polynucleotide such as an oligonucleotide is represented by a sequence of letters, such as "ATGCCTG", it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the phrase "dNTP" means deoxynucleotidetriphosphate, where the nucleotide comprises a nucleotide base, such as A, T, C, G or U.

The term "monomer" as used herein means any compound that can be incorporated into a growing molecular chain by a given polymerase. Such monomers include, without limitation, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors or any other molecule that can be incorporated into a growing polymer chain by a given polymerase.

As used herein, "complementary" generally refers to specific nucleotide duplexing to form canonical Watson-Crick base pairs, as is understood by those skilled in the art. However, complementary also includes base-pairing of nucleotide analogs that are capable of universal base-pairing with A, T, G or C nucleotides and locked nucleic acids that enhance the thermal stability of duplexes. One skilled in the art will recognize that hybridization stringency is a determinant in the degree of match or mismatch in the duplex formed by hybridization.

As used herein, "moiety" refers to one of two or more parts into which something may be divided, such as, for example, the various parts of a tether, a molecule, or a probe.

As used herein, a "linker" is a molecule or moiety that joins two molecules or moieties and/or provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., Nucleic Acids Res. 27: 4416-4426, 1999). Methods of derivatizing and coupling organic molecules are well known in the arts of organic and bioorganic chemistry. A linker may also be cleavable (e.g., photocleavable) or reversible.

A "polymerase" is an enzyme generally for joining 3'-OH, 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9oN DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs) (e.g., Therminator I, Therminator II, and other variants), KOD HiFi. DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants such as exo-polymerases and other mutants, e.g., that tolerate modified (e.g., labeled) nucleotides and incorporate them into a strand of nucleic acid.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers depends on many factors including temperature, source of primer, and the use of the method.

As used herein, an "adaptor" is an oligonucleotide that is linked or is designed to be linked to a nucleic acid to introduce the nucleic acid into a sequencing workflow. An adaptor may be single-stranded or double-stranded (e.g., a double-stranded DNA or a single-stranded DNA). As used herein, the term "adaptor" refers to the adaptor nucleic in a state that is not linked to another nucleic acid and in a state that is linked to a nucleic acid.

At least a portion of the adaptor comprises a known sequence. For example, some embodiments of adaptors comprise a primer binding sequence for amplification of the nucleic acid and/or for binding of a sequencing primer. Some adaptors comprise a sequence for hybridization of a complementary capture probe. Some adaptors comprise a chemical or other moiety (e.g., a biotin moiety) for capture and/or immobilization to a solid support (e.g., comprising an avidin moiety). Some embodiments of adaptors comprise a marker, index, barcode, tag, or other sequence by which the adaptor and a nucleic acid to which it is linked are identifable.

Some adaptors comprise a universal sequence. A universal sequence is a sequence shared by a plurality of adaptors that may otherwise have different sequences outside of the universal sequence. For example, a universal sequence provides a common primer binding site for a collection of nucleic acids from different target nucleic acids, e.g., that may comprise different barcodes.

Some embodiments of adaptors comprise a defined but unknown sequence. For example, some embodiments of adaptors comprise a degenerate sequence of a defined number of bases (e.g., a 1- to 20-base degenerate sequence).

Such a sequence is defined even if each individual sequence is not known—such a sequence may nevertheless serve as an index, barcode, tag, etc. marking nucleic acid fragments from, e.g., the same target nucleic acid.

Some adaptors comprise a blunt end and some adaptors comprise an end with an overhang of one or more bases.

In particular embodiments provided herein, an adaptor comprises an azido moiety, e.g., the adaptor comprises an azido (e.g., an azido-methyl) moiety on its 5' end. Thus, some embodiments are related to adaptors that are or that comprise a 5'-azido-modified oligonucleotide or a 5'-azido-methyl-modified oligonucleotide.

In some embodiments, a unique index (a "marker" in some embodiments) is used to associate a fragment with the template nucleic acid from which it was produced. In some embodiments, a unique index is a unique sequence of synthetic nucleotides or a unique sequence of natural nucleotides that allows for easy identification of the target nucleic acid within a complicated collection of oligonucleotides (e.g., fragments) containing various sequences. In certain embodiments, unique index identifiers are attached to nucleic acid fragments prior to attaching adaptor sequences. In some embodiments, unique index identifiers are contained within adaptor sequences such that the unique sequence is contained in the sequencing reads. This ensures that homologous fragments can be detected based upon the unique indices that are attached to each fragment, thus further providing for unambiguous reconstruction of a consensus sequence. Homologous fragments may occur for example by chance due to genomic repeats, two fragments originating from homologous chromosomes, or fragments originating from overlapping locations on the same chromosome. Homologous fragments may also arise from closely related sequences (e.g., closely related gene family members, paralogs, orthologs, ohnologs, xenologs, and/or pseudogenes). Such fragments may be discarded to ensure that long fragment assembly can be computed unambiguously. The markers may be attached as described above for the adaptor sequences. The indices (e.g., markers) may be included in the adaptor sequences.

In some embodiments, the unique index (e.g., index identifier, tag, marker, etc.) is a "barcode". As used herein, the term "barcode" refers to a known nucleic acid sequence that allows some feature of a nucleic acid with which the barcode is associated to be identified. In some embodiments, the feature of the nucleic acid to be identified is the sample or source from which the nucleic acid is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some nucleic acids are of a different length than barcodes associated with other nucleic acids. In general, barcodes are of sufficient length and comprise sequences that are sufficiently different to allow the identification of samples based on barcodes with which they are associated. In some embodiments, a barcode and the sample source with which it is associated can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differs from every other barcode in the plurality at two or more nucleotide positions, such as at 2, 3, 4, 5, 6, 7, 8, 9, 10, or more positions. In some embodiments, one or more adaptors comprise(s) at least one of a plurality of barcode sequences. In some embodiments, methods of the technology further comprise identifying the sample or source from which a target nucleic acid is derived based on a barcode sequence to which the target nucleic acid is joined. In some embodiments, methods of the technology further comprise identifying the target nucleic acid based on a barcode sequence to which the target nucleic acid is joined. Some embodiments of the method further comprise identifying a source or sample of the target nucleotide sequence by determining a barcode nucleotide sequence. Some embodiments of the method further comprise molecular counting applications (e.g., digital barcode enumeration and/or binning) to determine expression levels or copy number status of desired targets. In general, a barcode may comprise a nucleic acid sequence that when joined to a target nucleic acid serves as an identifier of the sample from which the target polynucleotide was derived.

In some embodiments, an oligonucleotide such as a primer, adaptor, etc. comprises a "universal" sequence. A universal sequence is a known sequence, e.g., for use as a primer or probe binding site using a primer or probe of a known sequence (e.g., complementary to the universal sequence). While a template-specific sequence of a primer, a barcode sequence of a primer, and/or a barcode sequence of an adaptor might differ in embodiments of the technology, e.g., from fragment to fragment, from sample to sample, from source to source, or from region of interest to region of interest, embodiments of the technology provide that a universal sequence is the same from fragment to fragment, from sample to sample, from source to source, or from region of interest to region of interest so that all fragments comprising the universal sequence can be handled and/or treated in a same or similar manner, e.g., amplified, identified, sequenced, isolated, etc., using similar methods or techniques (e.g., using the same primer or probe).

In particular embodiments, a primer is used comprising a universal sequence (e.g., universal sequence A), a barcode sequence, and a template-specific sequence. In particular embodiments, a first adaptor comprising a universal sequence (e.g., universal sequence B) is used and in particular embodiments, a second adaptor comprising a universal sequence (e.g., universal sequence C) is used. Universal sequence A, universal sequence B, and universal sequence C can be any sequence. This nomenclature is used to note that the universal sequence A of a first nucleic acid (e.g., a fragment) comprising universal sequence A is the same as the universal sequence A of a second nucleic acid (e.g., a fragment) comprising universal sequence A, the universal sequence B of a first nucleic acid (e.g., a fragment) comprising universal sequence B is the same as the universal sequence B of a second nucleic acid (e.g., a fragment) comprising universal sequence B, and the universal sequence C of a first nucleic acid (e.g., a fragment) comprising universal sequence C is the same as the universal sequence C of a second nucleic acid (e.g., a fragment) comprising universal sequence C. While universal sequences A, B, and C are generally different in embodiments of the technology, they need not be. Thus, in some embodiments, universal sequences A and B are the same; in some embodiments, universal sequences B and C are the same; in some embodiments, universal sequences A and C are the same; and in some embodiments, universal sequences A, B, and C are the same. In some embodiments, universal sequences A, B, and C are different.

For example, if two regions of interest are to be sequenced (e.g., from the same or different sources or, e.g., from two different regions of the same nucleic acid, chromosome, gene, etc.), two primers may be used, one primer comprising a first template-specific sequence for priming from the first region of interest and a first barcode to associate the first amplified product with the first region of interest and a second primer comprising a second template-specific sequence for priming from the second region of interest and a second barcode to associate the second amplified product with the second region of interest. These two primers, however, in some embodiments, will comprise the same universal sequence (e.g., universal sequence A) for pooling and downstream processing together. Two or more universal sequences may be used and, in general, the number of universal sequences will be less than the number of target-specific sequences and/or barcode sequences for pooling of samples and treatment of pools as a single sample (batch).

Accordingly, in some embodiments, determining the first nucleotide subsequence and the second nucleotide subsequence comprises priming from a universal sequence. In some embodiments determining the first nucleotide subsequence and the second nucleotide subsequence comprises terminating polymerization with a 3'-O-blocked nucleotide analog. For example, in some embodiments determining the first nucleotide subsequence and the second nucleotide subsequence comprises terminating polymerization with a 3'-O-alkynyl nucleotide analog, e.g., in some embodiments determining the first nucleotide subsequence and the second nucleotide subsequence comprises terminating polymerization with a 3'-O-propargyl nucleotide analog. In some embodiments determining the first nucleotide subsequence and the second nucleotide subsequence comprises terminating polymerization with a nucleotide analog comprising a reversible terminator.

The obtained short sequence reads are partitioned according to their barcode (i.e., de-multiplexed) and reads originating from the same samples, sources, regions of interest, etc. are binned together, e.g., saved to separate files or held in an organized data structure that allows binned reads to be identified as such. Then the binned short sequences are assembled into a consensus sequence. Sequence assembly can generally be divided into two broad categories: de novo assembly and reference genome mapping assembly. In de novo assembly, sequence reads are assembled together so that they form a new and previously unknown sequence. In reference genome mapping, sequence reads are assembled against an existing backbone sequence (e.g., a reference sequence, etc.) to build a sequence that is similar but not necessarily identical to the backbone sequence.

Thus, in some embodiments, target nucleic acids corresponding to each region of interest are reconstructed using a de-novo assembly. To begin the reconstruction process, short reads are stitched together bioinformatically by finding overlaps and extending them to produce a consensus sequence. In some embodiments the method further comprises mapping the consensus sequence to a reference sequence. Methods of the technology take advantage of sequencing quality scores that represent base calling confidence to reconstruct full length fragments. In addition to de-novo assembly, fragments can be used to obtain phasing (assignment to homologous copies of chromosomes) of genomic variants by observing that consensus sequences originate from either one of the chromosomes.

As used herein, a "system" denotes a set of components, real or abstract, comprising a whole where each component interacts with or is related to at least one other component within the whole.

Various nucleic acid sequencing platforms, nucleic acid assembly and/or mapping systems (e.g., computer software and/or hardware) are described, e.g., in U.S. Pat. Appl. Pub. No. 2011/0270533, which is incorporated herein by reference.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "alkoxy" refers to a chemical substituent of the formula —OR, where R is an alkyl group. By "aryloxy" is meant a chemical substituent of the formula —OR', where R' is an aryl group.

As used herein, the term "alkyne" refers to a hydrocarbon comprising a carbon-carbon triple bond. One example of an alkyne-containing functional group is the propargyl group. Propargyl is an alkyl functional group of 2-propynyl with the structure HC≡C—$CH_2$—, derived from the alkyne propyne.

As used herein, the term "azide" or "azido" refers to any compound having the $N_3$-moiety therein. The azide may be an organic azide or a metal azide. One reaction involving azides is a type of click chemistry known as a copper (I)-catalyzed 1,3-dipolar cyclo-addition reaction. This reaction conjugates alkynes and azides to form a five-membered triazole ring that provides a covalent linkage.

As used herein, the term "backbone" refers to a structural component of a nucleic acid molecule that is a series of covalently bonded atoms that together create the continuous chain of the molecule. In "natural" nucleic acids the backbone comprises phosphodiester bonds linking alternating sugars (e.g., ribose or deoxyribose) and phosphate moieties (related to phosphoric acid).

As used herein a "target site" is a site of a subject at which it is desired for a bioactive agent to be delivered and to be active. A target site may be a cell, a cell type, a tissue, an organ, an area, or other designation of a subject's anatomy and/or physiology.

The terms "protein" and "polypeptide" refer to compounds comprising amino acids joined via peptide bonds and are used interchangeably. Conventional one and three-letter amino acid codes are used herein as follows—Alanine: Ala, A; Arginine: Arg, R; Asparagine: Asn, N; Aspartate: Asp, D; Cysteine: Cys, C; Glutamate: Glu, E; Glutamine: Gln, Q; Glycine: Gly, G; Histidine: His, H; Isoleucine: Ile, I; Leucine: Leu, L; Lysine: Lys, K; Methionine: Met, M; Phenylalanine: Phe, F; Proline: Pro, P; Serine: Ser, S; Threonine: Thr, T; Tryptophan: Trp, W; Tyrosine: Tyr, Y; Valine: Val, V. As used herein, the codes Xaa and X refer to any amino acid.

In some embodiments compounds of the technology comprise an antibody component or moiety, e.g., an antibody or fragments or derivatives thereof. As used herein, an "antibody", also known as an "immunoglobulin" (e.g., IgG, IgM, IgA, IgD, IgE), comprises two heavy chains linked to each other by disulfide bonds and two light chains, each of which is linked to a heavy chain by a disulfide bond. The specificity of an antibody resides in the structural complementarity between the antigen combining site of the antibody (or paratope) and the antigen determinant (or epitope). Antigen combining sites are made up of residues that are primarily from the hypervariable or complementarity determining regions (CDRs). Occasionally, residues from non-hypervariable or framework regions influence the overall domain structure and hence the combining site. In some embodiments the targeting moiety is a fragment of antibody, e.g., any protein or polypeptide-containing molecule that comprises at least a portion of an immunoglobulin molecule such as to permit specific interaction between said molecule and an antigen. The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof. Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Fragments of antibodies include, but are not limited to, Fab (e.g., by papain digestion), F(ab')2 (e.g., by pepsin digestion), Fab' (e.g., by pepsin digestion and partial reduction) and Fv or scFv (e.g., by molecular biology techniques) fragments.

A Fab fragment can be obtained by treating an antibody with the protease papaine. Also, the Fab may be produced by inserting DNA encoding a Fab of the antibody into a vector for prokaryotic expression system or for eukaryotic expression system, and introducing the vector into a prokaryote or eukaryote to express the Fab. A F(ab')2 may be obtained by treating an antibody with the protease pepsin. Also, the F(ab')2 can be produced by binding a Fab' via a thioether bond or a disulfide bond. A Fab may be obtained by treating F(ab')2 with a reducing agent, e.g., dithiothreitol. Also, a Fab' can be produced by inserting DNA encoding a Fab' fragment of the antibody into an expression vector for a prokaryote or an expression vector for a eukaryote, and introducing the vector into a prokaryote or eukaryote for its expression. A Fv fragment may be produced by restricted cleavage by pepsin, e.g., at 4° C. and pH 4.0. (a method called "cold pepsin digestion"). The Fv fragment consists of the heavy chain variable domain (VH) and the light chain variable domain (VL) held together by strong noncovalent interaction. A scFv fragment may be produced by obtaining cDNA encoding the VH and VL domains as previously described, constructing DNA encoding scFv, inserting the DNA into an expression vector for prokaryote or an expression vector for eukaryote, and then introducing the expression vector into a prokaryote or eukaryote to express the scFv.

In general, antibodies can usually be raised to any antigen, using the many conventional techniques now well known in the art. Any targeting antibody to an antigen which is found in sufficient concentration at a site in the body of a mammal which is of diagnostic or therapeutic interest can be used to make the compounds provided herein.

As used herein, the term "conjugated" refers to when one molecule or agent is physically or chemically coupled or adhered to another molecule or agent. Examples of conjugation include covalent linkage and electrostatic complexation. The terms "complexed," "complexed with," and "conjugated" are used interchangeably herein.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As a result of the selection of substituents and substituent patterns, certain of the compounds of the present technology can have asymmetric centers and can occur as mixtures of stereoisomers, or as individual diastereomers, or enantiomers. All isomeric forms of these compounds, whether isolated or in mixtures, are within the scope of the present technology. Pharmaceutically acceptable salts include both the metallic (inorganic) salts and organic salts, a list of which is given in Remington's Pharmaceutical Sciences, 17th Edition, pg. 1418 (1985). It is well known to one skilled in the art that an appropriate salt form is chosen based on physical and chemical properties. As will be understood by those skilled in the art, pharmaceutically acceptable salts include, but are not limited to salts of inorganic acids such as hydrochloride, sulfate, phosphate, diphosphate, hydrobromide, and nitrate; or salts of an organic acid such as malate, maleate, fumarate, tartrate, succinate, citrate, acetate, lactate, methanesulfonate, p-toluenesulfonate or palmoate, salicylate, and stearate. Similarly pharmaceutically acceptable cations include, but are not limited to sodium, potassium, calcium, aluminum, lithium, and ammonium (especially ammonium salts with secondary amines). Also included within the scope of this technology are crystal forms, hydrates, and solvates.

Compositions according to the technology can be administered in the form of pharmaceutically acceptable salts. The term "pharmaceutically acceptable salt" refers to a salt that possesses the effectiveness of the parent compound and is not biologically or otherwise undesirable (e.g., is neither toxic nor otherwise deleterious to the recipient thereof). Suitable salts include acid addition salts that may, for example, be formed by mixing a solution of the compound of the present technology with a solution of a pharmaceutically acceptable acid such as hydrochloric acid, sulfuric acid, acetic acid, trifluoroacetic acid, or benzoic acid. Certain of the compounds employed in the present technology may carry an acidic moiety (e.g., COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (COOH) or alcohol group being present, pharmaceutically acceptable esters can be employed to modify the solubility or hydrolysis characteristics of the compound.

The term "administration" and variants thereof (e.g., "administering" a compound) in reference to a compound mean providing the compound or a prodrug of the compound to the individual in need of treatment or prophylaxis. When a compound of the technology or a prodrug thereof is provided in combination with one or more other active agents, "administration" and its variants are each understood to include provision of the compound or prodrug and other agents at the same time or at different times. When the agents of a combination are administered at the same time, they can be administered together in a single composition or they can be administered separately. As used herein, the term "composition" is intended to encompass a product comprising the specified ingredients in the specified amounts, as well as any product that results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation, or experiment.

The term "effective amount" as used herein means that amount of active compound or pharmaceutical agent that elicits the biological or medicinal response in a cell, tissue, organ, system, animal, or human that is being sought by a researcher, veterinarian, medical doctor, or other clinician. In some embodiments, the effective amount is a "therapeutically effective amount" for the alleviation of the symptoms of the disease or condition being treated. In some embodiments, the effective amount is a "prophylactically effective amount" for prophylaxis of the symptoms of the disease or condition being prevented. The term also includes herein the amount of active compound sufficient to inhibit the mineralocorticoid receptor and thereby elicit a response being sought (e.g., an "inhibition effective amount"). When the active compound is administered as the salt, references to the amount of active ingredient are to the free form (the non-salt form) of the compound. In some embodiments, this amount is between 1 mg and 1000 mg per day, e.g., between 1 mg and 500 mg per day (between 1 mg and 200 mg per day).

In the method of the present technology, compounds, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the technology can, for example, be administered orally, parenterally (including subcutaneous injections, intravenous, intramuscular, intrasternal injection, or infusion techniques), by inhalation spray, or rectally, in the form of a unit dosage of a pharmaceutical composition containing an effective amount of the compound and conventional non-toxic pharmaceutically-acceptable carriers, adjuvants, and vehicles. Liquid preparations suitable for oral administration (e.g., suspensions, syrups, elixirs, and the like) can be prepared according to techniques known in the art and can employ any of the usual media such as water, glycols, oils, alcohols, and the like. Solid preparations suitable for oral administration (e.g., powders, pills, capsules, and tablets) can be prepared according to techniques known in the art and can employ such solid excipients as starches, sugars, kaolin, lubricants, binders, disintegrating agents, and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution, or a solution containing a mixture of saline and glucose. Further description of methods suitable for use in preparing pharmaceutical compositions for use in the present technology and of ingredients suitable for use in said compositions is provided in Remington's Pharmaceutical Sciences, 18th edition, edited by A. R. Gennaro, Mack Publishing Co., 1990. Compounds of the present technology can be made by a variety of methods depicted in the synthetic reaction schemes provided herein. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis, Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The synthetic reaction schemes and examples provided herein are merely illustrative of some methods by which the compounds of the present technology can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Description

The technology described herein relates to nucleotide analogs and related methods, compositions (e.g., reaction mixtures), kits, and systems for manipulating, detecting, isolating, and sequencing nucleic acids. In particular, some embodiments of the nucleotide analogs comprise an alkyne moiety that provides both terminating and linking functionalities. The technology provides advantages over conventional methods such as a lower cost and reduced complexity.

1. Nucleotide Analogs

Provided herein are analogs of nucleotides. In some embodiments, the nucleotide analogs comprise one or more alkyne terminator moieties. For example, in some embodiments the technology provides a 3'-O-blocked nucleotide analog that is a 3'-O-alkynyl nucleotide analog. In some embodiments, the 3'-O-blocked nucleotide analog is a 3'-O-propargyl nucleotide analog having a structure as shown below:

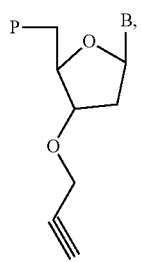

wherein B is the base of the nucleotide, e.g., adenine, guanine, cytosine, thymine, or uracil, e.g., B is one of:

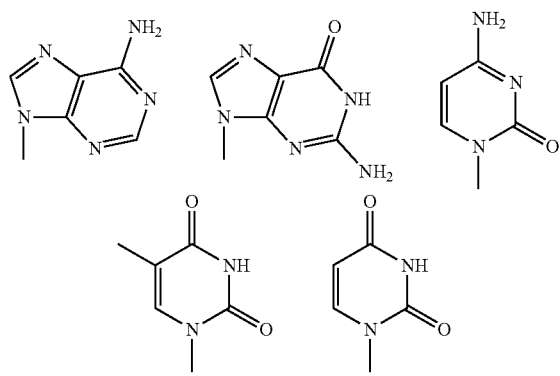

or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc. and wherein P comprises a phosphate moiety (e.g., a monophosphate, a diphosphate, a triphosphate, a tetraphosphate); a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate, as defined herein.

The nucleotide analogs are not limited to a specific phosphate group. In some embodiments, the phosphate group is a monophosphate group or a polyphosphate such as a diphosphate group, a triphosphate group, or a tetraphosphate group. In some embodiments, the phosphate group is a pyrophosphate. In some embodiments, P represents a group comprising a 5' hydroxyl; an alpha thiophosphate (e.g., phosphorothioate or phosphorodithioate), a beta thiophosphate (e.g., phosphorothioate or phosphorodithioate), and/or a gamma thiophosphate (e.g., phosphorothioate or phosphorodithioate); or an alpha methylphosphonate, a beta methylphosphonate, and/or a gamma methylphosphonate.

Moreover, the base of the nucleotide analogs is not limited to a specific base. In some embodiments, the base is an adenine, cytosine, guanine, thymine, uracil, and analogs thereof such as, for example, acyclic bases. The nucleotide analogs are not limited to a specific sugar moiety. In some embodiments, said sugar moiety is a ribose, deoxyribose, dideoxyribose, and analogs, derivatives, and/or modifications thereof (e.g., a thiofuranose, thioribose, thiodeoxyribose, etc.). In some embodiments, the sugar moiety is an arabinose or other related carbohydrate.

In some embodiments, the nucleotide analog is a 3'-O-propargyl-dNTP where N is selected from the group consisting of A, C, G, T and U. In some embodiments, the nucleotide analogs comprise detectable labels or tags such as an optically detectable moiety (e.g., a fluorescent dye), electrochemically detectable moieties (e.g., a redox active group), a quantum dot, a chromogen, a biological image contrast agent, a drug delivery vehicle tag, etc.

The synthesis of compounds provided herein is performed as described in, e.g., Bentley et al. (2008) "Accurate whole genome sequencing using reversible terminator chemistry" Nature 456(7218): 53-9 and Ju et al. (2006) "Four Color DNA Sequencing by synthesis using cleavable fluorescent nucleotide reversible terminators," PNAS 103(52): 19635-40, incorporated herein by reference, with the modifications as needed to provide the various nucleotide analogs described herein. Additionally, various molecular characterizations such as NMR, mass spectrometry, and chromatography/affinity analysis are used in some embodiments to confirm successful synthesis of the correct compounds.

In some embodiments, synthetic methods for compounds encompassed and contemplated by the technology described herein comprise one or more of the following synthetic schemes or modifications thereof:

Synthesis of 3'-O-propargyl dCTP

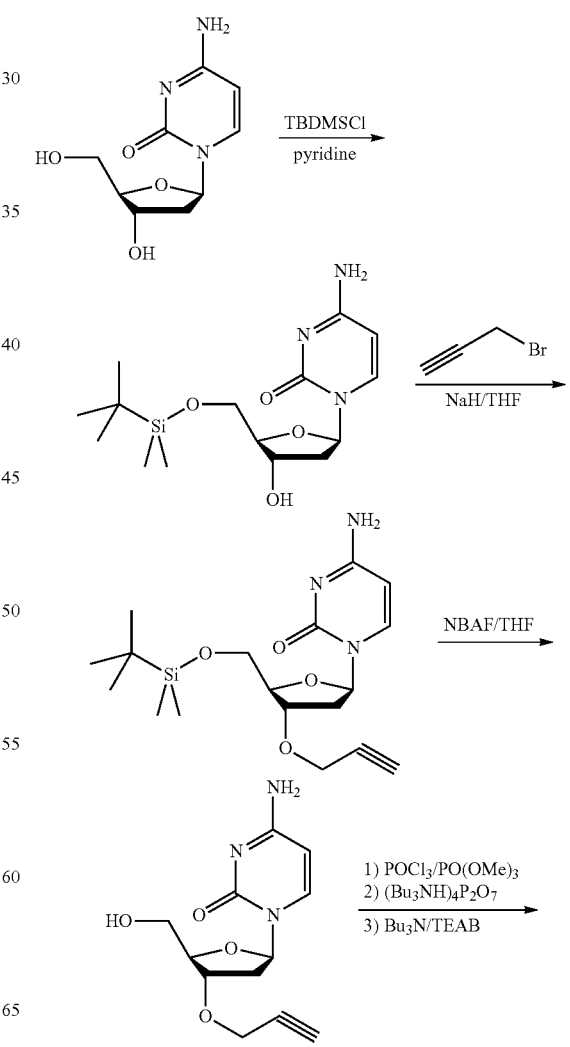

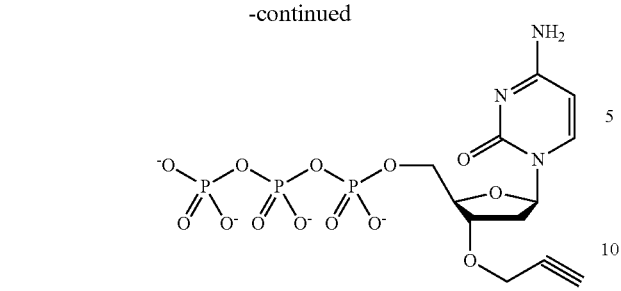
Synthesis of 3'-O-propargyl dTTP
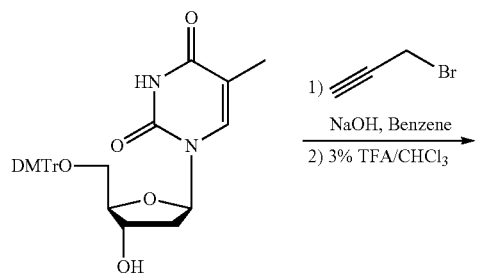
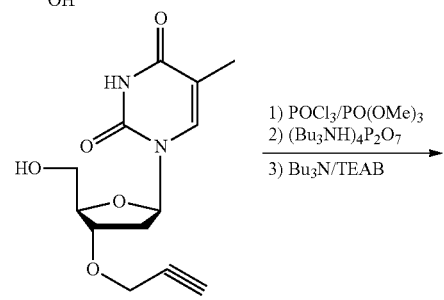
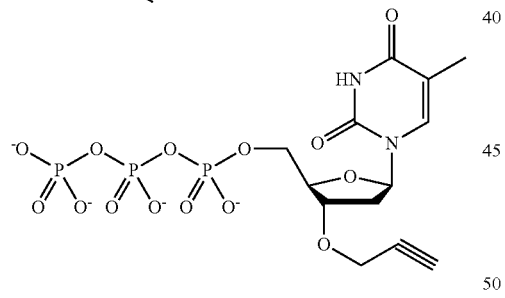
Synthesis of 3'-O-propargyl dATP
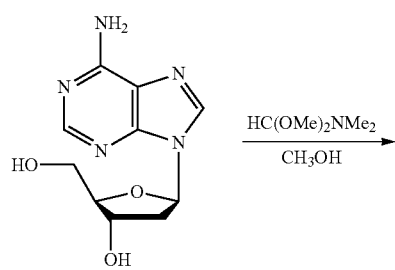
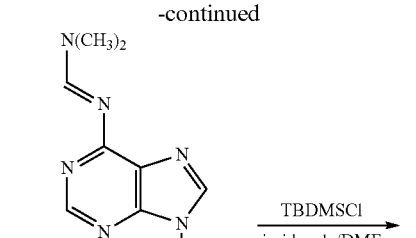
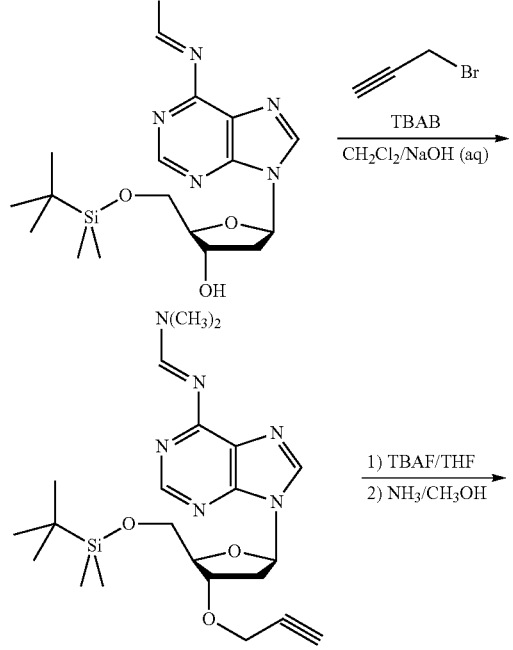
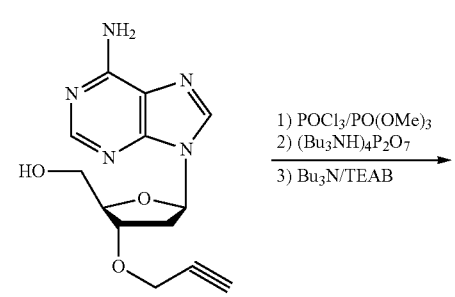
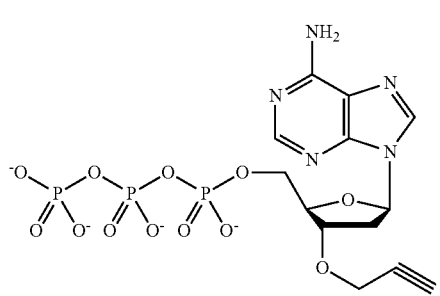

Synthesis of 3'-O-propargyl dGTP

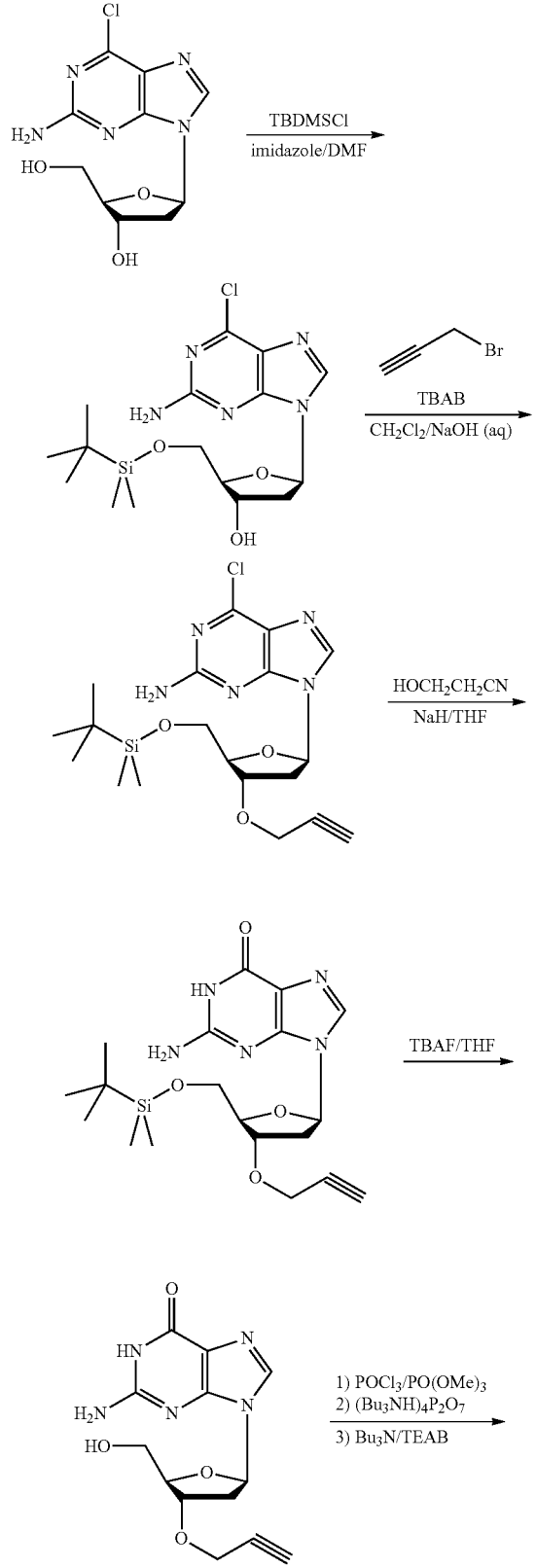

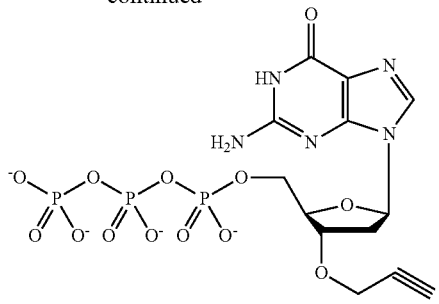

In some embodiments, the nucleotide analogs are used to incorporate alkyne moieties into nucleic acid polymers, e.g., by a polymerase. In some embodiments, a polymerase is modified to enhance incorporation of the nucleotide analogs disclosed herein. Exemplary modified polymerases are disclosed in U.S. Pat. Nos. 4,889,818; 5,374,553; 5,420,029; 5,455,170; 5,466,591; 5,618,711; 5,624,833; 5,674,738; 5,789,224; 5,795,762; 5,939,292; and U.S. Patent Publication Nos. 2002/0012970 and 2004/0005599. A non-limiting example of a modified polymerase includes G46E E678G CS5 DNA polymerase, G46E E678G CS5 DNA polymerase, E615G Taq DNA polymerase, ΔZO5R polymerase, and G46E L329A E678G CS5 DNA polymerase disclosed in U.S. Patent Publication No. 2005/0037398. In some embodiments, the polymerase is a *Thermococcus* sp. 9∘N-7 polymerase sold under the trade name THERMINATOR (e.g., THERMINATOR II) by New England BioLabs (Ipswich, Mass.). The production of modified polymerases can be accomplished using many conventional techniques in molecular biology and recombinant DNA described herein and known in the art. In some embodiments, polymerase mutants, such as those described in U.S. Pat. No. 5,939,292, which incorporate NTPs as well as dNTPs are used.

In some embodiments the nucleotide analogs contain tags in addition to alkyne moieties (see supra). In some embodiments, nucleotide analogs with 3' alkyne moieties are used to terminate a polymerase reaction. Chemical tags containing an azido moiety can then be appended to the nucleic acid polymer through click chemistry. In some embodiments, the reaction of the terminator alkyne compound with the azido moiety-containing compound forms a triazole compound. In some embodiments, the triazole compound functions as a nucleic acid backbone and further enzymatic reactions such as PCR are performed on the triazole compound.

2. Oligonucleotides

In some embodiments, the nucleotide analogs find use for the synthesis of triazole-backbone-modified nucleic acids (e.g., oligonucleotide analogs). For example, the nucleotide analogs find use in methods for aqueous, solid-phase oligonucleotide synthesis. Such methods thus obviate the need for, inter alia, use of organic solvents, deprotection steps, and capping steps in some conventional syntheses; in addition, aqueous methods minimize or eliminate the undesired oxidation of phosphorous in the synthesized compounds, e.g., during cycle synthesis. It is contemplated that an advantage of aqueous-phase synthesis is that it is more rapid than conventional organic-phase synthesis techniques.

In some embodiments are provided a triazole-backbone-modified oligonucleotide comprising nucleotide analogs provided herein. That is, the nucleotide analogs described herein find use in the synthesis of modified oligonucleotides comprising one or more nucleotide analogs and comprising triazole groups in the molecular backbone. In some embodiments, oligonucleotides comprise some conventional nucleotides and some nucleotide analogs in various proportions. In some embodiments, oligonucleotides comprise only nucleotide analogs and do not comprise conventional nucleotides.

Accordingly, in some embodiments are provided a nucleotide analog as described elsewhere herein, e.g., having a structure according to:

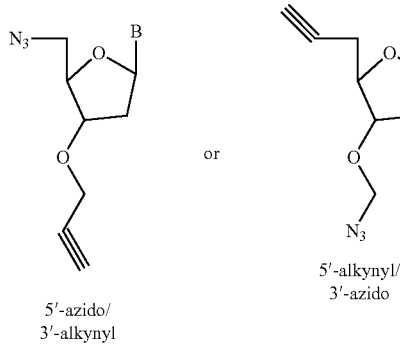

5'-azido/
3'-alkynyl or

5'-alkynyl/
3'-azido where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

Such nucleotide analogs and variants and modified derivatives thereof (e.g., comprising a base analog or alternative sugar as described herein) provide a directional, bi-functional nucleotide analog (e.g., a directional, bi-functional polymerization agent), e.g., for the synthesis of an oligonucleotide (e.g., an oligonucleotide analog, e.g., an oligonucleotide comprising a nucleotide analog described herein). In some embodiments, the directional, bi-functional nucleotide analog provides for synthesis of an oligonucleotide in a 5' to 3' direction and in some embodiments the directional, bi-functional nucleotide analog provides for synthesis of an oligonucleotide in a 3' to 5' direction. In some embodiments, the synthesis of the oligonucleotide comprises use of propargyl moiety and a linker attached to a solid support (e.g., a linker (e.g., a carboxylate linker) that is cleavable under acidic (e.g., mildly acidic) conditions). In some embodiments, the synthesis of the oligonucleotide comprises use of a propargyl moiety and an azide linker attached to a solid support. In some embodiments, a 3'-thio-modified propargyl moiety is linked to the solid support and is cleaved with a reagent comprising silver nitrate or mercuric chloride. In some embodiments, the solid support comprises a controlled pore glass, silica, sephadex, agarose, acrylamide, latex, or polystyrene, etc., provided, in some embodiments, as microspheres. Representative synthetic schemes for producing oligonucleotides are provided as follows:

a. 3' to 5' Oligonucleotide Synthesis Using 3'-Alkynyl/5'-Azido Nucleotide Analog

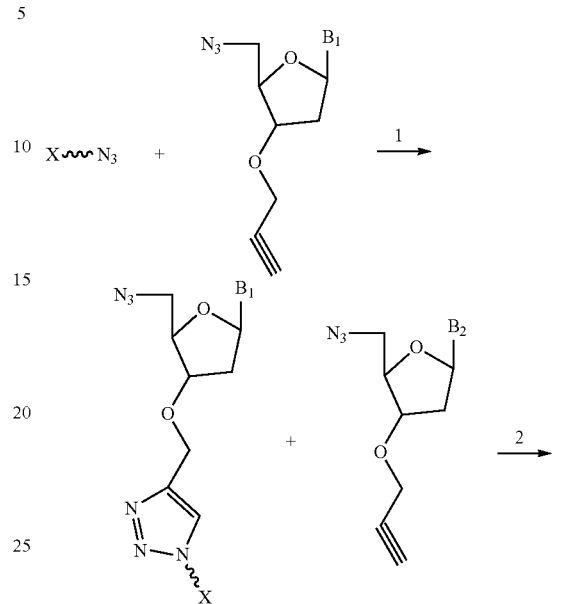

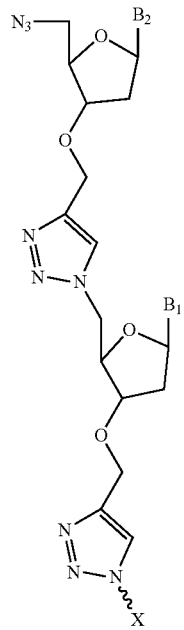

In exemplary synthetic scheme a, X is a solid support, the wavy line (~) is a cleavable linker, $B_1$ is a first nucleotide base, and $B_2$ is a second nucleotide base that may be the same or different than $B_1$. The first step (1) links the first nucleotide analog to the solid support (e.g., using a click chemistry reaction, e.g., using a copper-based catalyst). Then, one or more (e.g., multiple) rounds of the second step (2) (e.g., using a click chemistry reaction, e.g., using a copper-based catalyst) result in synthesis of the oligonucleotide analog, with each step adding another nucleotide analog to the growing polymer chain.

b. 5' to 3' Oligonucleotide Synthesis Using 3'-Alkynyl/5'-Azido Nucleotide Analog

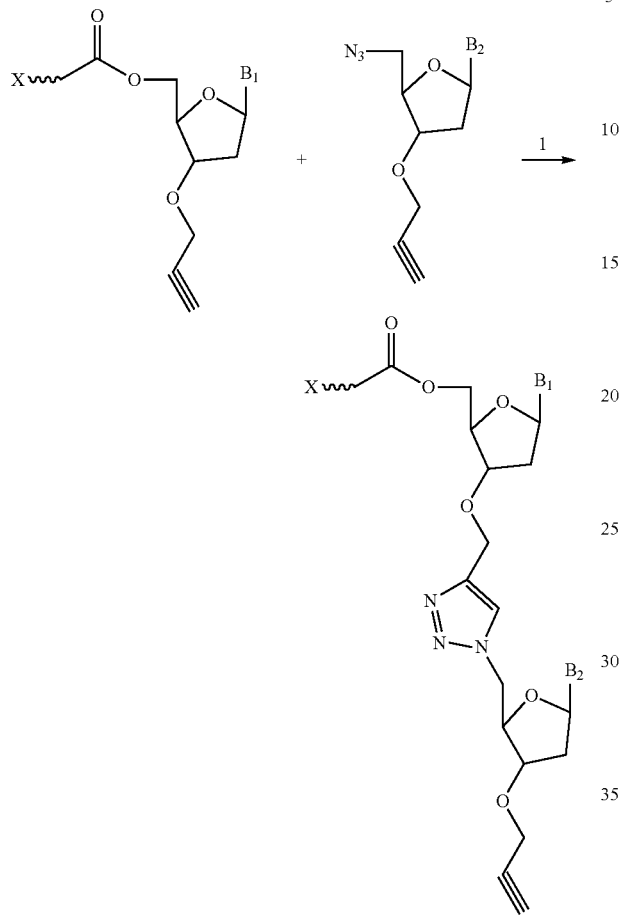

In exemplary synthetic scheme b, X is a solid support, the wavy line (~) is a cleavable linker (e.g., a carboxylate linker), $B_1$ is a first nucleotide base, and $B_2$ is a second nucleotide base that may be the same or different than $B_1$. After reacting the first nucleotide analog with the solid support comprising a linker and reactive carboxylate moiety (e.g., to form an ester link), one or more (e.g., multiple) rounds of nucleotide addition and reaction (1) (e.g., using a click chemistry reaction, e.g., using a copper-based catalyst) result in synthesis of the oligonucleotide analog, with each step adding another nucleotide analog to the growing polymer chain.

c. 5' to 3' Oligonucleotide Synthesis Using 3'-Azido/5'-Alkynyl Nucleotide Analog

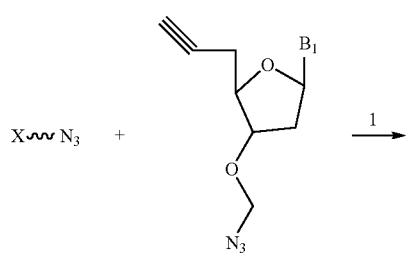

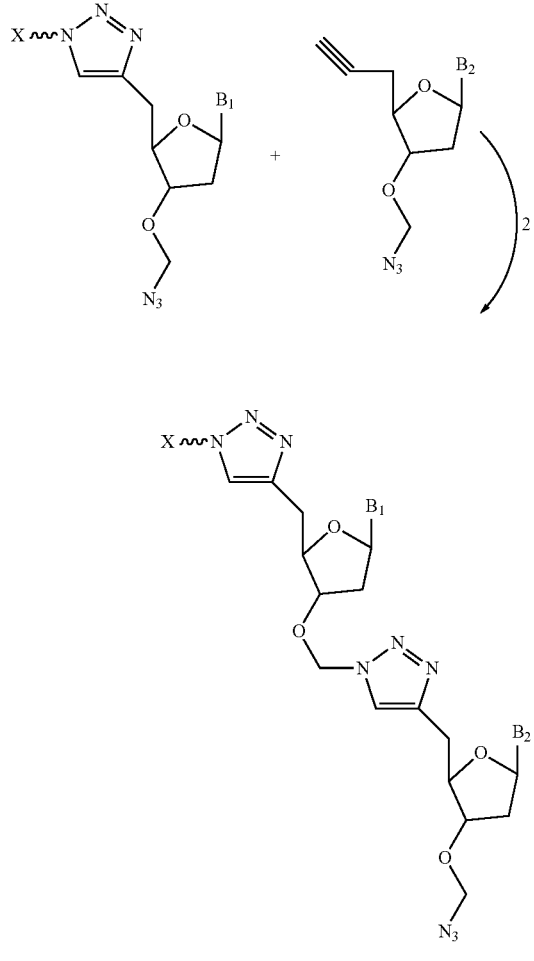

In exemplary synthetic scheme c, X is a solid support, the wavy line (~) is a cleavable linker, $B_1$ is a first nucleotide base, and $B_2$ is a second nucleotide base that may be the same or different than $B_1$. The first step (1) links the first nucleotide analog to the solid support (e.g., using a click chemistry reaction, e.g., using a copper-based catalyst). Then, one or more (e.g., multiple) rounds of the second step (2) (e.g., using a click chemistry reaction, e.g., using a copper-based catalyst) result in synthesis of the oligonucleotide analog, with each step adding another nucleotide analog to the growing polymer chain.

d. 3' to 5' Oligonucleotide Synthesis Using 3'-Azido/5'-Alkynyl Nucleotide Analog

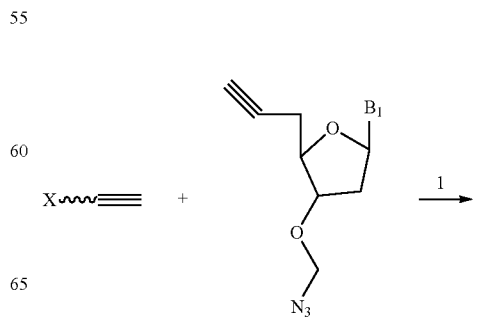

-continued

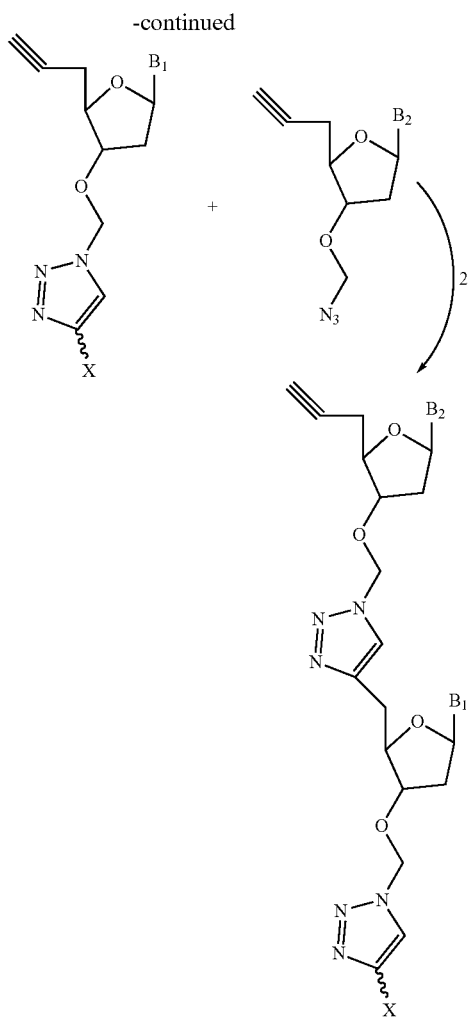

In exemplary synthetic scheme d, X is a solid support, the wavy line (~) is a cleavable linker, $B_1$ is a first nucleotide base, and $B_2$ is a second nucleotide base that may be the same or different than $B_1$. The first step (1) links the first nucleotide analog to the solid support (e.g., using a click chemistry reaction, e.g., using a copper-based catalyst). Then, one or more (e.g., multiple) rounds of the second step (2) (e.g., using a click chemistry reaction, e.g., using a copper-based catalyst) result in synthesis of the oligonucleotide analog, with each step adding another nucleotide analog to the growing polymer chain.

In some embodiments, the oligonucleotide and/or nucleotide analog is reacted with a linker to attach the oligonucleotide and/or nucleotide analog to a solid support, e.g., a bead, a planar surface (an array), a column, etc. The term "solid support" as used herein refers to a material or group of materials having a rigid or semi-rigid surface or surfaces. In many embodiments, at least one surface of the solid support is substantially flat, although in some embodiments it may be desirable to separate regions of the solid support with, for example, wells, raised regions, pins, etched trenches, or the like. According to other embodiments, the solid support takes the form of beads, resins, gels, microspheres, or other geometric configurations. See, e.g., U.S. Pat. No. 5,744,305 and U.S. Pat. Pub. Nos. 20090149340 and 20080038559 for exemplary substrates. In some embodiments, the linker is a cleavable linker (e.g., cleavable by light, heat, chemical, or biochemical reaction).

In exemplary synthesis schemes a, b, c, and d, embodiments of methods for synthesizing an oligonucleotide comprise one or more additional steps of adding a nucleotide analog, reacting a nucleotide analog, washing away and/or otherwise removing an unincorporated nucleotide analog (e.g., after a synthesis step), cleaving a linker, isolating a synthesized oligonucleotide, purifying a synthesized oligonucleotide, and/or adding a tag or a label to the synthesized oligonucleotide.

3. Tagging and Labeling

Nucleic acid detection methodologies serve a critical role in the field of molecular diagnostics. The ability to manipulate biomolecules specifically and efficiently has been the core driving force behind many successful nucleic acid detection technologies. Among the many molecular biology techniques, the ability to label or "tag" a biomolecule of interest has been a key technology for subsequent detection and identification of the biomolecule.

Accordingly, in some embodiments the technology provides compositions, methods, systems, and kits related to tagging of biomolecules such as nucleic acids and/or nucleotides. In some embodiments, alkyne-containing nucleotides such as 3'-O-propargyl-modified nucleotides (e.g., 3'-O-propargyl dNTPs) are incorporated into a nucleic acid in a polymerase extension reaction. In some embodiments, the nucleotide analog halts the polymerase reaction. In some embodiments, the alkyne-containing nucleotide is used (e.g., without further processing and/or purification) in a tagging reaction with an azide-modified tag or labeling reagent using chemical ligation (e.g., a click chemistry reaction). The covalent linkage created using this chemistry mimics natural nucleic acid phosphodiester bonds, thus providing a conjugated product that is suitable for use in subsequent enzymatic reactions such as a polymerase chain reaction.

Labels and tags are compounds, structures, or elements that are amenable to at least one method of detection and/or isolation that allows for discrimination between different labels and/or tags. For example, labels and/or tags comprise semiconductor nanocrystals, metal compounds, peptides, antibodies, small molecules, isotopes, particles, or structures having different shapes, colors, barcodes, or diffraction patterns associated therewith or embedded therein, strings of numbers, random fragments of proteins or nucleic acids, or different isotopes.

The term "label" or "tag" are used interchangeably herein to refer to any chemical moiety attached to a nucleotide or nucleic acid, wherein the attachment may be covalent or non-covalent. Preferably, the label is detectable and renders the nucleotide or nucleic acid detectable to the practitioner of the technology. Exemplary detectable labels that find use with the technology provided herein include, for example, a fluorescent label, a chemiluminescent label, a quencher, a radioactive label, biotin, and gold, or combinations thereof. Detectable labels include luminescent molecules, fluorochromes, fluorescent quenching agents, colored molecules (e.g., chromogens used for in situ hybridization (ISH, FISH) and bright field imaging applications), radioisotopes, or scintillants. Detectable labels also include any useful linker molecule (such as biotin, avidin, digoxigenin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase, and luciferase), electron donors/acceptors, acridinium esters, dyes, and calorimetric substrates. It is also envisioned that a change in mass may be considered a detectable label, e.g., as finds use in surface plasmon resonance detection.

The technology also finds use in applications such as linking DNA-containing alkynes to an image contrast agent (e.g., meglumines, ferumoxsil, ferumoxides, gadodiamide, gadoversetamide, gallium compounds, indium compounds, thallium compounds, rubidium compounds, technetium compounds, iopamidol, etc.), e.g., for biomedical imaging (e.g., magnetic resonance imaging (MRI), computed tomography (CT) scanning, X-ray, etc.), coupling DNA to oligo and/or antisense drug-delivery vehicle tags (e.g., steroids, lipids, cholesterol, vitamins, hormones, carbohydrates, and/or receptor-specific ligands (e.g., folate, nicotinamide, acetylcholine, GABA, glutamate, serotonin, etc.), and coupling to chromogen moieties for in situ hybridization applications. The skilled artisan would readily recognize useful detectable labels that are not mentioned above, which may be employed in the operation of the present invention.

As such, the technology is not limited in the label or tag that is linked to the nucleic acid, e.g., by use of an azide labeling reagent in a click chemistry reaction. Thus, in some embodiments, the label comprises a fluorescently detectable moiety that is based on a dye, wherein the dye is a xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, a fluorescent semiconductor crystal, or a squaraine dye. In some embodiments, the tag or label comprises a radioisotope, a spin label, a quantum dot, or a bioluminescent moiety. In some embodiments, the label is a fluorescently detectable moiety as described in, e.g., Haugland (September 2005) MOLECULAR PROBES HANDBOOK OF FLUORESCENT PROBES AND RESEARCH CHEMICALS (10th ed.), which is herein incorporated by reference in its entirety.

In some embodiments the label (e.g., a fluorescently detectable label) is one available from ATTO-TEC GmbH (Am Eichenhang 50, 57076 Siegen, Germany), e.g., as described in U.S. Pat. Appl. Pub. Nos. 20110223677, 20110190486, 20110172420, 20060179585, and 20030003486; and in U.S. Pat. No. 7,935,822, all of which are incorporated herein by reference.

In some embodiments, the nucleic acid and/or nucleotide comprising a modified nucleotide, e.g., comprising an alkyne group, is tagged with a moiety that provides for detection and/or isolation of the nucleic acid and/or nucleotide by specific interaction with a second moiety. For example, in some embodiments, the nucleic acid and/or nucleotide is linked (e.g., by a click chemistry reaction) to a tag comprising an azide and a biotin moiety, an epitope, an antigen, an aptamer, an affinity tag, a histidine tag, a barcode oligonucleotide, a poly-A tail, a capture oligonucleotide, a protein, a sugar, a chelator, a mass tag (e.g., 2-nitro-methylbenzyl group, a 2-nitro-methyl-3-fluorobenzyl group, a 2-nitro-α-methyl-3,4-difluorobenzyl group, a 2-nitro-α-methyl-3,4-dimethoxybenzyl group, a 2-nitro-α-methyl-benzyl group, a 2-nitro-α-methyl-3-fluorobenzyl group, a 2-nitro-methyl-3,4-difluorobenzyl group, a 2-nitro-α-methyl-3,4-dimethoxybenzyl), a charge tag.

In some embodiments, the nucleic acid and/or nucleotide comprising an alkyne is reacted with a linker comprising an azide to attach the nucleic acid and/or nucleotide to a solid support, e.g., a bead, a planar surface (an array), a column, etc. In some embodiments, the linker is a cleavable linker (e.g., cleavable by light, heat, chemical, or biochemical reaction).

4. Reactions

In some embodiments, the technology finds use in linking an oligonucleotide to a nucleic acid (e.g., a DNA, an RNA). For example, in some embodiments, a nucleic acid comprising a nucleotide analog (e.g., a nucleic acid comprising an alkyne group, e.g., a 3'-O-propargyl nucleotide, e.g., a 3'-O-propargyl dNTP) is linked to an oligonucleotide comprising a group (e.g., an azide group) that is chemically reactive with the chemical moiety of the nucleotide analog, e.g., by a click chemistry reaction. In some embodiments, the oligonucleotide is single-stranded and in some embodiments the oligonucleotide is double-stranded. In some embodiments the nucleic acid is a DNA and in some embodiments the nucleic acid is an RNA; in some embodiments the oligonucleotide is a DNA and in some embodiments the oligonucleotide is an RNA.

In some embodiments, methods of the technology involve attaching an adaptor to a nucleic acid. In some embodiments an adaptor comprises a functional moiety for chemical ligation to a nucleotide analog. For example, in some embodiments an adaptor comprises an azide group (e.g., at the 5' end) that is reactive with an alkynyl group (e.g., a propargyl group, e.g., at the 3' end of a nucleic acid comprising the nucleotide analog), e.g., by a click chemistry reaction (e.g., using a copper (e.g., a copper-based) catalyst reagent).

In some embodiments the alkyne is a butargyl group or a structural derivative thereof. In some embodiments the alkyne comprises a sulfur atom, e.g., to provide a thioalkynyl, a thio-propargyl (e.g. 3'-S-propargyl) group, or a structural derivative thereof. In some embodiments, the adaptors comprise a universal sequence and/or an index, e.g., a barcode nucleotide sequence. Additionally, adaptors can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adaptors or subsets of different adaptors (e.g., a universal sequence), one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adaptors comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adaptor oligonucleotide. When an adaptor oligonucleotide is capable of forming secondary structure, such as a hairpin, sequence elements can be located partially or completely outside the secondary structure, partially or completely inside the secondary structure, or in between sequences participating in the secondary structure. For example, when an adaptor oligonucleotide comprises a hairpin structure, sequence elements can be located partially or completely inside or outside the hybridizable sequences (the "stem"), including in the sequence between the hybridizable sequences (the "loop"). In some embodiments, the adaptor oligonucleotides in a plurality of adaptor oligonucleotides having different barcode sequences comprise a sequence element common among all adaptor oligonucleotides in the plurality. A difference in sequence elements can be any such that at least a portion of different adaptors do not completely align, for example, due to changes in sequence length, deletion or insertion of one or more nucleotides, or a change in the nucleotide composition at one or more nucleotide positions (such as a base change or base modification). In some embodiments, an adaptor oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adaptors with complementary overhangs comprising the random sequence. In some embodiments, an adaptor overhang is complementary to a target polynucleotide overhang produced by restriction endonuclease digestion. In some embodiments, an adaptor overhang consists of an adenine or a thymine.

In some embodiments, the adaptor sequences contain a molecular binding site identification element to facilitate identification and isolation of the target nucleic acid for downstream applications. Molecular binding as an affinity mechanism allows for the interaction between two molecules to result in a stable association complex. Molecules that can participate in molecular binding reactions include proteins, nucleic acids, carbohydrates, lipids, and small organic molecules such as ligands, peptides, or drugs.

When a nucleic acid molecular binding site is used as part of the adaptor, it can be used to employ selective hybridization to isolate a target sequence. Selective hybridization may restrict substantial hybridization to target nucleic acids containing the adaptor with the molecular binding site and capture nucleic acids, which are sufficiently complementary to the molecular binding site. Thus, through "selective hybridization" one can detect the presence of the target polynucleotide in an impure sample containing a pool of many nucleic acids. An example of a nucleotide-nucleotide selective hybridization isolation system comprises a system with several capture nucleotides, which are complementary sequences to the molecular binding identification elements, and are optionally immobilized to a solid support. In other embodiments, the capture polynucleotides are complementary to the target sequences itself or a barcode or unique tag contained within the adaptor. The capture polynucleotides can be immobilized to various solid supports, such as inside of a well of a plate, mono-dispersed spheres, microarrays, or any other suitable support surface known in the art. The hybridized complementary adaptor polynucleotides attached on the solid support can be isolated by washing away the undesirable non-binding nucleic acids, leaving the desirable target polynucleotides behind. If complementary adaptor molecules are fixed to paramagnetic spheres or similar bead technology for isolation, then spheres can then be mixed in a tube together with the target polynucleotide containing the adaptors. When the adaptor sequences have been hybridized with the complementary sequences fixed to the spheres, undesirable molecules can be washed away while spheres are kept in the tube with a magnet or similar agent. The desired target molecules can be subsequently released by increasing the temperature, changing the pH, or by using any other suitable elution method known in the art.

As described elsewhere herein, a "barcode" or "barcode oligonucleotide" is a known nucleic acid sequence that allows some feature of a nucleic acid with which the barcode is associated to be identified. For example, in some embodiments, the feature of the nucleic acid to be identified is the sample or source from which the nucleic acid is derived. The barcode sequence generally includes certain features that make the sequence useful, e.g., in sequencing reactions. For example, the barcode sequences are designed to have minimal or no homopolymer regions, e.g., 2 or more of the same base in a row such as AA or CCC, within the barcode sequence. In some embodiments, the barcode sequences are also designed so that they are at least one edit distance away from the base addition order when performing a manipulation or molecular biological process, such as base-by-base sequencing, ensuring that the first and last bases do not match the expected bases of the sequence.

In some embodiments, the barcode sequences are designed such that each sequence is correlated to a particular nucleic acid. Methods of designing sets of barcode sequences are shown, for example, in U.S. Pat. No. 6,235,475, the contents of which are incorporated by reference herein in their entirety. In some embodiments, barcode sequences range from about 5 nucleotides to about 15 nucleotides. In a particular embodiment, the barcode sequences range from about 4 nucleotides to about 7 nucleotides. In some embodiments, lengths and sequences of barcode sequences are designed to achieve a desired level of accuracy of determining the identity of a nucleic acid. For example, in some embodiments barcode sequences are designed such that after a tolerable number of point mutations, the identity of the associated nucleic acid is deduced with a desired accuracy. In some embodiments, a Tn-5 transposase (commercially available from Epicentre Biotechnologies; Madison, Wis.) cuts a nucleic acid into fragments and inserts short pieces of DNA into the cuts. The short pieces of DNA are used to incorporate the barcode sequences.

Methods for designing sets of barcode sequences and other methods for attaching adaptors (e.g., comprising barcode sequences) are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

With appropriate changes to reaction schemes, use of 5' alkynyl/3' azido and 5' azido/3' alkynyl nucleotide analogs are contemplated to be interchangeable in reactions with the appropriate reactive substrates for linking to the 5' and/or 3' ends of nucleotide analogs, e.g., by click chemistry.

In some embodiments, the technology finds use in a primer extension reaction (see, e.g., FIG. 1) and/or adaptor ligation (see, e.g., FIG. 1). In particular embodiments, a primer annealed to a template (e.g., a target nucleic acid) is extended by a polymerase, which adds a nucleotide analog to the primer. While FIG. 1 shows the exemplary addition of a G-containing nucleotide analog across from the C base in the template, the primer extension technology is not limited in the bases that are added. Then, in some embodiments, an azide-modified DNA (e.g., an adaptor, e.g., an adaptor comprising a primer binding site and/or a barcode) is ligated to the primer extension product (e.g., by click chemistry). The ligation product comprises a linkage that mimics the conventional nucleic acid backbone, e.g., a triazole, and that is biocompatible with downstream enzymatic and/or chemical reactions, e.g., PCR (e.g., see FIG. 1).

5. Sequencing

In some embodiments, the nucleotide analogs find use in nucleic acid sequencing, e.g., "next generation sequencing" (NGS). For example, DNA sequencing-by-synthesis (SBS) involves determining DNA sequence by detecting certain signals (e.g., pyrophosphate groups) that are generated when a nucleotide is incorporated by a polymerase reaction. Other SBS methods involve alternate means of detecting the polymerase addition of nucleotides such as detection of light emission, change in fluorescence, chance in pH, or some other physical or chemical change. For example, Illumina's reversible terminator sequencing relies upon dye-containing reversible terminator bases. When one such base is added to the growing nucleic acid polymer, the reaction is halted and the dye on the terminal nucleic acid is detectable. The terminator-containing molecule can then be treated with a cleavage enzyme that reverses the termination and allows for the addition of additional nucleotides. This step-wise process is an improvement on earlier technology, but the extra cleavage step and subsequent sample purification leave room for further improvement.

Figure 2:
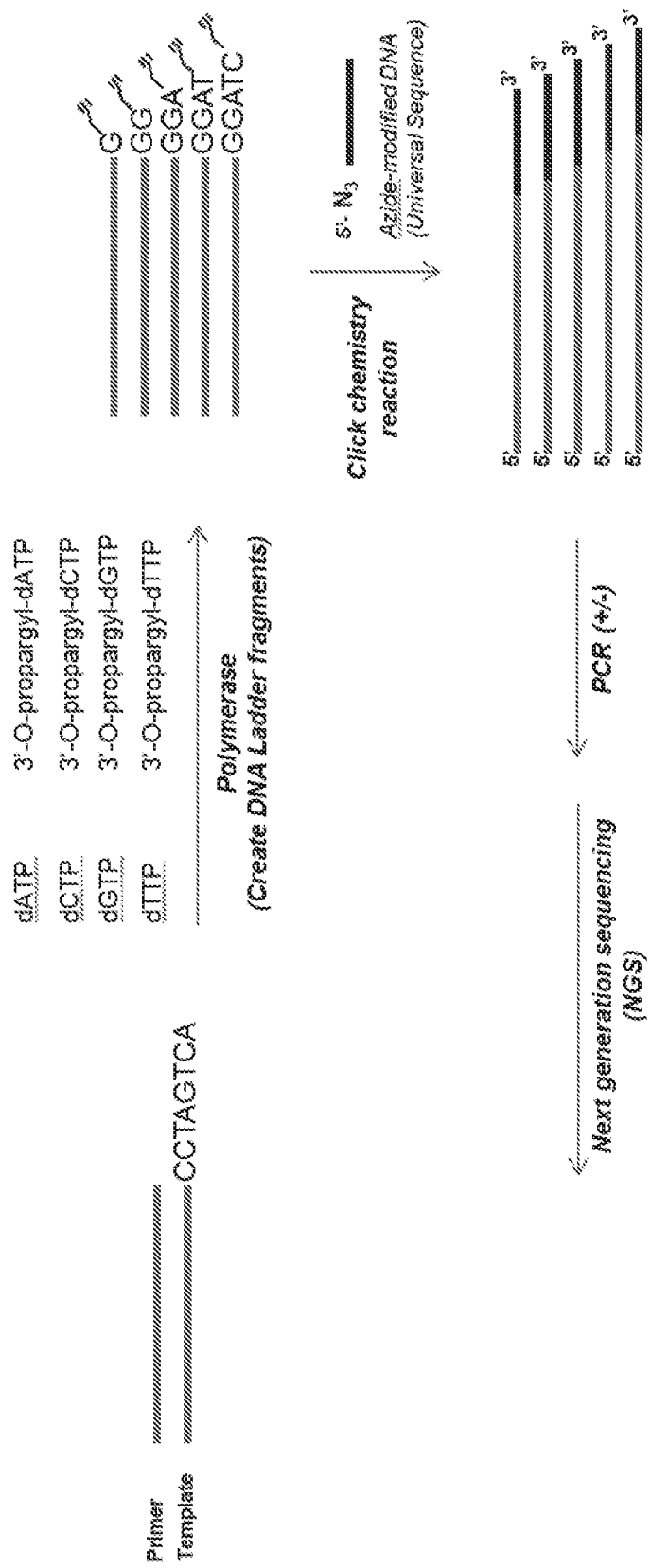
FIG. 2 is a schematic showing a polymerase extension reaction using a combination of dNTPs and 3'-O-propargyl-dNTPs. DNA ladder fragments (n+1 fragments) are generated with each of the fragments' 3'-ends having an alkyne group. These DNA ladder fragments are ligated to a 5'-azide-modified DNA molecule, which has a "universal" sequence and/or a barcode sequence and/or a primer binding site, via click chemistry. The ligated DNA fragments are subsequently treated and used as input in next generation sequencing (NGS) processes. These DNA fragments with the n+1 characteristic produce DNA sequencing data by assembling short reads, thereby significantly decreasing the NGS run time.
Figure 3A:
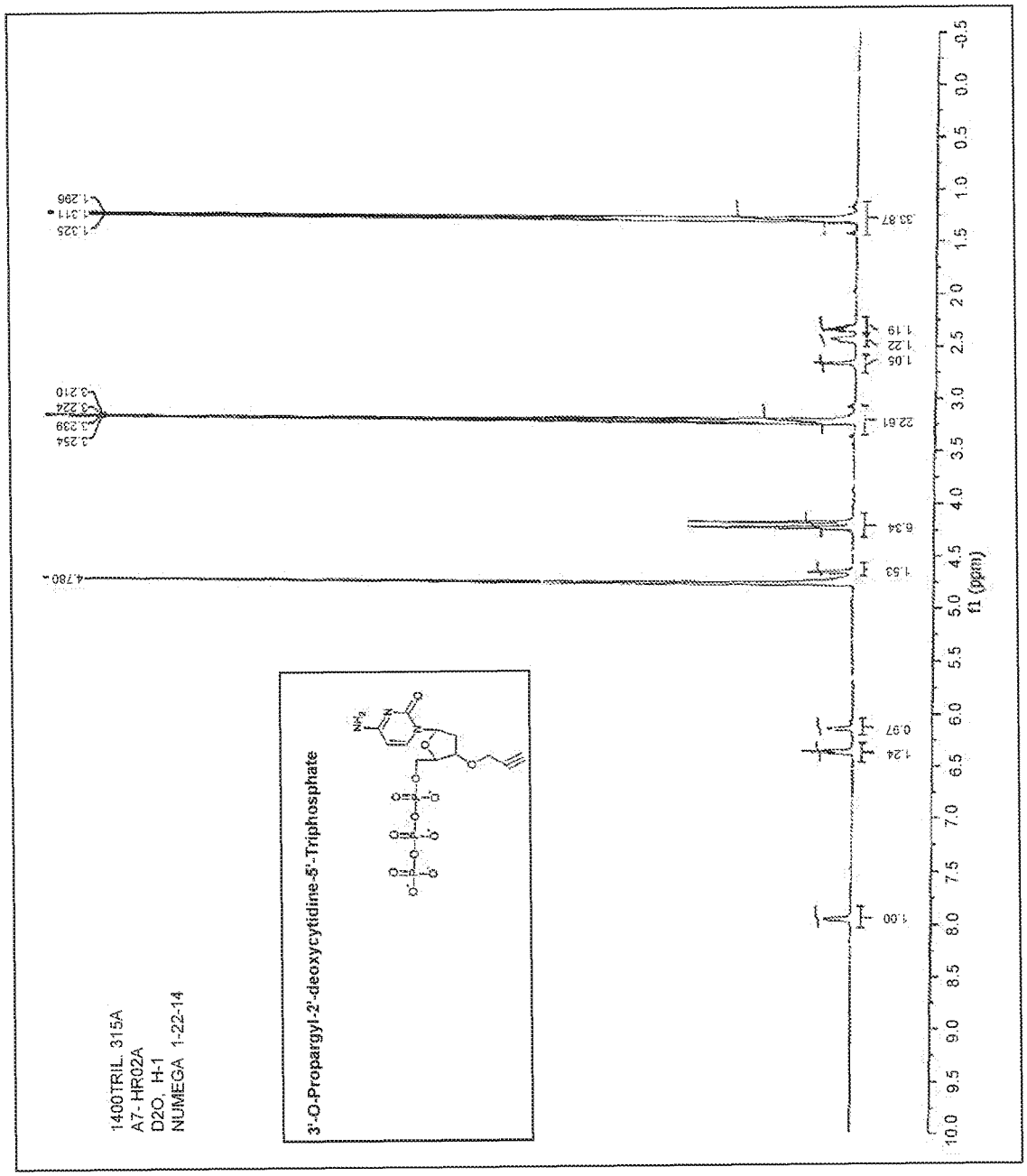
FIG. 3A-3G show analytical data for 3'-O-propargyl-2'-deoxycytidine-5'-triphosphate (3'-O-propargyl-dCTP) synthesized as described herein.
Figure 3B:
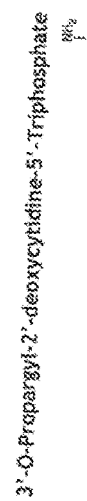
Figure 3B:
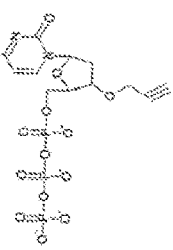
Figure 3B:
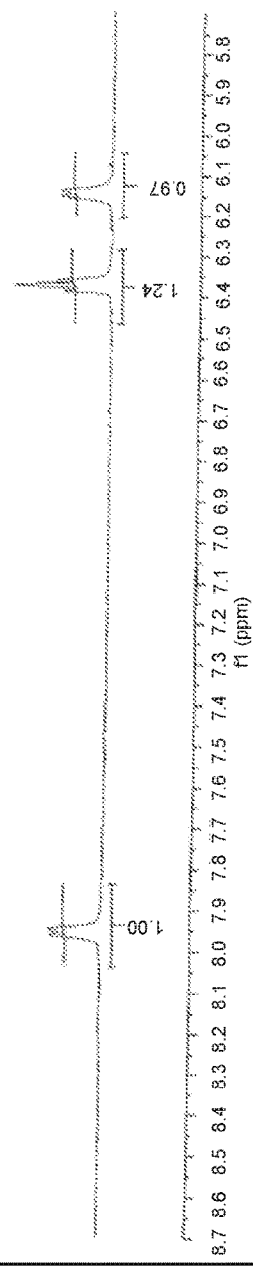
Figure 3C:
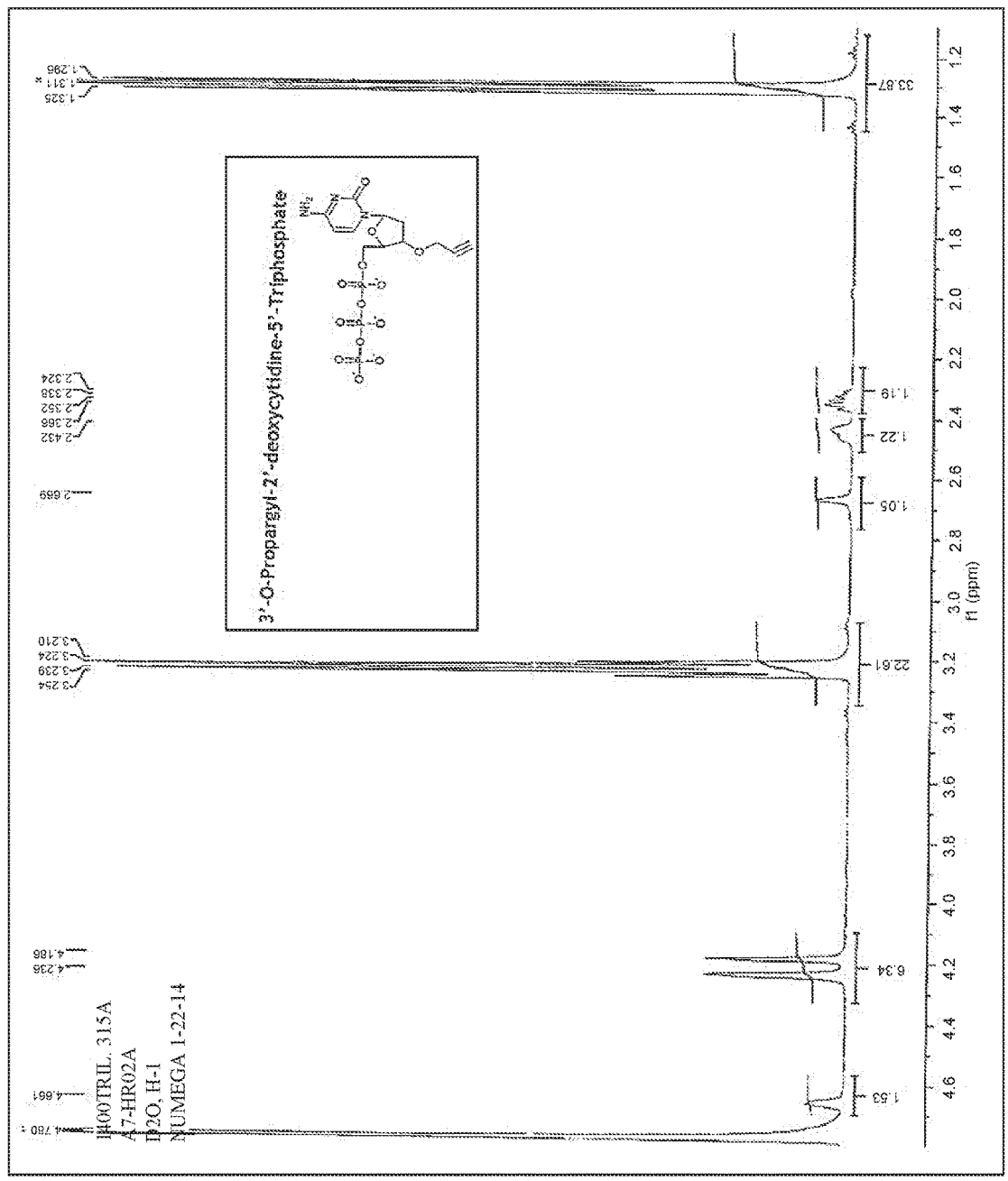
Figure 3D:
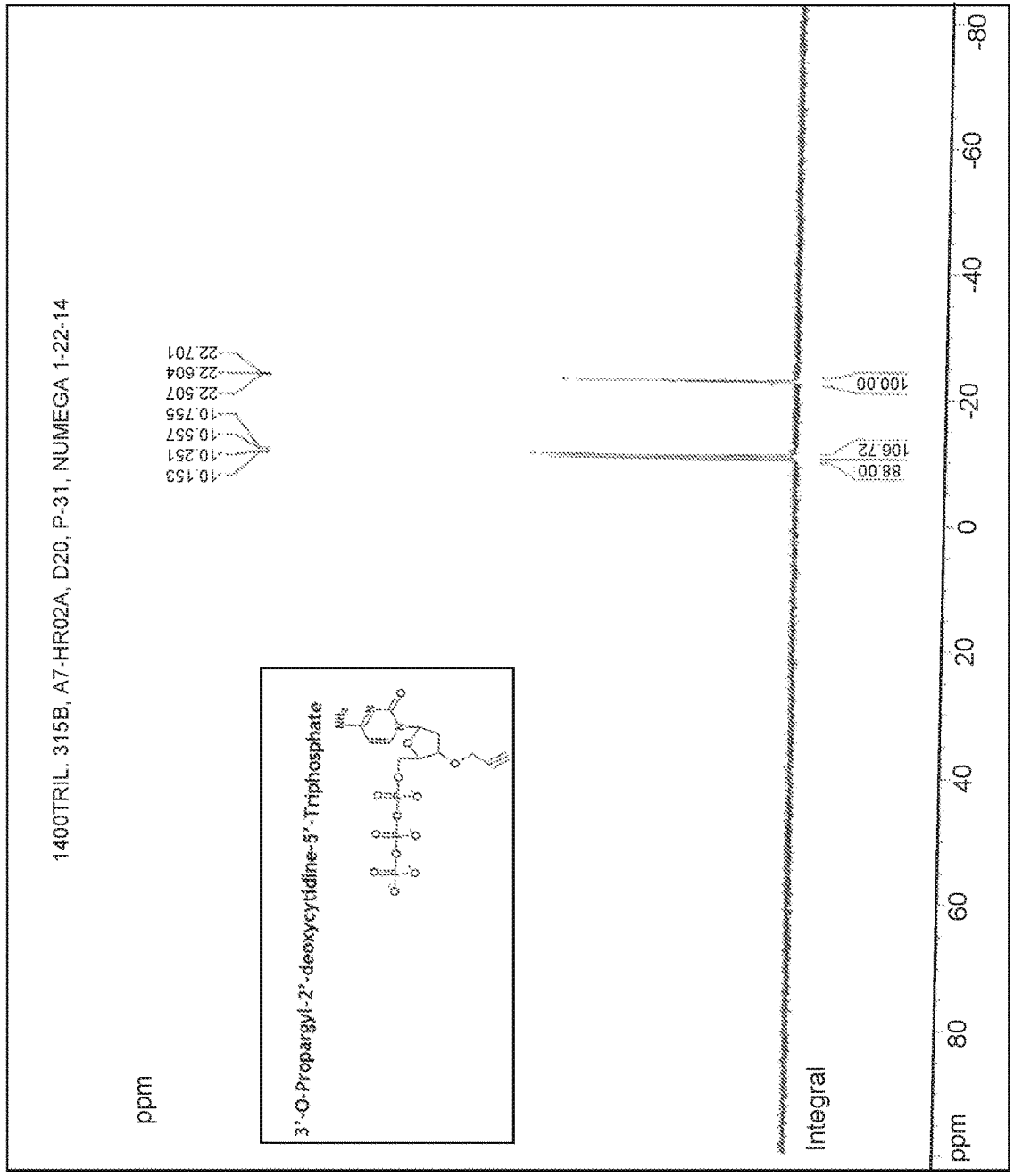
Figure 3E:
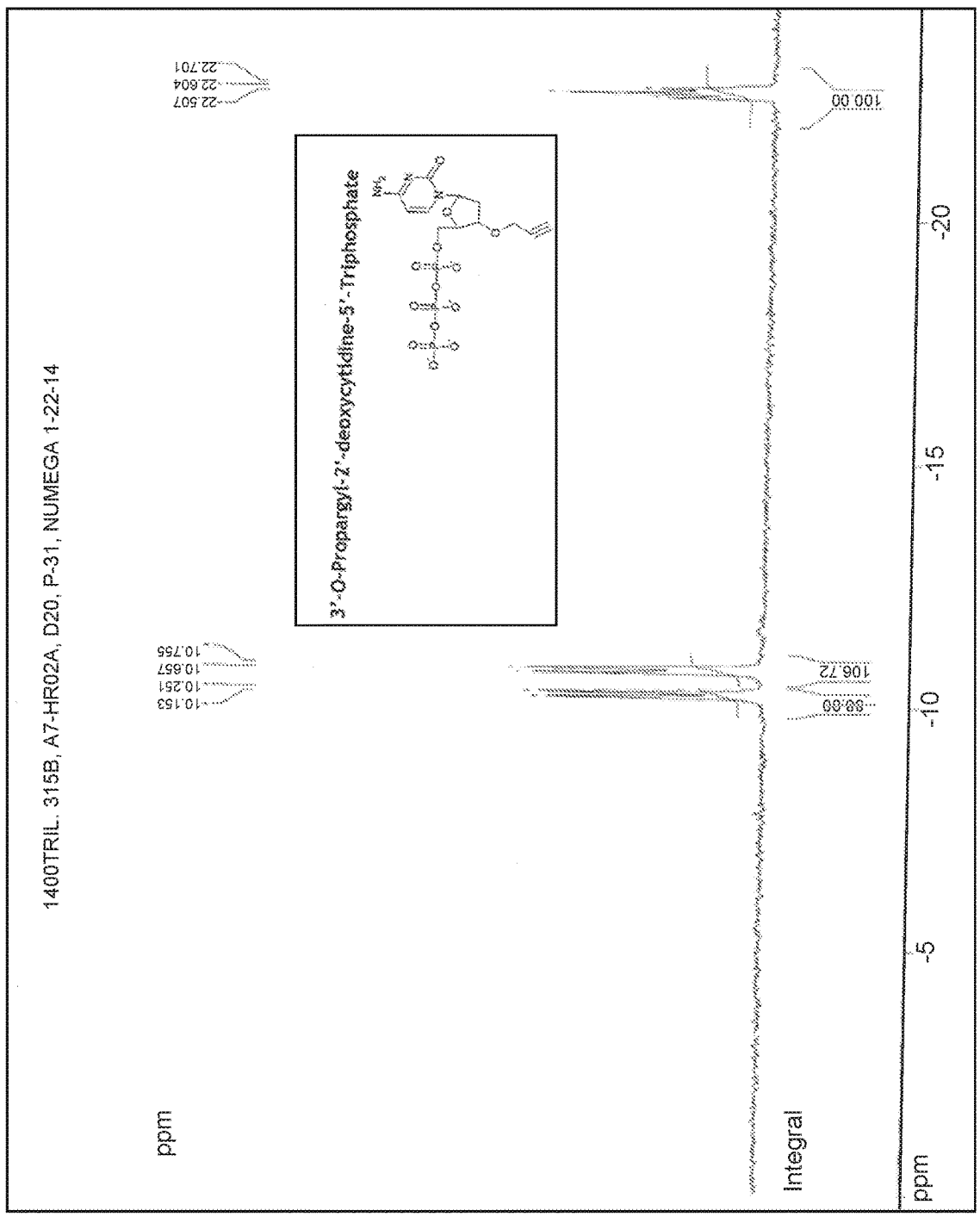
Figure 3F:
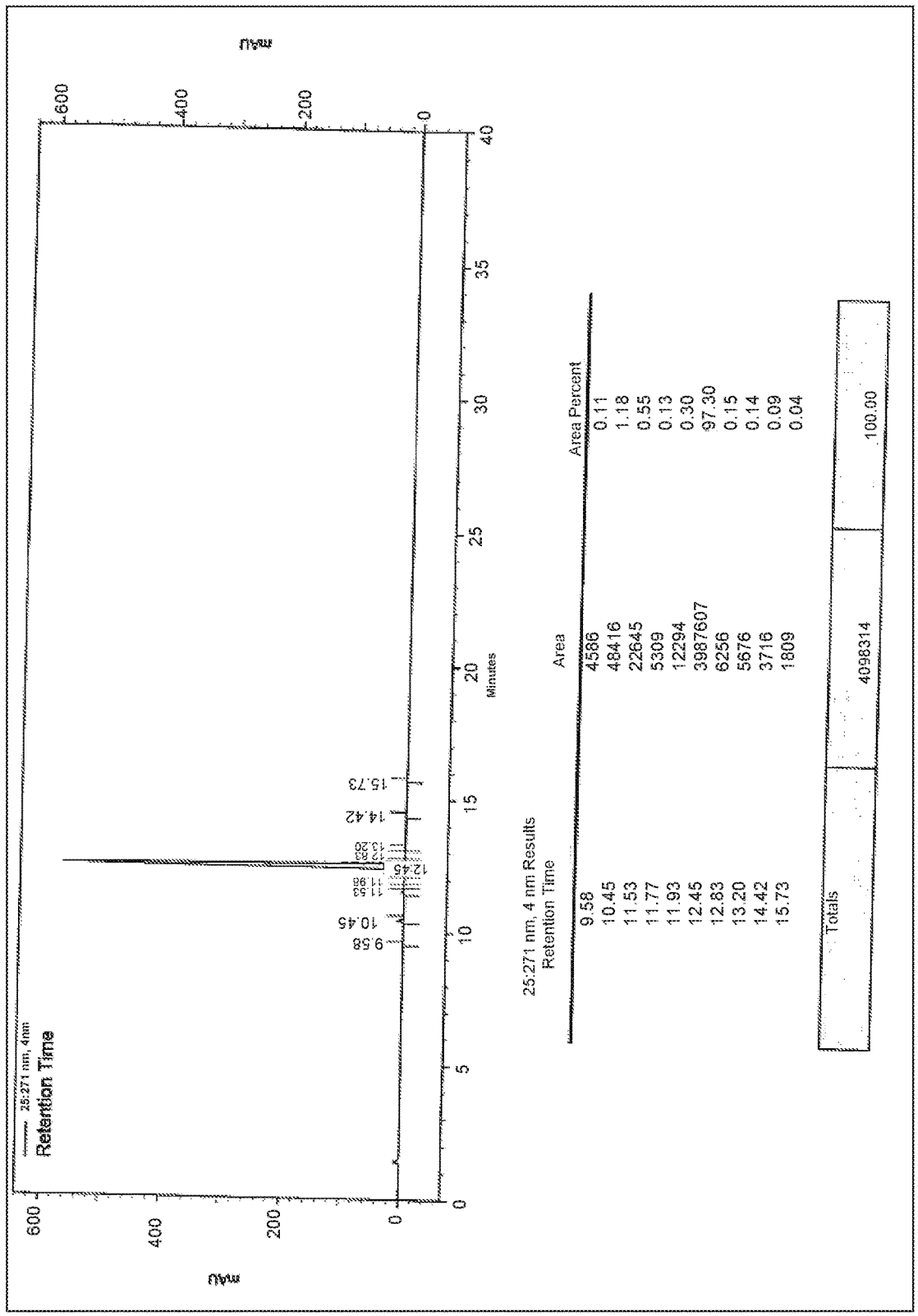
Figure 3G:
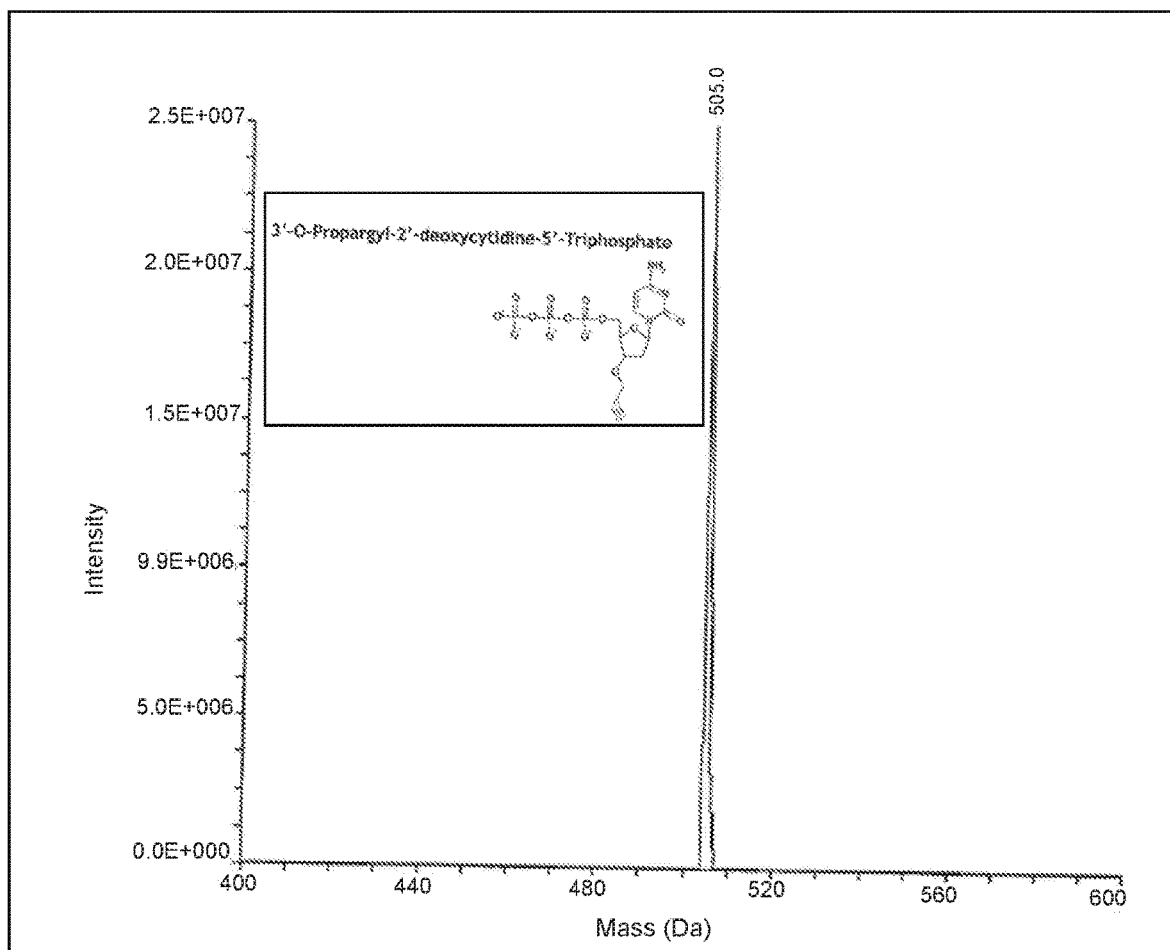
Figure 4A:
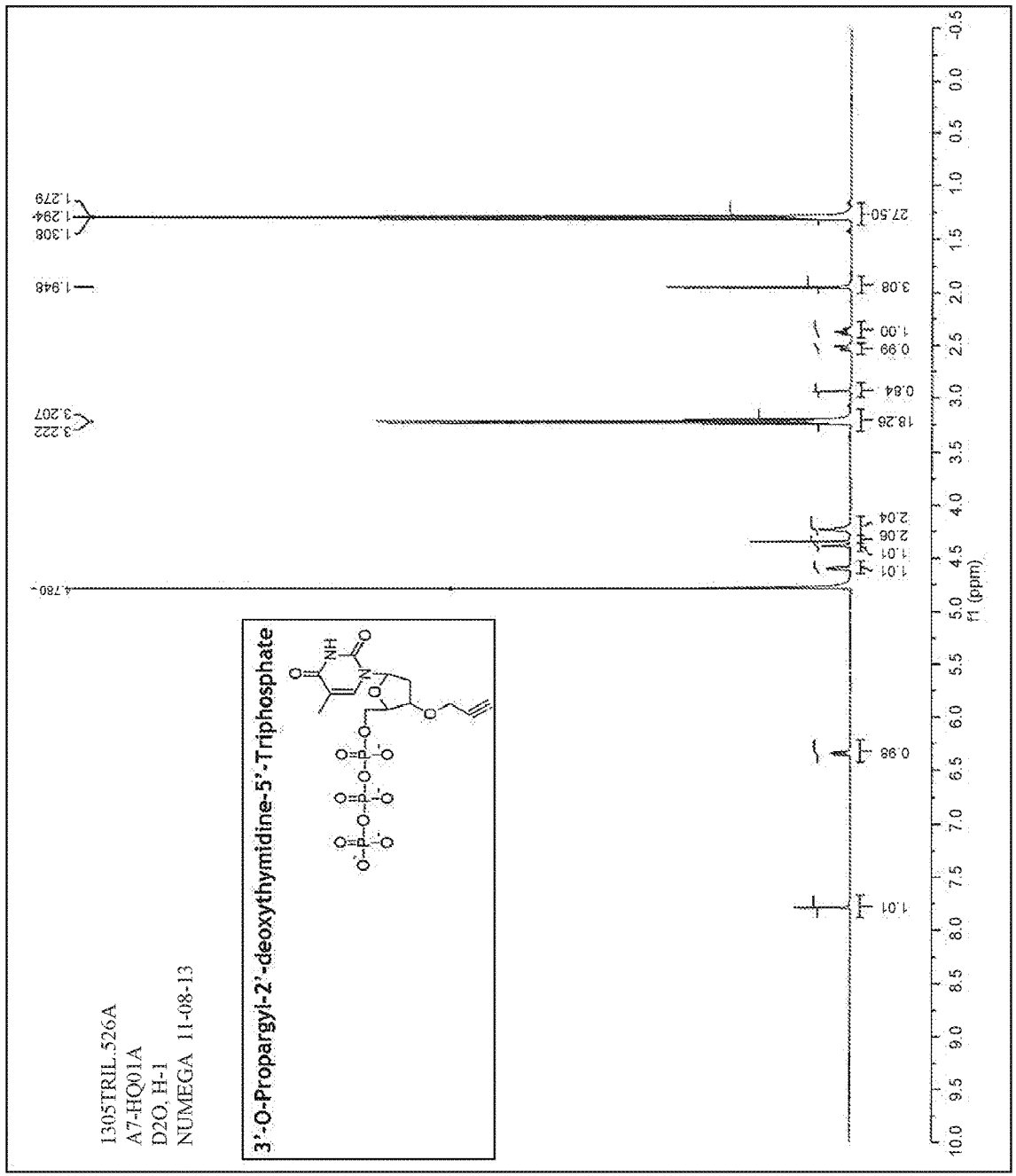
FIG. 4A-4G show analytical data for 3'-O-propargyl-2'-deoxythymidine-5'-triphosphate (3'-O-propargyl-dTTP) synthesized as described herein.
Figure 4B:
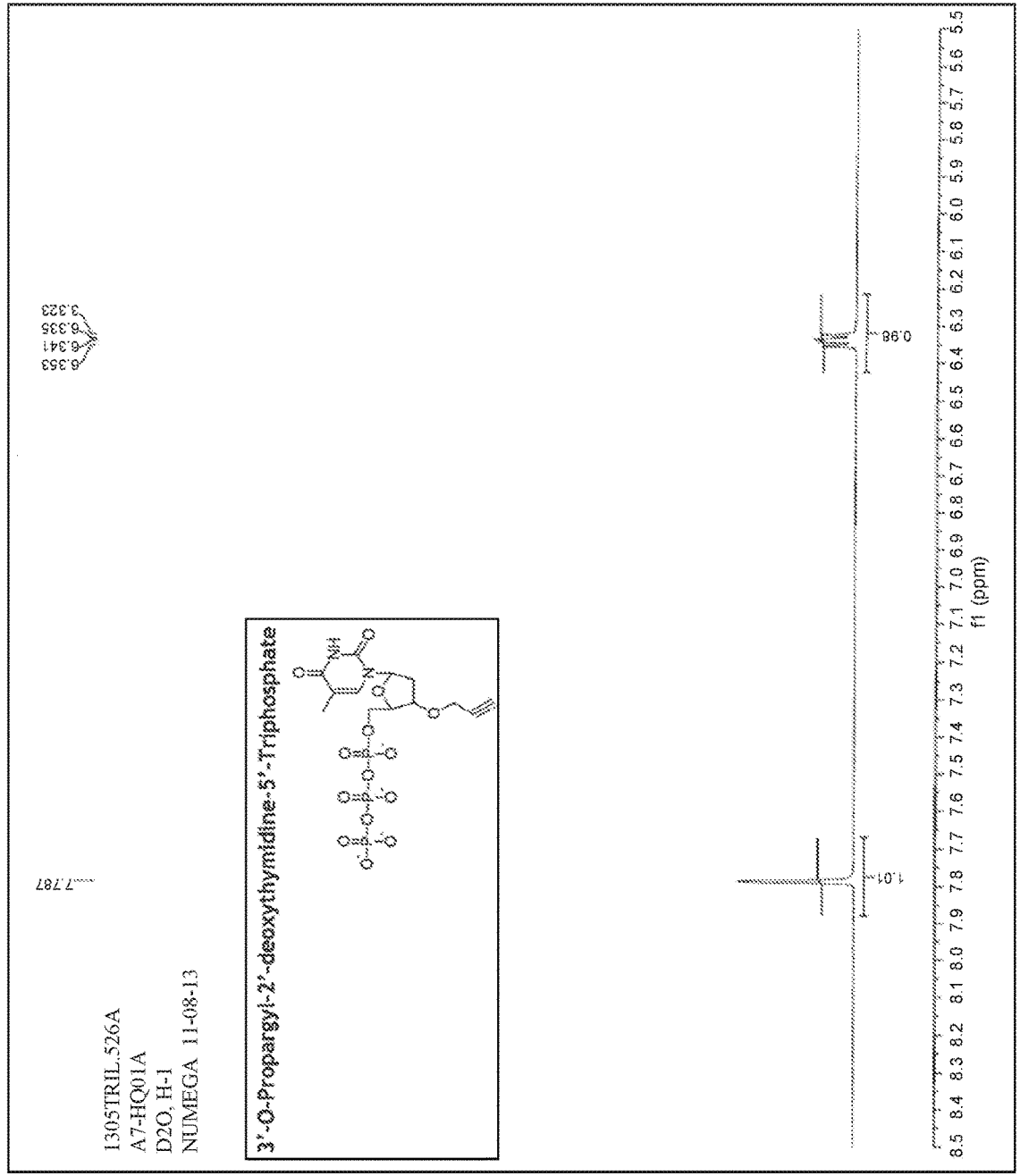
Figure 4C:
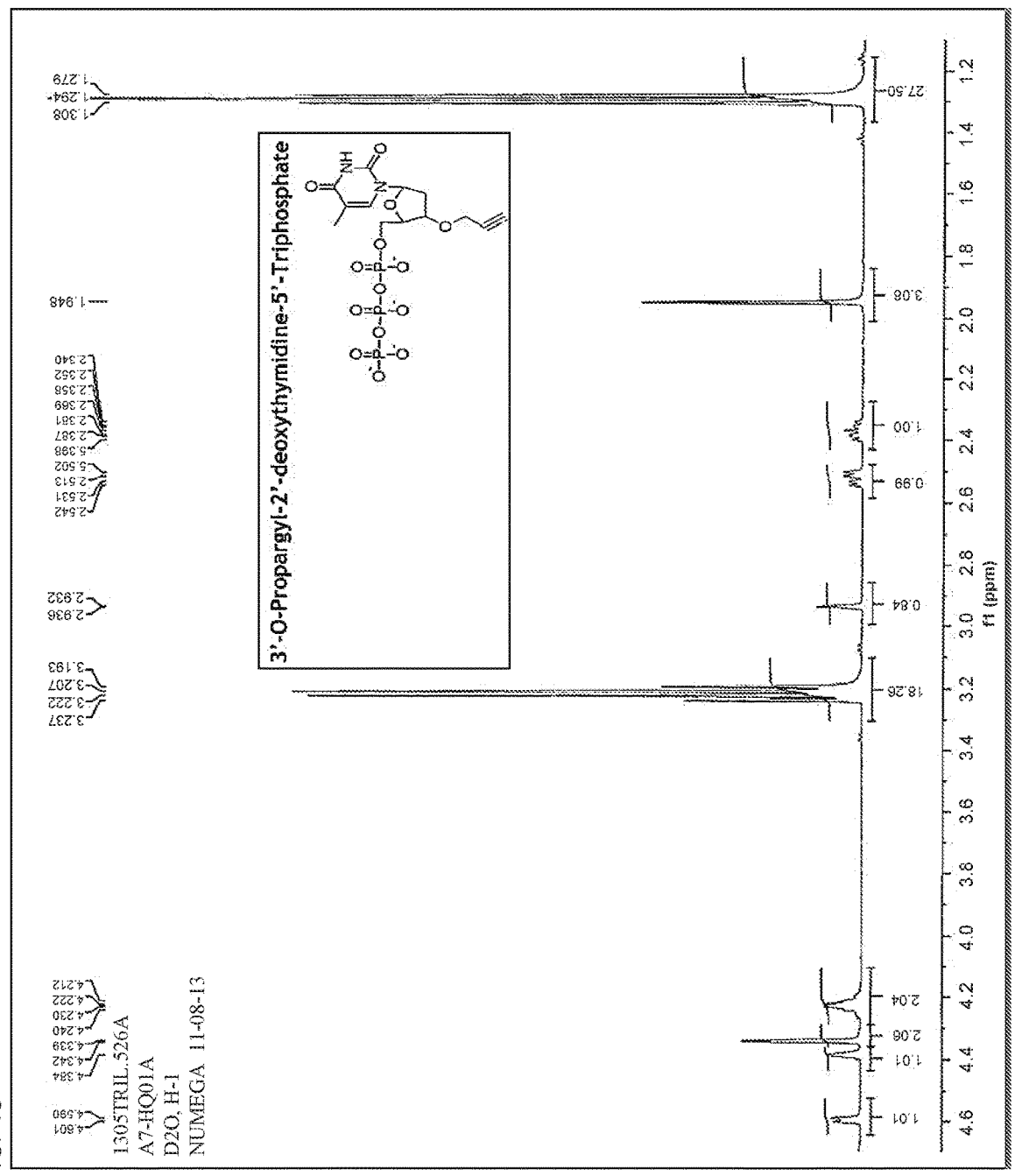
Figure 4D:
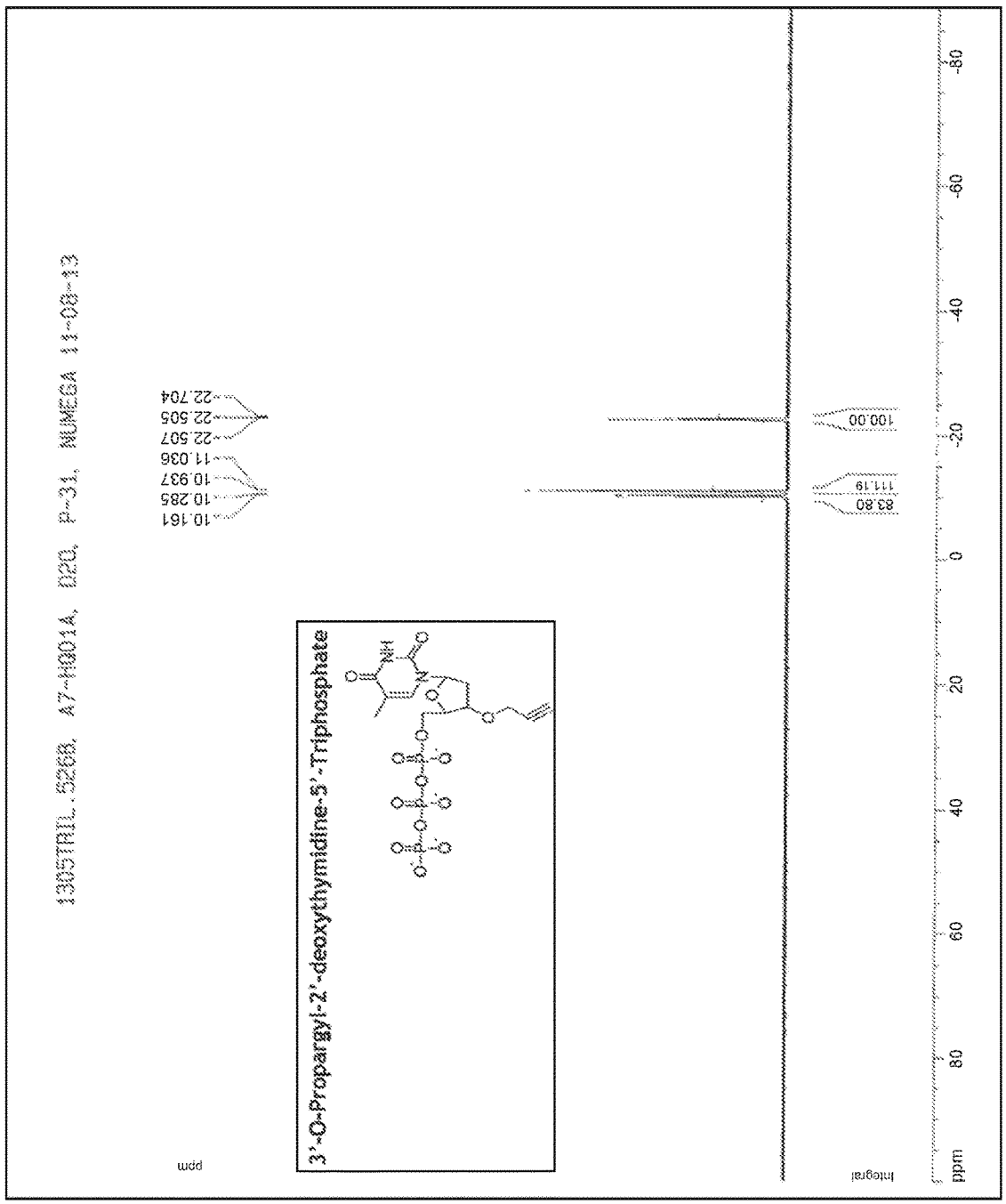
Figure 4E:
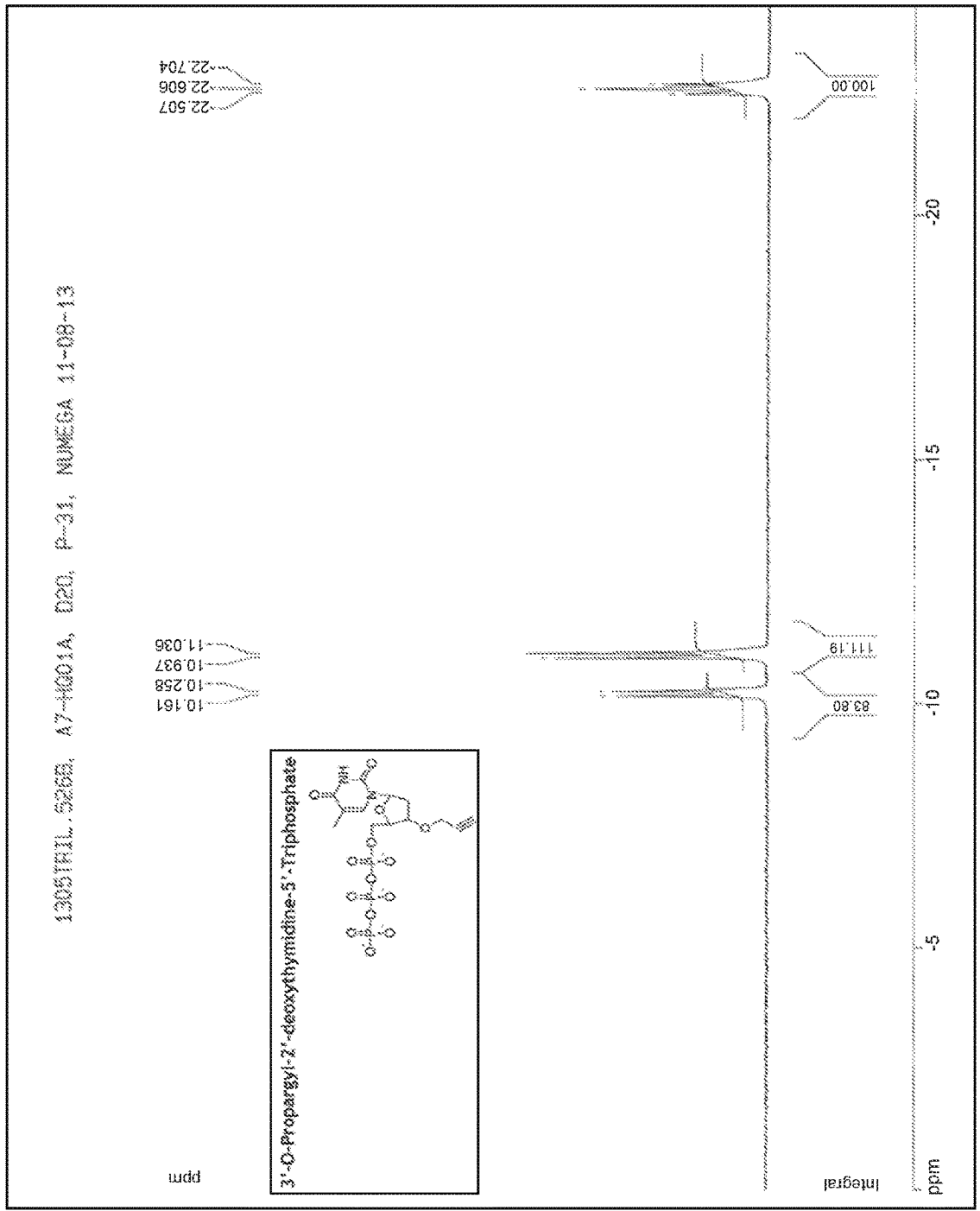
Figure 4F:
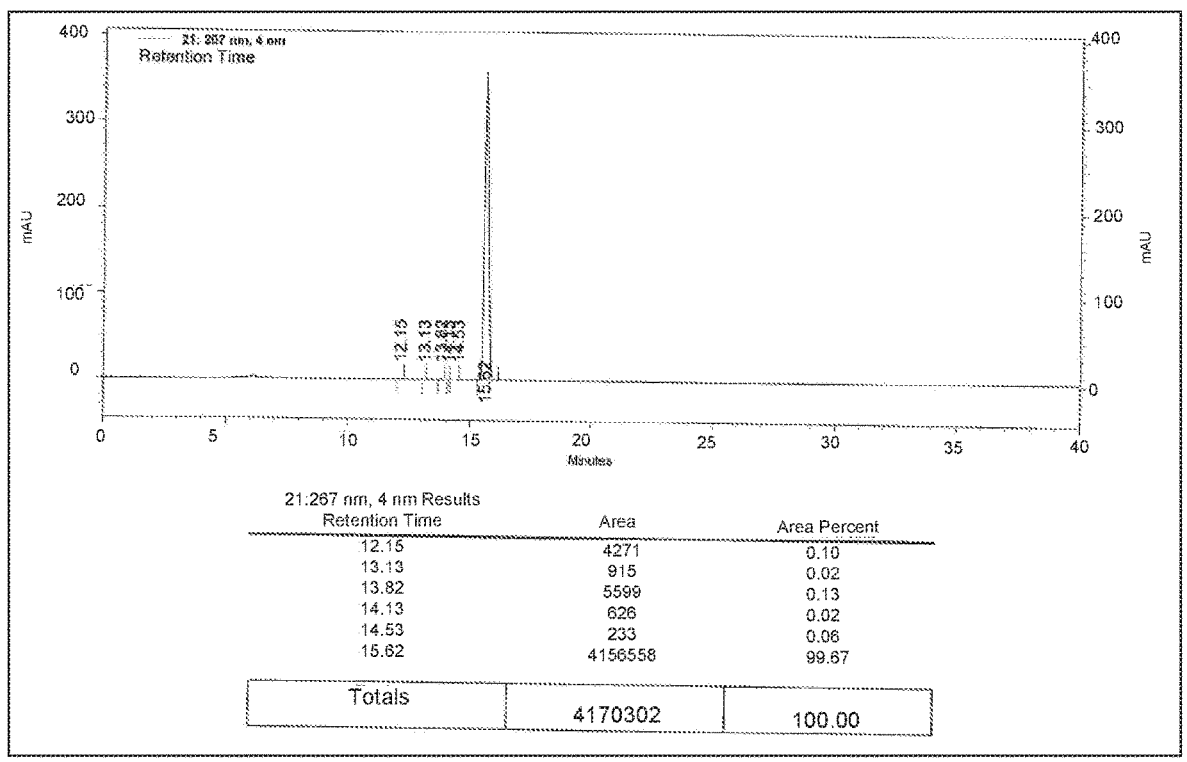
Figure 4G:
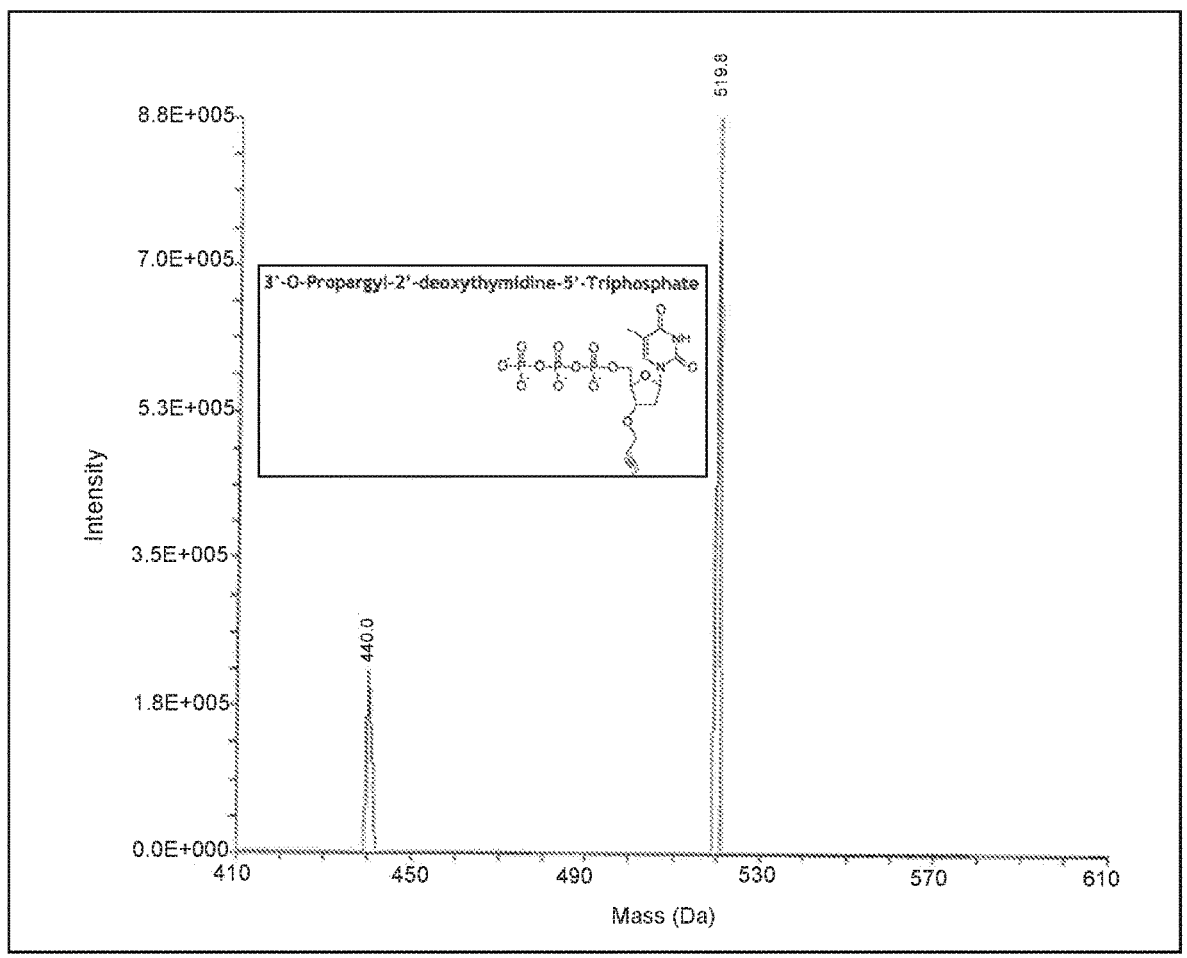
Figure 5A:
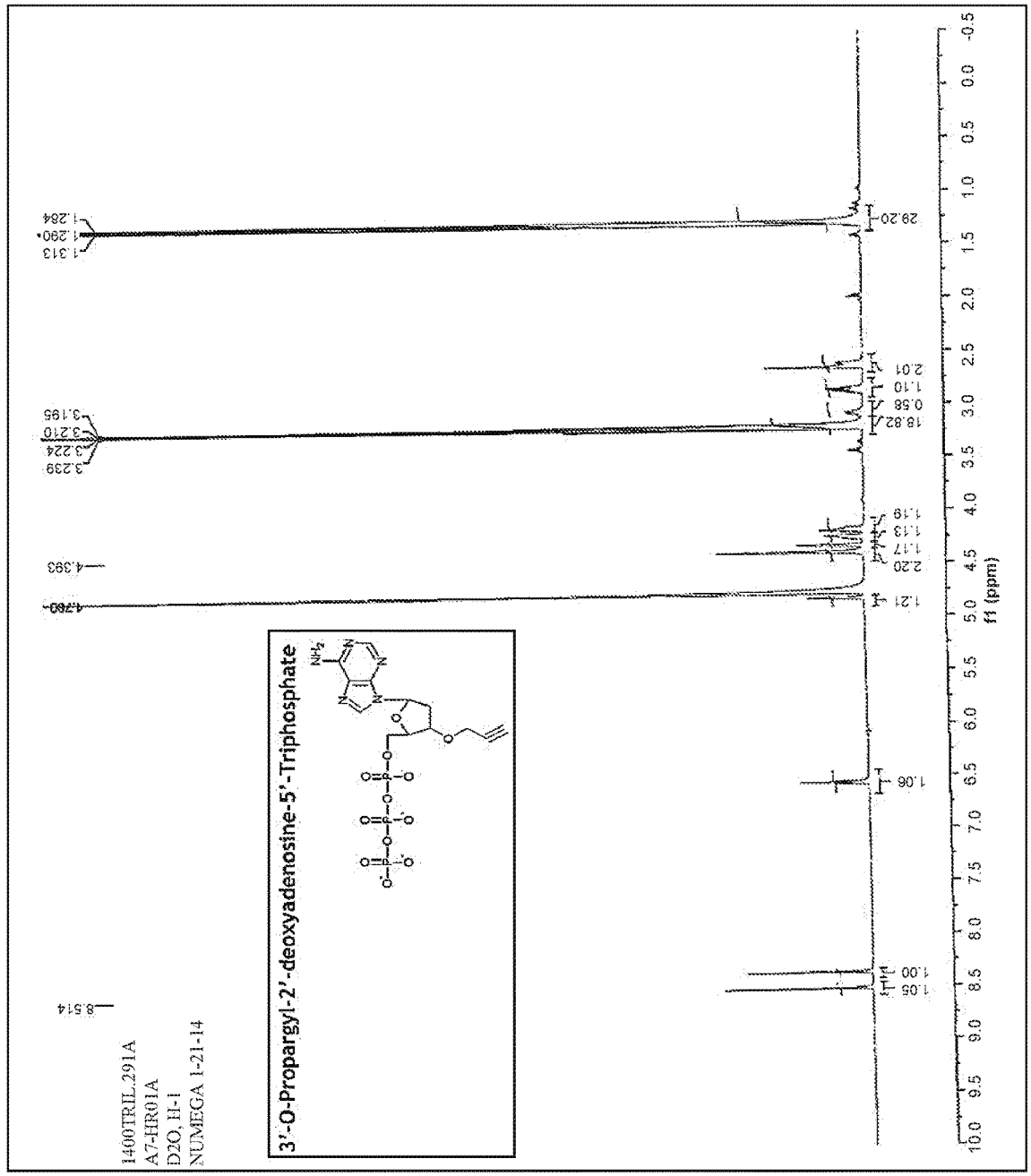
FIG. 5A-5G show analytical data for 3'-O-propargyl-2'-deoxyadenosine-5'-triphosphate (3'-O-propargyl-dATP) synthesized as described herein.
Figure 5B:
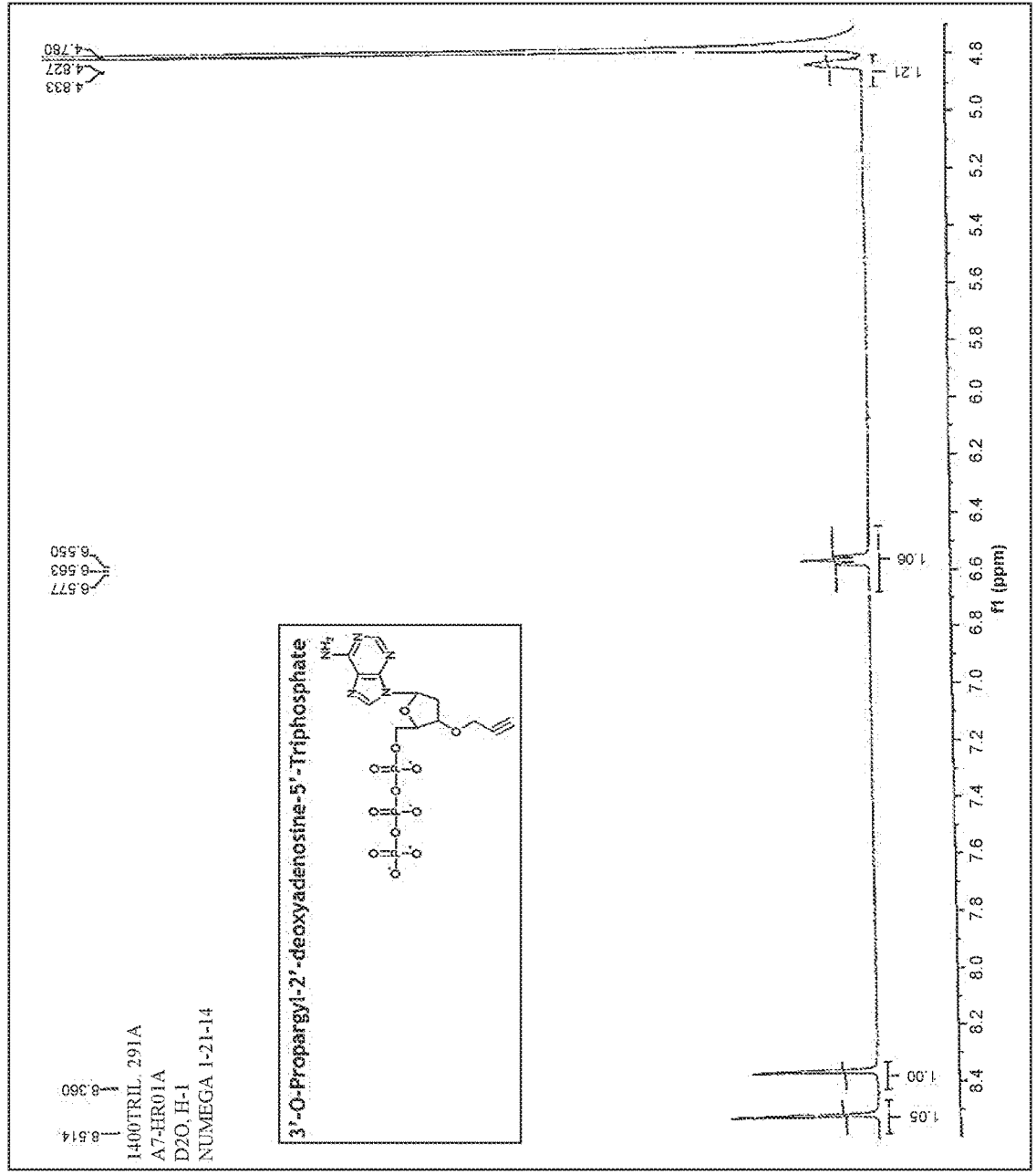
Figure 5C:
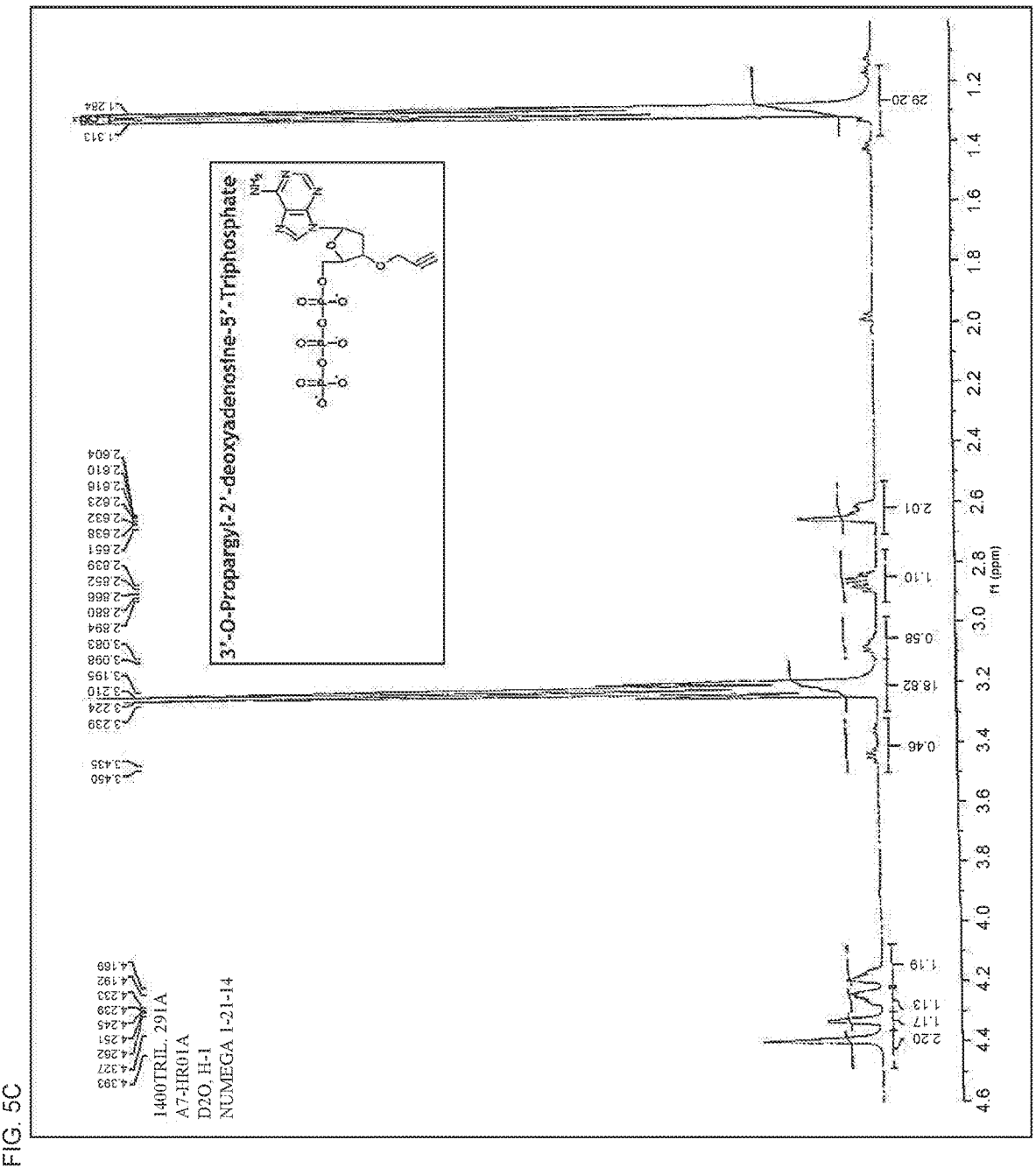
Figure 5D:
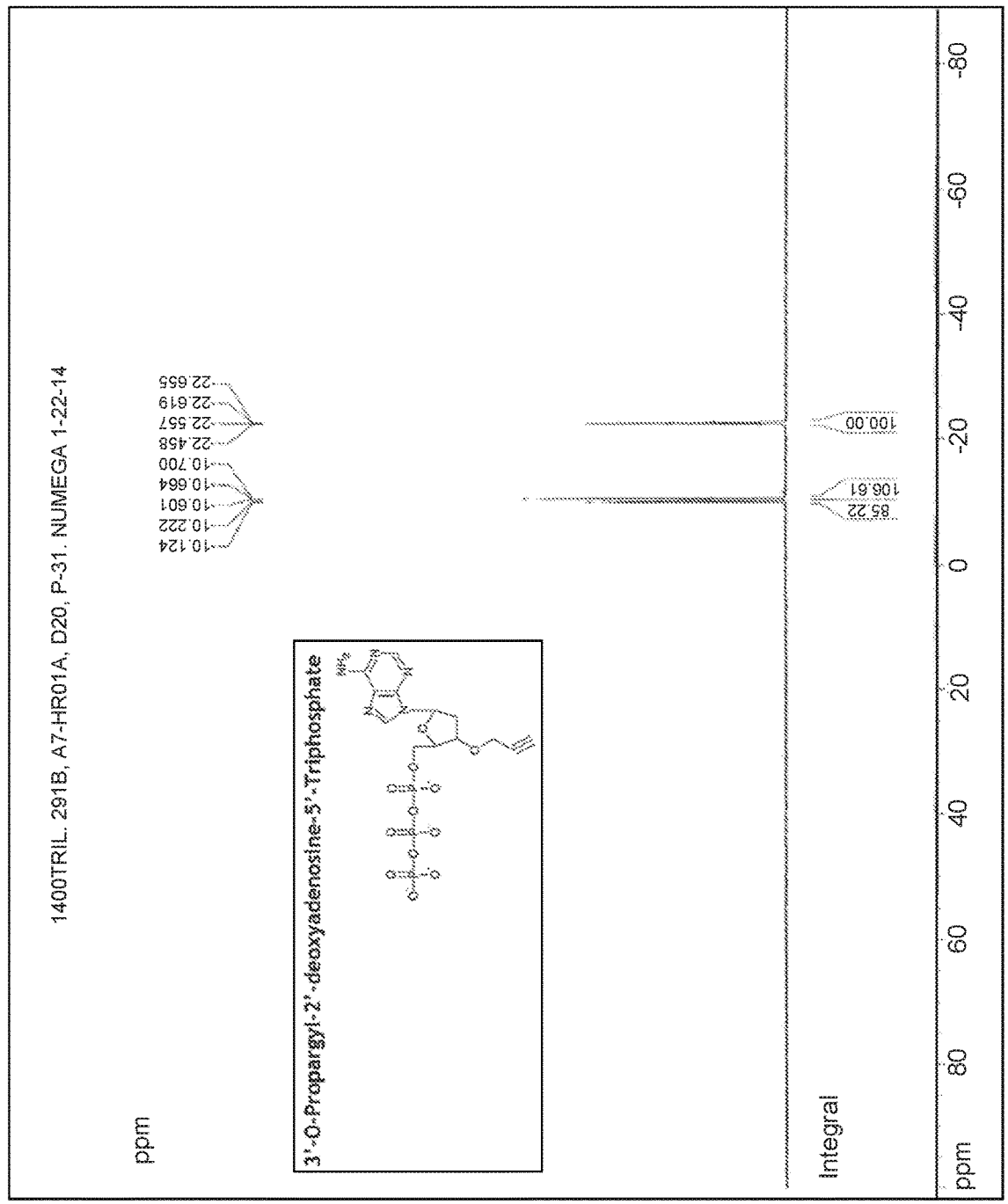
Figure 5E:
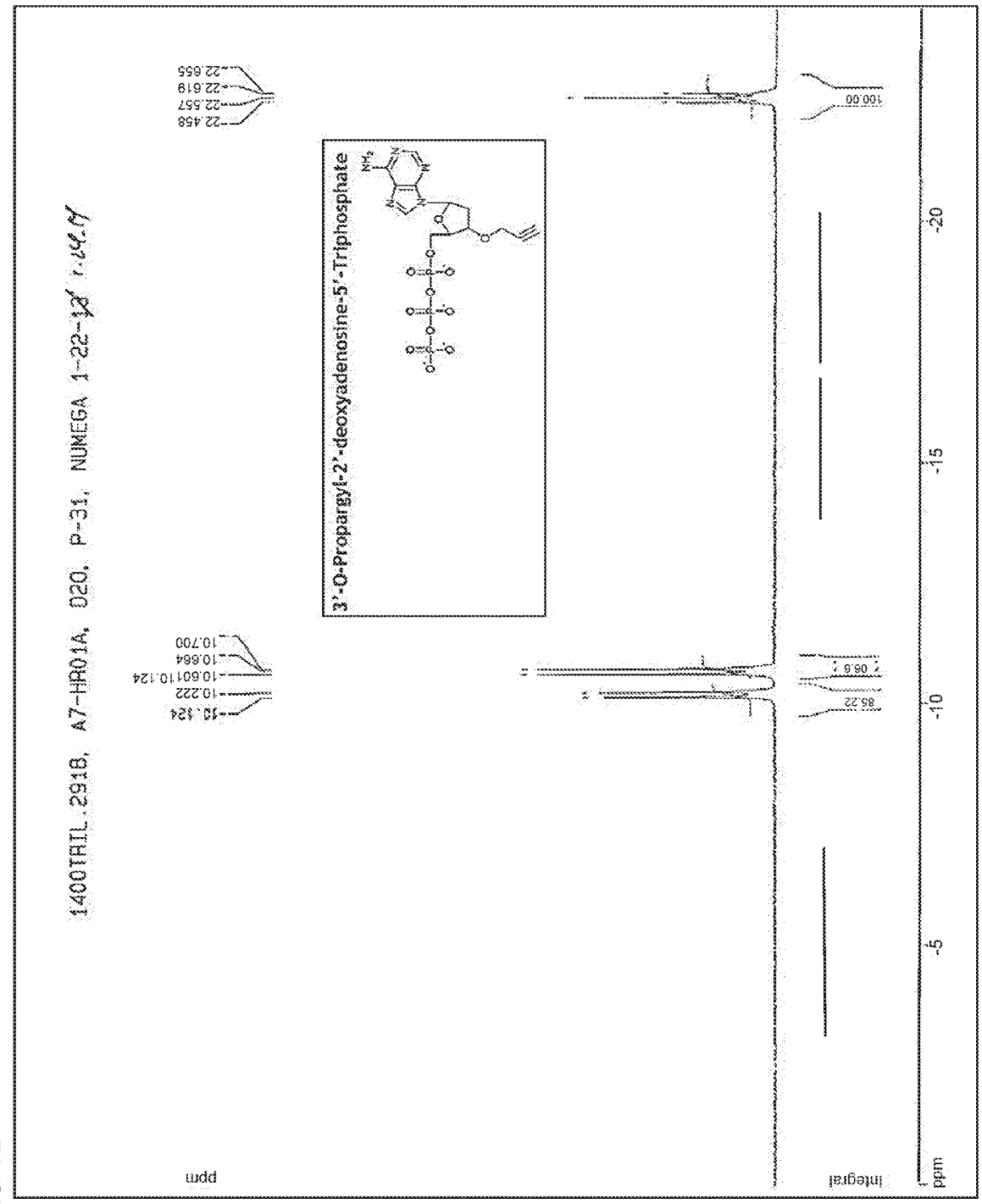
Figure 5F:
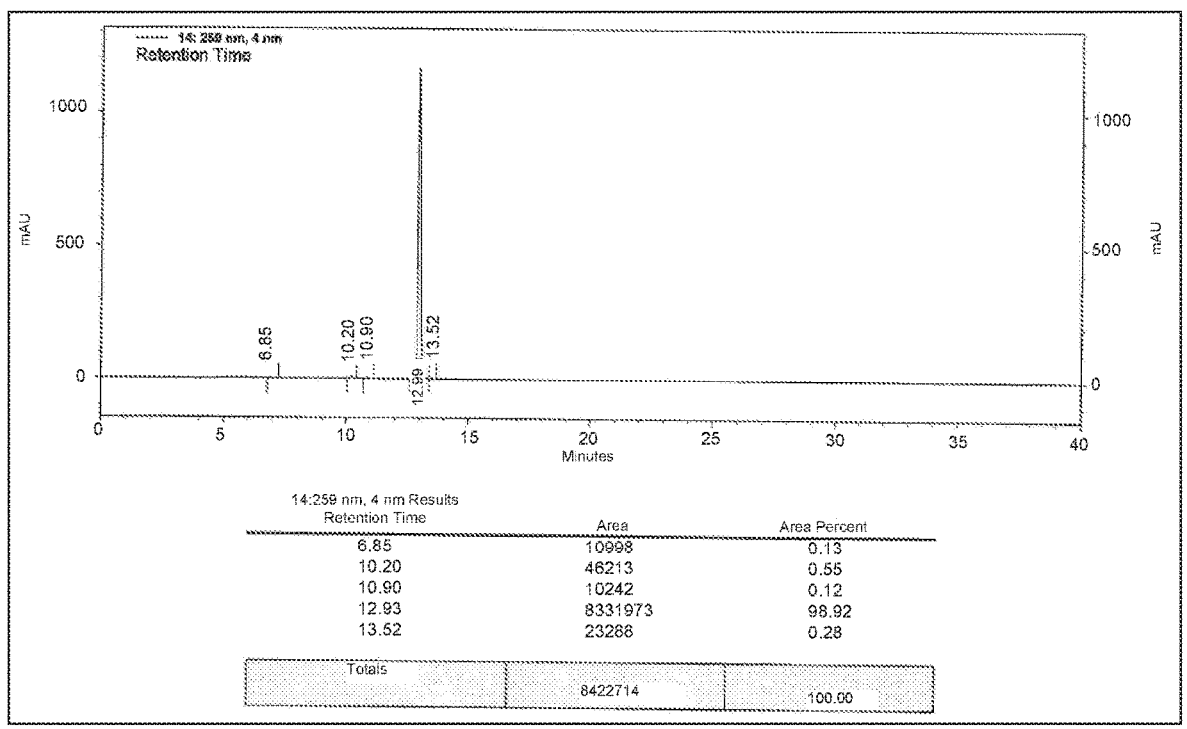
Figure 5G:
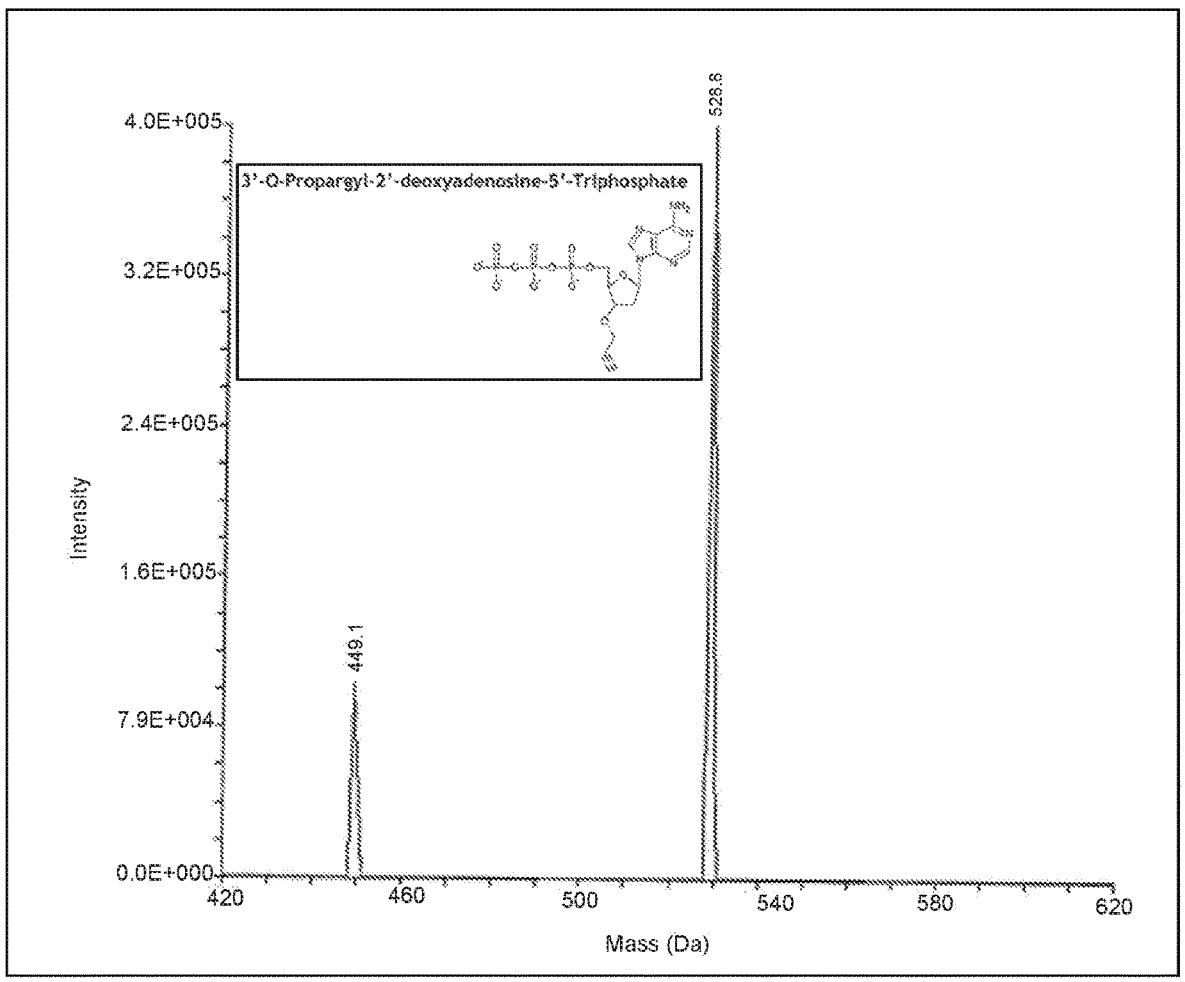
Figure 6A:
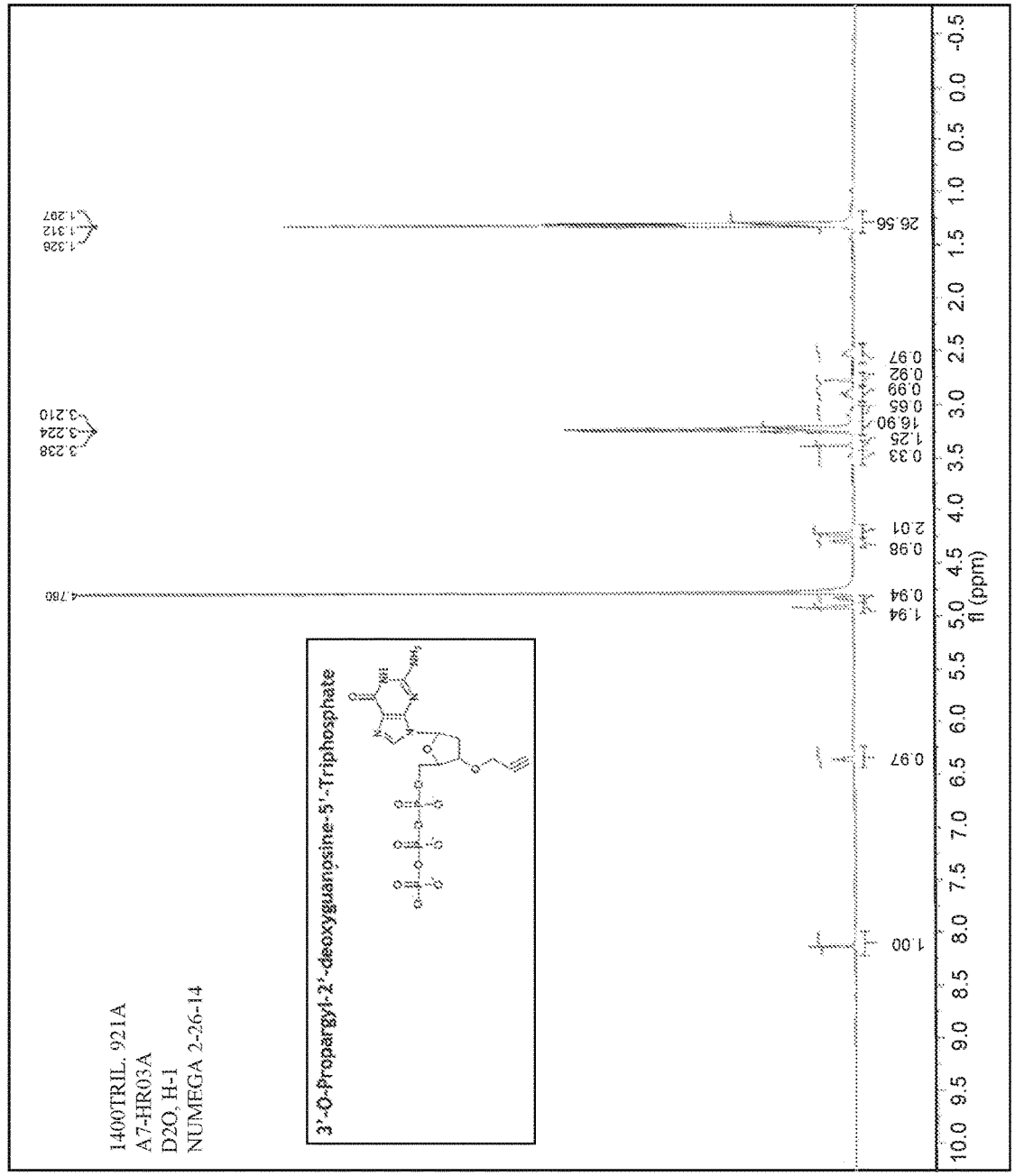
FIG. 6A-6G show analytical data for 3'-O-propargyl-2'-deoxyguanosine-5'-triphosphate (3'-O-propargyl-dGTP) synthesized as described herein.
Figure 6B:
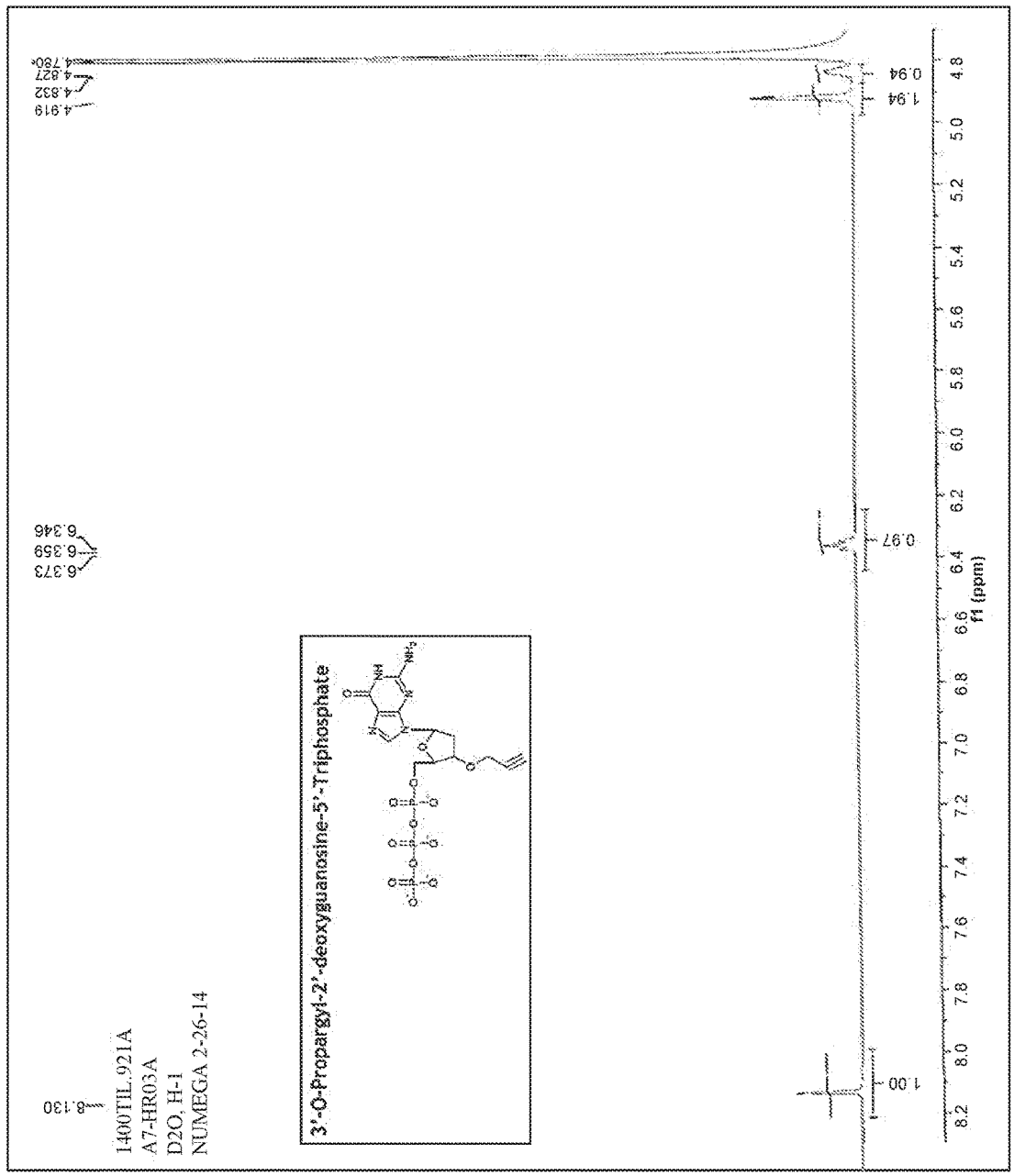
Figure 6C:
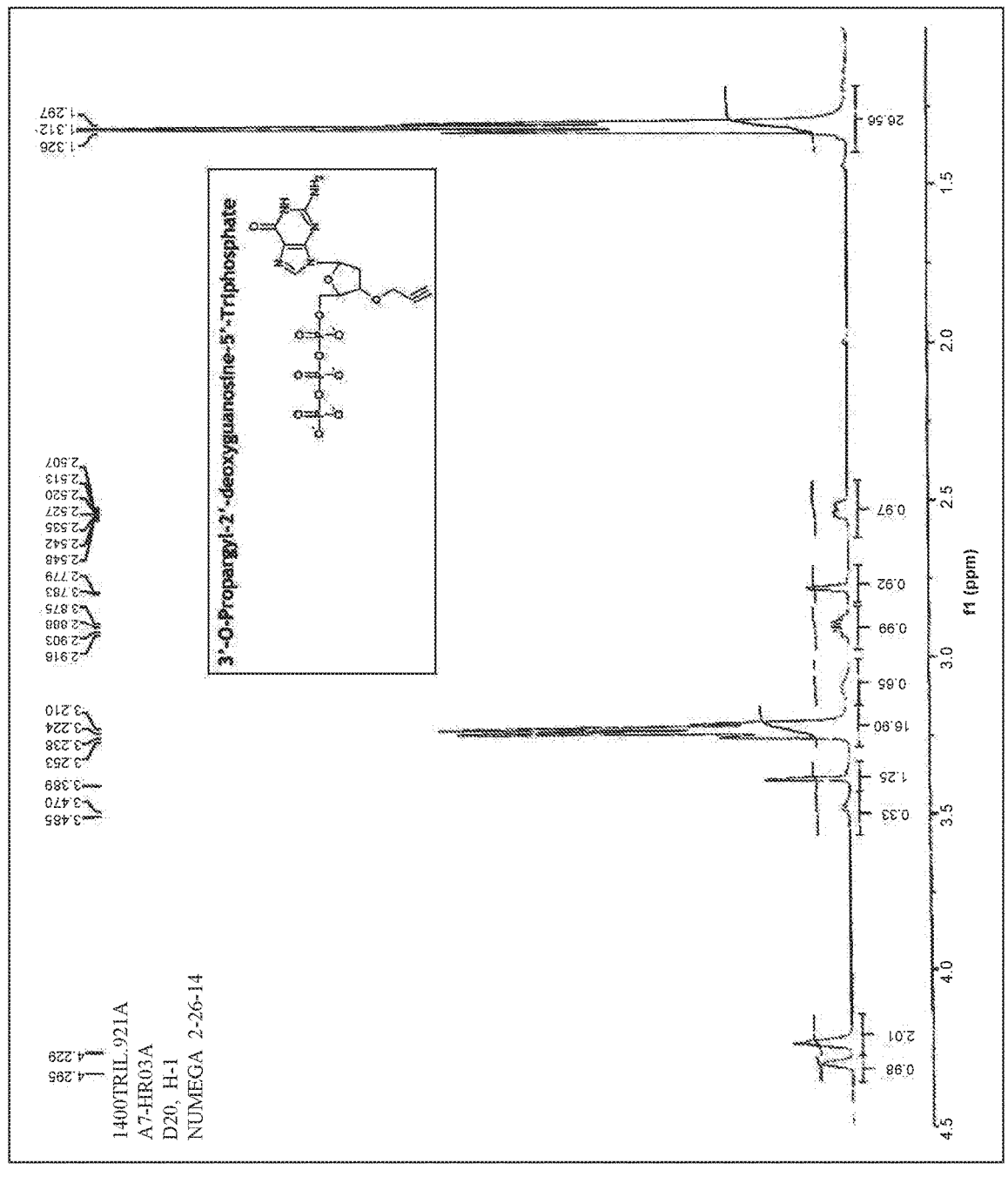
Figure 6D:
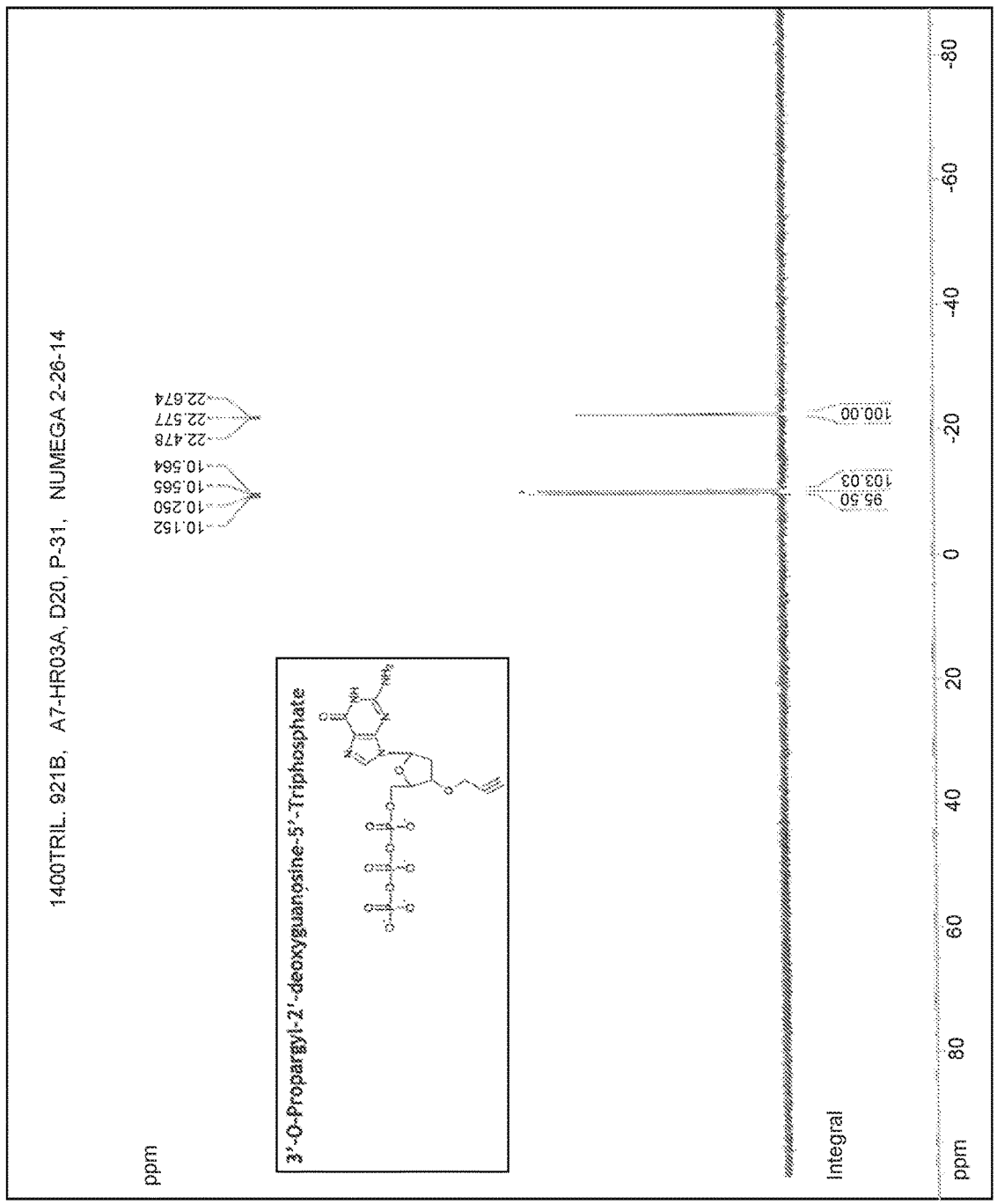
Figure 6E:
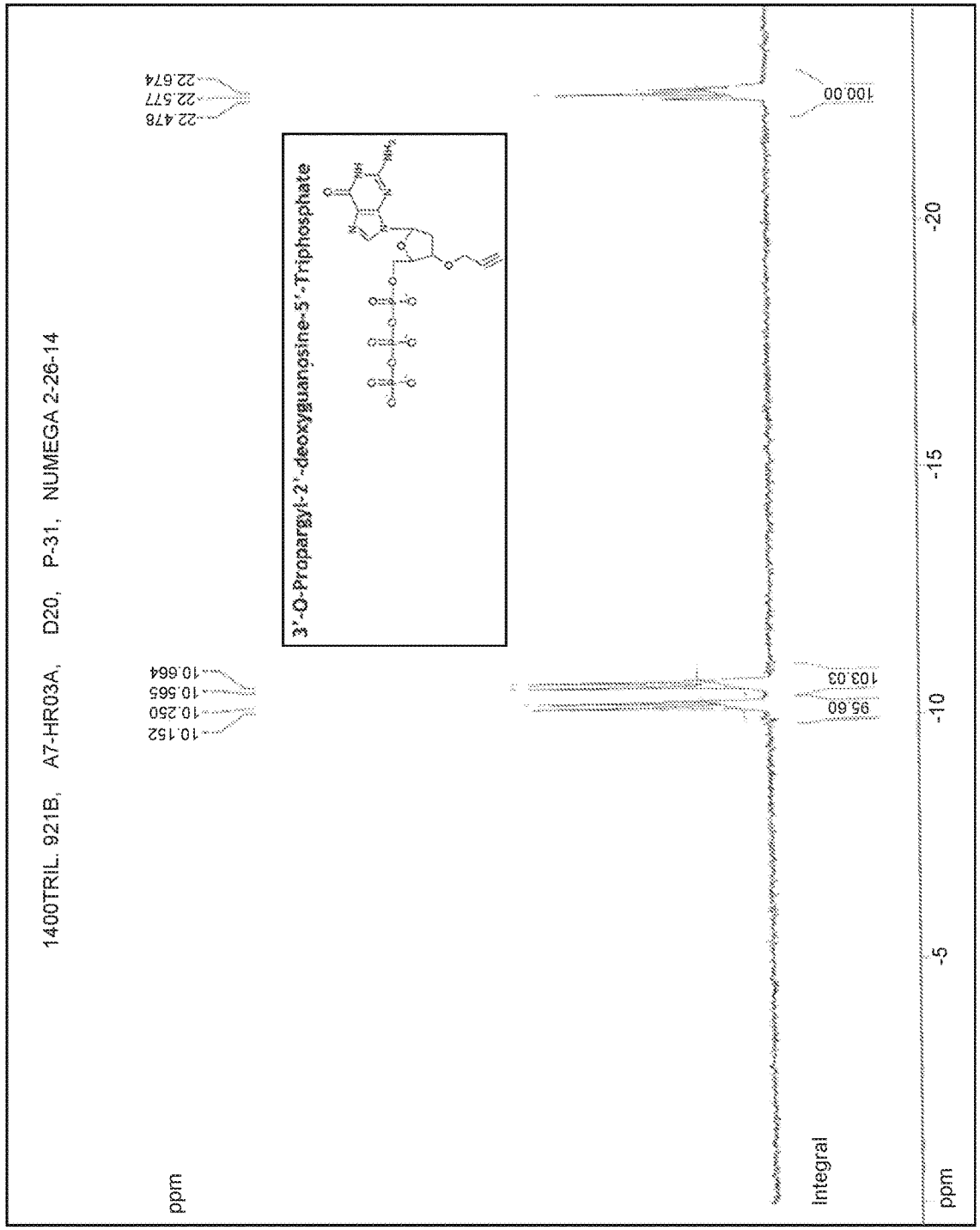
Figure 6F:
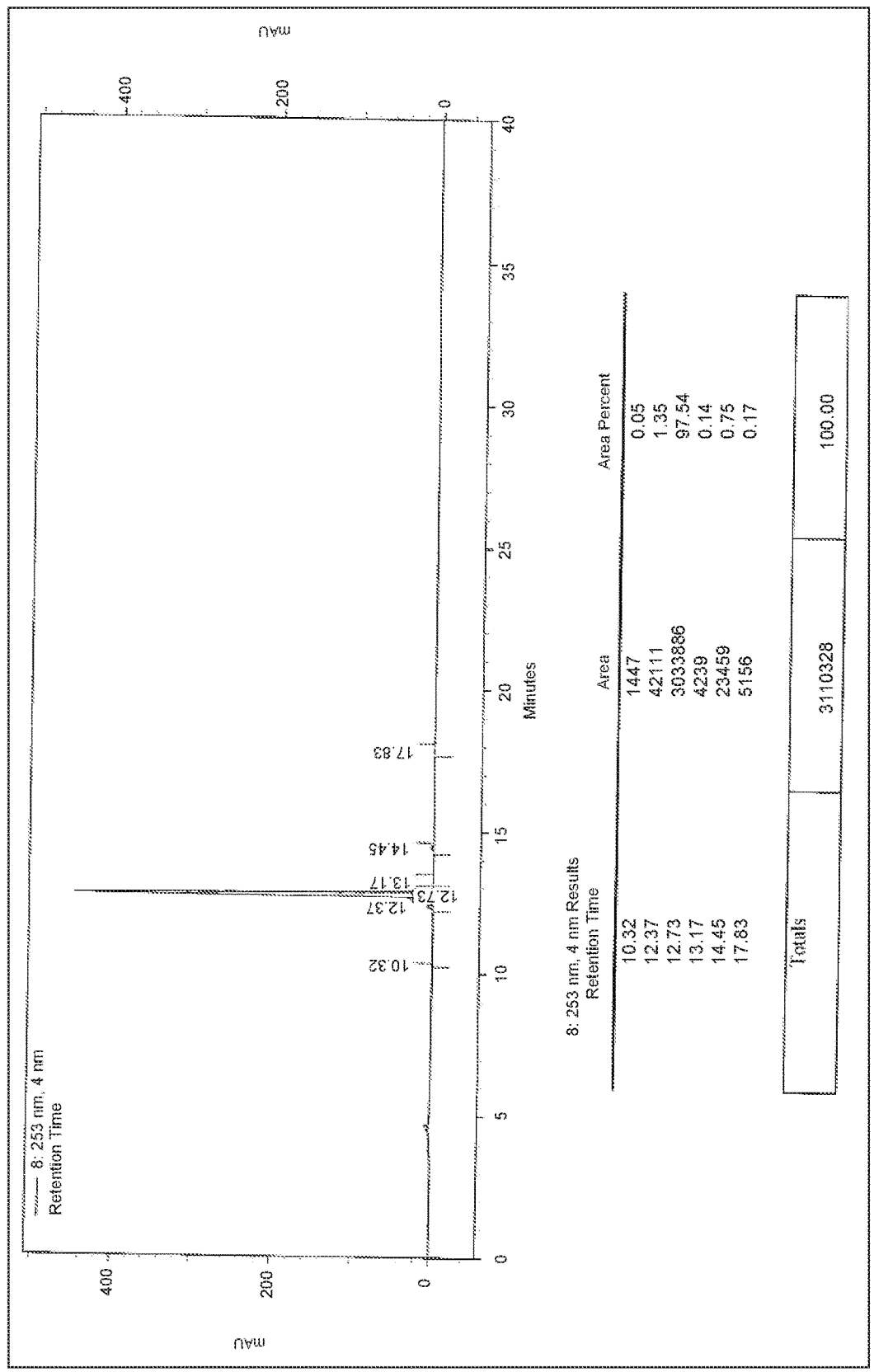
Figure 6G:
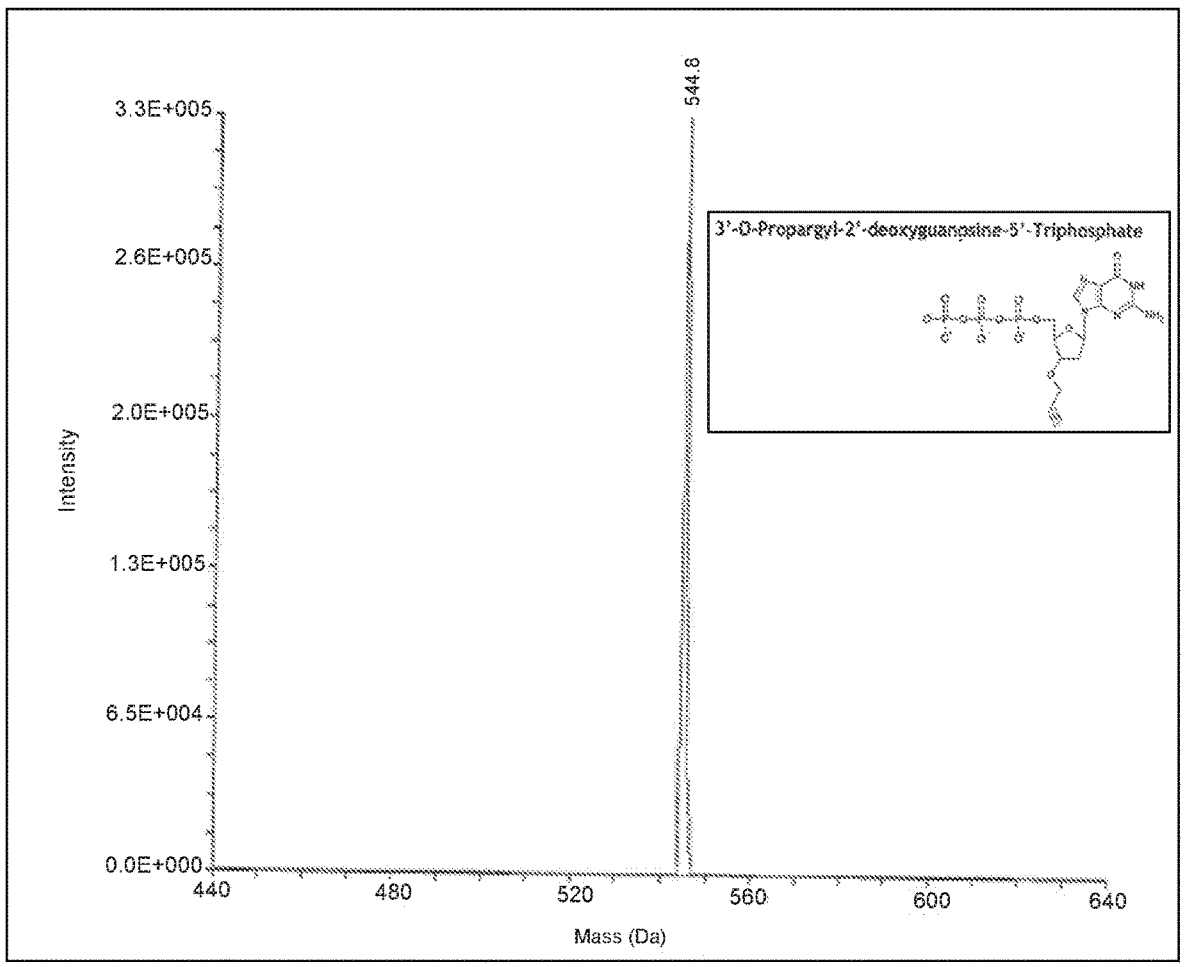

In some embodiments, the present invention provides functional terminator nucleotides containing 3'-alkynes that are incorporated into a growing nucleic acid polymer and terminate the extension reaction. The 3'-alkyne can be immediately used in a reaction with an azide-modified tag through click chemistry. The linkage created through click chemistry mimics a natural nucleic acid phosphodiester bond and provides for the use of the conjugated product in subsequent enzymatic reactions such as PCR. In this way, some embodiments of the present invention eschew the terminator cleavage step of the reversible terminator sequencing reaction and thereby decrease the run time of the reaction (see, e.g., the embodiment depicted in FIG. 2).

In some embodiments, a nucleotide analog, e.g., a 3'-alkynyl nucleotide analog (e.g., a 3'-O-propargyl nucleotide analog such as a 3'-O-propargyl dNTP) is used in a polymerase reaction and nucleic acid extension products are made in which the 3' end comprises an alkyne group. The alkyne-modified nucleic acid products can subsequently be used as a specific substrate in chemical ligation reactions with compounds containing azido moieties through click chemistry (e.g., a copper(I)-catalyzed 1,3-dipolar cycloaddition reaction). This type of click chemistry conjugates alkynes and azides, forming a covalent linkage (e.g., a five-membered triazole ring) between the alkyne-containing compound and the azide-containing compound. For example, a 5'-azide-modified DNA fragment can be chemically ligated to a 3'-alkyne-modified DNA fragment using click chemistry. This conjugated DNA product can then be used as input in subsequent enzymatic reactions such as PCR or sequencing because the covalent linkage created by the five-membered triazole ring mimics the natural phosphodiester bond of the DNA backbone and does not significantly and/or detectably inhibit subsequent enzymatic activities.

The contemplated reactions involving the nucleotide analogs provide multiple potential detection events. In some embodiments, the nucleotide analog incorporates a specific fluorophore into the elongating nucleic acid strand. In some embodiments, the addition of the nucleotide analog creates a detectable signal such as pyrophosphate. In some embodiments, the incorporation of the nucleotide analog can be detected by emission of light, change in fluorescence, change in pH, change in conformation, or some other chemical change. In some embodiments the click chemistry reaction between the incorporated nucleotide analog and a compound comprising an azido moiety can be detected in ways similar to the incorporation of the nucleotide analog.

Because of the click chemistry, the alkyne-containing nucleotide analogs readily react with compounds containing azido moieties. Using this click chemistry, various tags can be inserted covalently into an elongating nucleic acid strand that contains one of the nucleotide analogs. Examples of such tags include but are not limited to fluorescent dyes, DNA, RNA, oligonucleotides, nucleosides, proteins, amino acids, polypeptides, polysaccharides, nucleic acid, synthetic polymers, and viruses.

The technology relates in some embodiments to methods for sequencing a nucleic acid. In some embodiments, sequencing is performed by the following sequence of events with the exemplary use of a nucleotide analog comprising a 3'-O-propargyl moiety. First, the nucleotide analog is oriented in the polymerase active site (e.g., by a polymerase) to be base-paired to a complementary base of the template strand and to be adjacent to the free 3' hydroxyl of the growing synthesized strand. Next, the nucleotide analog is added to the 3' end of a growing strand by the polymerase, e.g., by the enzyme-catalyzed attack of the 3' hydroxyl on the alpha-phosphate of the nucleotide analog. Further extension of the strand by the polymerase is blocked by the 3'-O-propargyl terminating group on the incorporated nucleotide analog. In some embodiments, the strand is then subjected to a PCR reaction and used in various sequencing methods.

In some embodiments, the 3'-O-propargyl terminating moiety is treated with an azide-tagged DNA molecule. This removes the terminator alkyne. Once the terminator has been removed the growing strand is free for further polymerization: the next base is incorporated to continue another cycle, e.g., a nucleotide analog is oriented in the polymerase active site, the nucleotide analog is added to the 3' end of the growing strand by the polymerase, and the nucleotide analog is queried to identify the base added.

Some embodiments relate to parallel (e.g., massively parallel) sequencing.

In some embodiments, the technology described herein is related to a method for sequencing nucleic acid comprising: hybridizing a primer to a nucleic acid to form a hybridized primer/nucleic acid complex, providing a plurality of nucleotide analogs, each nucleotide analog comprising a nucleotide and an alkyne moiety attached to the nucleotide, reacting the hybridized primer/nucleic acid complex and the nucleotide analog with a polymerase to add the nucleotide analog to the primer by a polymerase reaction to form an extended product comprising an incorporated nucleotide analog, querying the extended product to identify the incorporated nucleotide analog, reacting the extended product with an azide-containing compound to form a structure comprising a triazole ring. In some embodiments the nucleotide analogs comprise 3'-O-propargyl-dNTP where N is selected from the group consisting of A, C, G, T and U. In some embodiments, the nucleic acid conjugate comprising a triazole ring is used in subsequent enzymatic reactions such as polymerase chain reaction. In some embodiments, the method includes providing conventional nucleotides during the same step that the nucleotide analogs are provided.

In some embodiments, the technology described herein provides a method for sequencing a nucleic acid comprising: hybridizing a primer to a nucleic acid to form a hybridized primer/nucleic acid complex, providing a plurality of nucleotides (some of which are nucleotide analogs comprising a nucleotide and an alkyne moiety attached to the nucleotide), reacting the hybridized primer/nucleic acid complex and the nucleotide analog with a polymerase to add the nucleotide analog to the primer by a polymerase reaction to form an extended product comprising an incorporated nucleotide analog, and querying the structure comprising a triazole ring to identify which analog nucleotide was incorporated. In some embodiments, the methods further comprise reacting the extended product with an azide-containing compound to form a structure comprising a triazole ring. In some embodiments the nucleotide analogs comprise 3'-O-propargyl-dNTP where N is selected from the group consisting of A, C, G, T and U. In some embodiments, the structure comprising a triazole ring is used in subsequent enzymatic reactions such as polymerase chain reaction. In some embodiments, the method includes providing conventional nucleotides during the same step that the nucleotide analogs are provided.

In some particular embodiments comprising use of a polymerase to incorporate the nucleotide analogs into a nucleic acid (e.g., PCR, primer extension, DNA sequencing (e.g., NGS), single-base extension, etc.), the polymerase is a polymerase obtained from, derived from, isolated from, cloned from, etc. a *Thermococcus* species (e.g., an organism of the taxonomic lineage Archaea; Euryarchaeota; Thermococci; Thermococcales; Thermococcaceae; *Thermococcus*). In some embodiments, the polymerase is obtained from, derived from, isolated from, cloned from, etc. a *Thermococcus* species 9○N-7 (see, e.g., Southworth, et al. (1996) "Cloning of thermostable DNA polymerases from hyperthermophilic marine Archaea with emphasis on *Thermococcus* sp. 9○N-7 and mutations affecting 3'-5' exonuclease activity" *Proc. Natl. Acad. Sci. USA* 93: 5281, incorporated herein by reference in its entirety). The nucleotide sequence encoding the wild type *Thermococcus* sp. 9○N-7 polymerase is provided by GenBank Accession Number U47108 (e.g., the polymerase gene starts at nucleotide 40 of Accession Number U47108) and the amino acid sequence of the wild type *Thermococcus* sp. 9○N-7 polymerase is provided by GenBank Accession Number AAA88769.

In some embodiments, the polymerase comprises amino acid substitutions that provide for improved incorporation of modified substrates such as modified dideoxynucleotides, ribonucleotides, and acyclonucleotides. In some embodiments, the polymerase comprises amino acid substitutions that provide for improved incorporation of nucleotide analogs comprising modified 3' functional groups such as the 3'-O-propargyl dNTPs described herein. In some embodiments the amino acid sequence of the polymerase comprises one or more amino acid substitutions relative to the *Thermococcus* sp. 9○N-7 wild-type polymerase amino acid sequence, e.g., a substitution of alanine for the aspartic acid at amino acid position 141 (D141A), a substitution of alanine for the glutamic acid at amino acid position 143 (E143A), a substitution of valine for the tyrosine at amino acid position 409 (Y409V), and/or a substitution of leucine for the alanine at amino acid position 485 (A485L).

In some embodiments, the polymerase is provided in a heterologous host organism such as *Escherichia coli* that comprises a cloned *Thermococcus* sp. 9○N-7 polymerase gene, e.g., comprising one or more mutations (e.g., D141A, E143A, Y409V, and/or A485L). In some embodiments, the polymerase is a *Thermococcus* sp. 9○N-7 polymerase sold under the trade name THERMINATOR (e.g., THERMINATOR II) by New England BioLabs (Ipswich, Mass.).

In some embodiments, methods for producing polymerase mutants and screening their activities (e.g., incorporation of modified nucleotides) are described in, e.g., Gardner and Jack (1999) "Determinants of nucleotide sugar recognition in an archaeon DNA polymerase" Nucleic Acids Research 27(12): 2545, incorporated by reference herein in its entirety. In particular, methods for producing and identifying polymerase mutants that incorporate modified nucleotides are provided by, e.g., Gardner and Jack (2002) "Acyclic and dideoxy terminator preferences denote divergent sugar recognition by archaeon and Taq DNA polymerases" Nucleic Acids Research 30(2): 605, incorporated by reference herein in its entirety. Additional assays for characterizing the incorporation of modified nucleotides by various polymerases are described, e.g., in Ruparel et al. (2005). Proc. Natl. Acad. Sci. USA. 26: 5932; Barnes (1978). J. Mol. Biol. 119: 83; Sanger et al. (1977). Proc. Natl. Acad. Sci. USA. 74: 5463; Haff and Simirnov (1997) Genome Methods 7: 378; and in U.S. Pat. No. 5,558,991, each incorporated herein by reference in entirety.

6. Uses

The nucleotide analogs provided herein find use in a wide range of applications. Non-limiting examples of uses for the nucleotide analogs described include use as antiviral and/or anticancer agents. In some embodiments, the nucleotide analogs provided herein find use in diagnostic medical imaging, e.g., as contrast agents for use in, e.g., MRI, computed tomography (CT) scans, X-ray imaging, angiography (e.g., venography, digital subtraction angiography (DSA), arteriography), intravenous urography, intravenous pyelography, myelography, interventional medicine (e.g., angioplasty (e.g., percutaneous transluminal angioplasty), artery ablation and/or occlusion (e.g., to treat cancer and/or vascular abnormalities), and placement of stents), arthrography, sialography, retrograde choledocho-pancreatography, micturating cystography, etc. Additional illustrative and non-limiting uses for such contrast agents include in vivo imaging for human diagnostics, drug discovery, and drug development in model systems (mouse models, etc.).

In some embodiments, an oligonucleotide comprising one or more nucleotide analogs described herein finds use in a nanoconjugate (e.g., comprising nanoparticles such as titanium dioxide nanoparticles, an oligonucleotide (e.g., comprising a nucleotide analog), and/or a contrast agent (e.g., a heavy metal contrast agent such as gadolinium)) for use in imaging and/or therapy (e.g., neutron-capture cancer therapy). See, e.g., Paunesku et al. *Nanomedicine* 4(3): 201-7, 2008.

In some embodiments, the technology finds use as a drug delivery tag, e.g., for the targeted cellular delivery of oligonucleotide and antisense therapeutics (e.g., siRNA, miRNA, etc.). In some embodiments, the technology finds use for the delivery of drugs linked to a nucleic acid comprising a nucleotide analog, wherein the nucleic acid serves as a targeting moiety. In some embodiments, the technology comprises use of a cell targeting moiety to direct and/or deliver an oligonucleotide to a particular cell, tissue, organ, etc. The cell targeting moiety imbues compounds (e.g., an oligonucleotide (e.g., oligonucleotide analog) according to the technology described herein linked to a cell-targeting/drug delivery moiety, e.g., as described below) with characteristics such that the compounds and/or oligonucleotides are preferably recognized, bound, imported, processed, activated, etc. by one or more target cell types relative to one or more other non-target cell types. For example, endothelial cells have a high affinity for the peptide targeting moiety Arg-Gly-Asp (RGD), cancer and kidney cells preferentially interact with compounds having a folic acid moiety, immune cells have an affinity for mannose, and cardiomyocytes have an affinity for the peptide CWLSEAGPVVTVRALRGTGSW (see, e.g., *Biomaterials* 31: 8081-8087, 2010). Other targeting/delivery moieties are known in the art. Accordingly, compounds comprising a targeting moiety preferentially interact with and are taken up by the targeted cell type.

In some embodiments, the compounds comprise an RGD peptide. RGD peptides comprise 4 to 30 (e.g., 5 to 20 or 5 to 15) amino acids and target tumor cells (e.g., endothelial tumor cells). Such peptides and agents derived therefrom are known in the art, and are described by Beer et al. in *Methods Mol. Biol.* 680: 183-200 (2011) and in *Theranostics* 1: 48-57 (2011); by Morrison et al. in *Theranostics* 1: 149-153 (2011); by Zhou et al. in *Theranostics* 1: 58-82 (2011); and by Auzzas et al. in *Curr. Med. Chem.* 17: 1255-1299 (2010).

In some embodiments, the targeting moiety is folic acid, e.g., for targeting to cells expressing the folate receptor. The folate receptor is overexpressed on the cell surfaces of human cancer cells in, e.g., cancers of the brain, kidney, lung, ovary, and breast relative to lower levels in normal cells (see, e.g., Sudimack J, et al. 2000 "Targeted drug delivery via the folate receptor" *Adv Drug Deliv Rev* 41: 147-162).

In some embodiments, the targeting moiety comprises transferrin, which targets the compounds to, e.g., macrophages, erythroid precursors in bone marrow, and cancer cells. When a transferrin protein encounters a transferrin receptor on the surface of a cell, the transferrin receptor binds to the transferrin and transports the transferrin into the cell. Drugs and other compounds and/or moieties linked to the tranferrin are also transported to the cell and, in some cases, imported into the cells. In some embodiments, a fragment of a transferrin targets the compounds of the technology to the target cell. See, e.g., Qian et al. (2002) "Targeted drug delivery via the transferrin receptor-mediated endocytosis pathway", *Pharmacol. Rev.* 54: 561-87; Daniels et al. (2006) "The transferrin receptor part I: Biology and targeting with cytotoxic antibodies for the treatment of cancer", *Clin. Immunol.* 121: 144-58.

In some embodiments, the targeting moiety comprises the peptide VHSPNKK. This peptide targets compounds to cells expressing vascular cell adhesion molecule 1 (VCAM-1), e.g., to activated endothelial cells. Targeting activated endothelial cells finds use, e.g., in delivery of therapeutic agents to cells for treatment of inflammation and cancer. Certain melanoma cells use VCAM-1 to adhere to the endothelium and VCAM-1 participates in monocyte recruitment to atherosclerotic sites. Accordingly, the peptide VHSPNKK finds use in targeting compounds of the present technology to cancer (e.g., melanoma) cells and atherosclerotic sites.

See, e.g., Lochmann, et al. (2004) "Drug delivery of oligonucleotides by peptides" *Eur. J Pharmaceutics and Biopharmaceutics* 58: 237-251, incorporated herein by reference, discussing targeting moieties and the cells targeted by those moieties.

In some embodiments, the cell-targeting moiety comprises an antibody, or derivative or fragment thereof. Antibodies to cell-specific molecules such as, e.g., proteins (e.g., cell-surface proteins, membrane proteins, proteoglycans, glycoproteins, peptides, and the like); polynucleotides (nucleic acids, nucleotides); lipids (e.g., phospholipids, glycolipids, and the like), or fragments thereof comprising an epitope or antigen specifically recognized by the antibody, target compounds according to the technology to the cells expressing the cell-specific molecules.

For example, many antibodies and antibody fragments specifically bind markers produced by or associated with tumors or infectious lesions, including viral, bacterial, fungal, and parasitic infections, and antigens and products associated with such microorganisms (see, e.g., U.S. Pat. Nos. 3,927,193; 4,331,647; 4,348,376; 4,361,544; 4,468,457; 4,444,744; 4,460,459; 4,460,561; 4,818,709; and 4,624,846, incorporated herein by reference) Moreover, antibodies that target myocardial infarctions are disclosed in, e.g., U.S. Pat. No. 4,036,945. Antibodies that target normal tissues or organs are disclosed in, e.g., U.S. Pat. No. 4,735,210. Anti-fibrin antibodies are known in the art, as are antibodies that bind to atherosclerotic plaque and to lymphocyte autoreactive clones.

For cancer (e.g., breast cancer) and its metastases, a specific marker or markers may be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2. For other forms of cancer and their metastases, a specific marker or markers may be selected from cell surface markers such as, for example, vascular endothelial growth factor receptor (VEGFR) family, a member of carcinoembryonic antigen (CEA) family, a type of anti-idiotypic mAB, a type of ganglioside mimic, a member of cluster designation differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, and a type of human carcinoma antigen.

The antibody may have an affinity for a target associated with a disease of the immune system such as, for example, a protein, a cytokine, a chemokine, an infectious organism, and the like. In another embodiment, the antibody may be targeted to a predetermined target associated with a pathogen-borne condition. The particular target and the antibody may be specific to, but not limited to, the type of the pathogen-borne condition. A pathogen is defined as any disease-producing agent such as, for example, a bacterium, a virus, a microorganism, a fungus, a prion, and a parasite. The antibody may have an affinity for the pathogen or pathogen associated matter. The antibody may have an affinity for a cell marker or markers associated with a pathogen-borne condition. The marker or markers may be selected such that they represent a viable target on infected cells. For a pathogen-borne condition, the antibody may be selected to target the pathogen itself. For a bacterial condition, a predetermined target may be the bacterium itself, for example, *Escherichia coli* or *Bacillus anthracis*. For a viral condition, a predetermined target may be the virus itself, for example, Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, *Trypanasoma cruzi*, Kinetoplastid, *Schistosoma mansoni*, *Schistosoma japonicum*, or *Schistosoma brucei*. For a fungal condition, a predetermined target may be the fungus itself, for example, *Aspergillus, Candida, Cryptococcus neoformans*, or *Rhizomucor*.

In another embodiment, the antibody may be targeted to a predetermined target associated with an undesirable target. The particular target and antibody may be specific to, but not limited to, the type of the undesirable target. An undesirable target is a target that may be associated with a disease or an undesirable condition, but also present in the normal condition. For example, the target may be present at elevated concentrations or otherwise be altered in the disease or undesirable state. Antibody may have an affinity for the undesirable target or for biological molecular pathways related to the undesirable target. Antibody may have an affinity for a cell marker or markers associated with the undesirable target. For an undesirable target, the choice of a predetermined target may be important to therapy utilizing the compounds according to the present technology (e.g., the drug and/or therapeutic moieties). The antibody may be selected to target biological matter associated with a disease or undesirable condition. For arteriosclerosis, a predetermined target may be, for example, apolipoprotein B on low density lipoprotein (LDL). For obesity, a predetermined marker or markers may be chosen from cell surface markers such as, for example, one of gastric inhibitory polypeptide receptor and CD36 antigen. Another undesirable predetermined target may be clotted blood. In another embodiment, the antibody may be targeted to a predetermined target associated with a reaction to an organ transplanted into the patient. The particular target and antibody may be specific to, but not limited to, the type of organ transplant. The antibody may have an affinity for a biological molecule associated with a reaction to an organ transplant. The antibody may have an affinity for a cell marker or markers associated with a reaction to an organ transplant. The marker or markers may be selected such that they represent a viable target on T cells or B cells of the immune system. In another embodiment, the antibody may be targeted to a predetermined target associated with a toxin in the patient. A toxin is defined as any poison produced by an organism including, but not limited to, bacterial toxins, plant toxins, insect toxin, animal toxins, and man-made toxins. The particular target and antibody may be specific to, but not limited to, the type of toxin. The antibody may have an affinity for the toxin or a biological molecule associated with a reaction to the toxin. The antibody may have an affinity for a cell marker or markers associated with a reaction to the toxin. In another embodiment, the antibody may be targeted to a predetermined target associated with a hormone-related disease. The particular target and antibody may be specific to, but not limited to, a particular hormone disease. The antibody may have an affinity for a hormone or a biological molecule associated with the hormone pathway. The antibody may have an affinity for a cell marker or markers associated with the hormone disease. In another embodiment, the antibody may be targeted to a predetermined target associated with non-cancerous diseased tissue. The particular target and antibody may be specific to, but not limited to, a particular non-cancerous diseased tissue, such as non-cancerous diseased deposits and precursor deposits. The antibody may have an affinity for a biological molecule associated with the non-cancerous diseased tissue. The antibody may have an affinity for a cell marker or markers associated with the non-cancerous diseased tissue. In another embodiment, the antibody may be targeted to a proteinaceous pathogen. The particular target and antibody may be specific to, but not limited to, a particular proteinaceous pathogen. The antibody may have an affinity for a proteinaceous pathogen or a biological molecule associated with the proteinaceous pathogen. The antibody may have an affinity for a cell marker or markers associated with the proteinaceous pathogen. For prion diseases, also known as transmissible spongiform encephalopathies, a predetermined target may be, for example, Prion protein 3F4.

See, e.g., U.S. Pat. Appl. Pub. No. 20050090732 (in particular Table I), incorporated herein by reference for a list of targets, cell-specific markers (e.g., antigens for targeting with an antibody moiety), antibodies, and indications associated with those targets, cell-specific markers, and antigens/antibodies.

In some embodiments, the technology finds use in imaging, such as for in situ hybridization (ISH). In some embodiments, the nucleotide analogs provided herein find use in nucleic acids that are hybridization probes for ISH and fluorescence in situ hybridization (FISH). In some embodiments, the nucleotide analogs find use in direct ISH and/or for immuno-histochemistry applications without using secondary detection reagents.

7. Pharmaceutical Formulations

In some embodiments, nucleotide analogs, oligonucleotides comprising a nucleotide analog, etc. are provided in a pharmaceutical formulation for administration to a subject. It is generally contemplated that the compounds (e.g., nucleotide analogs, oligonucleotides comprising a nucleotide analog, conjugates of nucleotide analogs and/or oligonucleotides comprising a nucleotide analog, etc.) related to the technology are formulated for administration to a mammal, and especially to a human with a condition that is responsive to the administration of such compounds. Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Accordingly, in some embodiments, the immunotherapeutic agent is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the compound over time.

In some embodiments, the compositions are formulated so that the active ingredient is embedded in a matrix of an insoluble substance (e.g., various acrylics, chitin) such that the dissolving compound finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the compound dissolves into the matrix and the matrix physically swells to form a gel, allowing the compound to exit through the gel's outer surface. In some embodiments, the formulations are in a micro-encapsulated form, e.g., which is used in some embodiments to produce a complex dissolution profile. For example, by coating the compound around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein in a pharmaceutical context means nano- or microparticles (or in some instances larger) that can consist in whole or in part of the compounds as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, nonerodible, biodegradable, or nonbiodegradable materials or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of the compounds or salts thereof to inhibit formation of degradation products. A solution is provided that contains the compound or salts thereof and at least one inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the compound is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the compound is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the compound is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compound is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the compound is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the compound is formulated with a humectant to provide a pleasant mouth-feel in oral applications. Humectants known in the art include cholesterol, fatty acids, glycerin, lauric acid, magnesium stearate, pentaerythritol, and propylene glycol. In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

8. Administration, Treatments, and Dosing

In some embodiments, the technology relates to methods of providing a dosage of a nucleotide analog, oligonucleotide comprising a nucleotide analog, or a conjugate thereof (e.g., comprising a targeting moiety, contrast agent, label, tag, etc.) to a subject. In some embodiments, a compound, a derivative thereof, or a pharmaceutically acceptable salt thereof, is administered in a pharmaceutically effective amount. In some embodiments, a compound, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of the compound or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, the compound, a derivative thereof, or a pharmaceutically acceptable salt thereof, is administered orally.

In some embodiments, a single dose of a compound or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The technology also relates to methods of treating a subject with a drug appropriate for the subject's malady. According to another aspect of the technology, a method is provided for treating a subject in need of such treatment with an effective amount of a compound or a salt thereof. The method involves administering to the subject an effective amount of a compound or a salt thereof in any one of the pharmaceutical preparations described above, detailed herein, and/or set forth in the claims. The subject can be any subject in need of such treatment. In the foregoing description, the technology is in connection with a compound or salts thereof. Such salts include, but are not limited to, bromide salts, chloride salts, iodide salts, carbonate salts, and sulfate salts. It should be understood, however, that the compound is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "compound" appears.

In some embodiments, a subject is tested to assess the presence, the absence, or the level of a malady and/or a condition. Such testing is performed, e.g., by assaying or measuring a biomarker, a metabolite, a physical symptom, an indication, etc., to determine the risk of or the presence of the malady or condition. In some embodiments, the subject is treated with a compound based on the outcome of the test. In some embodiments, a subject is treated, a sample is obtained and the level of detectable agent is measured, and then the subject is treated again based on the level of detectable agent that was measured. In some embodiments, a subject is treated, a sample is obtained and the level of detectable agent is measured, the subject is treated again based on the level of detectable agent that was measured, and then another sample is obtained and the level of detectable agent is measured. In some embodiments, other tests (e.g., not based on measuring the level of detectable agent) are also used at various stages, e.g., before the initial treatment as a guide for the initial dose. In some embodiments, a subsequent treatment is adjusted based on a test result, e.g., the dosage amount, dosage schedule, identity of the drug, etc. is changed. In some embodiments, a patient is tested, treated, and then tested again to monitor the response to therapy and/or change the therapy. In some embodiments, cycles of testing and treatment may occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/ test/treat, test/treat/test/treat/test, test/treat/test/test/treat/ treat/treat/test, treat/treat/test/treat, test/treat/treat/test/treat/ treat, etc.

Although the disclosure herein refers to certain illustrated embodiments, it is to be understood that these embodiments are presented by way of example and not by way of limitation.

EXAMPLES

Example 1—Characterization of Nucleotide Analogs

During the development of embodiments of the technology provided herein, nucleotide analogs were characterized by analytical chemical methods. In particular, 3'-O-propargyl-dATP, 3'-O-propargyl-dCTP, 3'-O-propargyl-dGTP, and 3'-O-propargyl-dTTP were synthesized according to the synthetic schemes described herein and characterized by $^1$H NMR, $^{31}$P NMR, anion exchange HPLC, and high-resolution mass spectrometry. The analytical testing indicated that the synthesis and purification were successful (Figures X-Y).

Example 2—Assays for Identifying Compatible Polymerases

In some embodiments, the technology is related to the incorporation of nucleotide analogs into a nucleic acid. Accordingly, the technology provides assays for identifying polymerases that recognize nucleotide analogs (e.g., 3'-O-propargyl-dNTP) as substrates.

For example, in some exemplary assays and/or embodiments, compatible polymerases are identified by a polymerase extension reaction (e.g., a single base extension reaction). See, e.g., Ausebel et al. (eds.), Current Protocols in Molecular Biology. New York: John Wiley & Sons, Inc; Sambrook et al. (1989). Molecular Cloning: A Laboratory Manual. (2nd ed.). Cold Spring Harbor: Cold Spring Harbor Laboratory Press.

For example, identifying compatible polymerases comprises providing a polymerase to test and a reaction buffer appropriate for the polymerase. For polymerases obtained from a commercial supplier (e.g., New England BioLabs, United States Biologicals, Promega, Invitrogen, Worthington, Sigma-Aldrich, Fluka, Finnzymes, Roche, 5 Prime, Qiagen, KAPA Biosystems, Thermo Scientific, Agilent, Life Technologies, etc.), the polymerase is often supplied with an appropriate reaction buffer. An exemplary reaction buffer comprises, e.g., a compatible buffer (e.g., 20 mM Tris-HCl), a salt (e.g., 10 mM KCl), a source of magnesium or manganese (e.g., 2 mM MgSO$_4$; 2 mM MnCl$_2$, etc.), a detergent (e.g., 0.1% TRITON X-100) and has a suitable pH (e.g., approximately pH 8.8 at approximately 25° C.). The activities of some polymerases are improved in the presence of other compounds, such as sulfate and other salts (e.g., 10 mM (NH$_4$)$_2$SO$_4$). Reaction mixtures for polymerase extension reactions are typically tested using Mg$^{2+}$ or Mn$^{2+}$ as the enzyme cofactor.

Polymerases are tested by providing in the reaction mixture a DNA template, a DNA primer that is complementary to the DNA template, and one or more nucleotides and/or nucleotide analogs. Typical concentrations of template and primer are approximately from 1 to 100 nM and typical concentrations of nucleotides and/or nucleotide analogs are approximately from 1 to 125 µM (e.g., 1 to 125 µM for each nucleotide and/or nucleotide analog and/or 1 to 500 µM total concentration of all nucleotides and/or nucleotide analogs). Templates and primers are synthesized by methods known in the art (e.g., using solid supports and phosphoramidite chemistry) and are available from several commercial suppliers (e.g., Integrated DNA Technologies, Coralville, Iowa).

A pre-annealed primer/template is typically produced for testing polymerases. For example, the primer is typically resuspended in a suitable buffer (e.g., Tris-EDTA, pH 8.0) at a suitable concentration, e.g., at 1 to 500 µM (e.g., at 100 µM) and the template is typically resuspended in a suitable buffer (e.g., Tris-EDTA, pH 8.0) at a suitable concentration, e.g., at 1 to 500 µM (e.g., at 100 µM). Then, a pre-annealed primer/template is produced by mixing approximately equal amounts of the primer and template in an annealing buffer. For example, a pre-annealed primer/template is produced by mixing approximately 100 µl of the approximately 1 to 500 µM (e.g., at 100 µM) primer solution to approximately 100 µl of the approximately 1 to 500 µM (e.g., at 100 µM) template solution in approximately 800 µl of an annealing buffer (e.g., 200 mM Tris, 100 mM potassium chloride, and 0.1 mM EDTA, pH 8.45) to provide a milliliter of primer/template solution. One of skill in the art can scale the volumes and concentrations as appropriate for the concentrations and volumes that are appropriate for the particular analysis. Then, an aliquot (e.g., 100 µl) of the primer/template solution is heated to denature intramolecular and/or intermolecular secondary structures (e.g., by heating at approximately 85° C. to 97° C. (e.g., at approximately 95° C.), e.g., for 1 to 5 minutes (e.g., 2 minutes). Next, the aliquot is cooled to an annealing temperature (e.g., 20° C. to 60° C. (e.g., 25° C.) and incubated for 1 to 10 minutes (e.g., for approximately 5 minutes) to allow the primer and template to anneal to form a primer/template. The primer/template can be diluted in an appropriate substrate dilution buffer (e.g., 20 mM Tris, 10 mM potassium chloride, and 0.01 mM EDTA, pH 8.45; e.g., a 1 to 10 dilution of the annealing buffer described above) for storage. For example, the primer/template can be diluted to a final concentration of 0.01 µM (e.g., to provide a 10× stock) in the substrate dilution buffer, aliquoted, and stored at −20° C.

Software packages are known in the art that provide assistance in designing templates and primers for these assays. In addition, several equations are available for calculating denaturation (e.g., melting ($T_m$) temperatures) and annealing temperatures. Standard references describe a simple estimate of the $T_m$ value that may be calculated by the equation: $T_m=81.5+0.41*(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi and SantaLucia, Biochemistry 36: 10581-94 (1997) include more sophisticated computations that account for structural, environmental, and sequence characteristics.

The primer and template or pre-annealed template is/are used to test the polymerase. For example, primer extension assays are conducted with 1 to 100 nM (e.g., 50 nM) of the primer/template, dNTPs (e.g., a mixture of 1 to 125 µM of each dATP, dCTP, dGTP, dTTP, modified dATP (e.g., 3'-O-propargyl-dATP), modified dCTP (e.g., 3'-O-propargyl-dCTP), modified dGTP (e.g., 3'-O-propargyl-dGTP), and/or modified dTTP (e.g., 3'-O-propargyl-dTTP)), and polymerase (e.g., 1 to 100 U of thermostable/thermophilic polymerase or mesophilic polymerase) in a final volume of approximately 1 to 100 µl (e.g., 10 to 20 µl) containing an appropriate buffer (e.g., as provided by the commercial supplier of the polymerase or the exemplary reaction buffer as described above). In some assays, the reaction mixture comprises 1 to 50 U (e.g., 1 U) of thermostable pyrophosphatase.

In some assays, a mixture of dNTPs and modified dNTPs is used. For example, some assays test the incorporation of a single base into a nucleic acid (e.g., in a single base extension assay). In such an assay, the primer hybridizes to a complementary region in the template to form a duplex such that the primer's terminal 3' end is directly adjacent to the base pairing partner of the nucleotide analog to be tested. In a successful test, the candidate polymerase being tested incorporates a single nucleotide analog at the 3' end of the primer. Many approaches are available for detecting the incorporation of the nucleotide analog, including fluorescence labeling, mass labeling for mass spectrometry, measuring enzyme activity using a protein moiety, and isotope labeling.

In particular, the assay tests the incorporation of a modified nucleotide (e.g., 3'-O-propargyl-dNTP) to the 3' end of the primer as directed by the template. In such an assay, the reaction mixture can contain three dNTPs and the one particular modified dNTP that is added to the 3' end of the primer as directed by the template. Some assays comprise the use of four individual reaction mixtures comprising each of the four primers annealed to a template (e.g., four primer/templates) designed such that each of the four modified nucleotides is to be added to the 3' end of the primer as directed by the template. For example, in some embodiments a primer/template is provided to test incorporation of a modified dATP (e.g., 3'-O-propargyl-dATP):

in which N is any nucleotide and "I" indicates complementary base pairing between the exemplary primer (top strand) and exemplary template (bottom strand). In some embodiments a primer/template is provided to test incorporation of a modified dCTP (e.g., 3'-O-propargyl-dCTP):

in which N is any nucleotide and "I" indicates complementary base pairing between the exemplary primer (top strand) and exemplary template (bottom strand). In some embodiments a primer/template is provided to test incorporation of a modified dGTP (e.g., 3'-O-propargyl-dGTP):

in which N is any nucleotide and "I" indicates complementary base pairing between the exemplary primer (top strand) and exemplary template (bottom strand). In some embodiments a primer/template is provided to test incorporation of a modified dTTP (e.g., 3'-O-propargyl-dTTP):

in which N is any nucleotide and "I" indicates complementary base pairing between the exemplary primer (top strand)

and exemplary template (bottom strand). The primers and templates can be any appropriate length for the assay and the position of the single-base extension can be directed by any appropriate nucleotide of the template, usually within the central portion of the template.

The polymerase is tested in the reaction mixture at a temperature appropriate for the polymerase. For example, a mesophilic polymerase is tested at a temperature of from 20° C. to 60° C. and a thermophilic polymerase is tested at a temperature from 80° C. to 97° C. or more (e.g., 100° C. or more). Appropriate temperatures are indicated by the literature accompanying commercially supplied polymerases; appropriate temperatures for other (e.g., any) polymerase can be determined by one of skill in the art by testing polymerase activity with standard nucleotides over a range of temperatures.

(Agilent), PfuUltra II Fusion HS DNA polymerase (Agilent), Phire HS II DNA polymerase (Thermo Scientific), M-MuLV Reverse Transcriptase (NEB), rTth DNA polymerase, 9∘N DNA Polymerase (NEB), THERMINATOR I DNA Polymerase (NEB), THERMINATOR II DNA polymerase (NEB), and 5 additional custom, non-catalog polymerases from NEB. Reaction conditions recommended by the commercial suppliers were followed for all polymerases tested. Tests of each polymerase were performed using both $Mg^{2+}$ and $Mn^{2+}$ as the co-factor in the reaction mixture.

The data collected indicated that the polymerases derived from *Thermococcus* sp. (e.g., *Thermococcus* sp. 9∘N (e.g., THERMINATOR I and THERMINATOR II)) incorporated the 3'-O-propargyl dNTPs provided herein into a nucleic acid (Table 1).

TABLE 1

| | Summary of polymerase screening | | | | | | | | |
|---|---|---|---|---|---|---|---|---|---|
| co-factor | Amplitaq Gold | KAPA HiFi | KAPA 2G | Herculase II Fusion | PfuUltra II Fusion | Phire HS II | M-MuLV | rTth | 9° N |
| $Mg^{2+}$ | − | − | − | − | − | − | − | − | − |
| $Mn^{2+}$ | − | − | − | − | − | − | − | − | + |

| co-factor | Therminator I | Therminator II | NEB 1 | NEB 2 | NEB 3 | NEB 4 | NEB 5 |
|---|---|---|---|---|---|---|---|
| $Mg^{2+}$ | − | + | − | − | − | − | − |
| $Mn^{2+}$ | − | +++ | − | − | − | − | − |

In some assays, the temperature is cycled between a temperature to denature nucleic acids (e.g., a melting temperature) of approximately 85° C. to 97° C. (e.g., at approximately 95° C.) for 1 to 5 minutes (e.g., 2 minutes), an annealing temperature of approximately 40° C. to 70° C. (e.g., at 55° C.) for 5 to 60 seconds (e.g., 15 to 20 seconds), and an extension temperature of approximately 60 to 75° C. (e.g., 70 to 75° C.) for 15 to 60 seconds (e.g., 20 to 45 seconds), e.g., for 20 to 50 cycles.

Successful incorporation of a modified nucleotide (e.g., a 3'-O-propargyl dNTP) is determined by any number of methods. In some particular assays, the size of the reaction product is quantified to determine if the modified nucleotide (e.g., a 3'-O-propargyl dNTP) was added to the primer. In particular, the product of a successful incorporation is one base pair longer than the known length of the primer. The primer can be assayed as a negative control sample for comparison. Also, a synthetic positive control oligonucleotide having the length and structure of a reaction product expected from a successful incorporation can be assessed. Any method of discriminating between nucleic acids that differ by one base is appropriate for the assay, e.g., gel electrophoresis (e.g., Agilent Bioanalyzer), mass spectrometry, HPLC, etc.

Example 3—Polymerase Screening

During the development of embodiments of the technology provided herein, experiments were conducted to identify polymerases that can efficiently incorporate 3'-O-propargyl-dNTP as substrates. In particular, embodiments of the exemplary nucleotide extension assays described in Example 2 were used to test multiple polymerase enzymes including those sold under the trade names Ampli-Taq (Life Technologies), KAPA HiFi (KAPA Biosystems), KAPA 2G (KAPA Biosystems), Herculase II Fusion DNA polymerase In Table 1, a minus ("−") indicates that the polymerase did not produce a detectable product incorporating the 3'-O-propargyl dNTP, a single plus ("+") indicates that the polymerase produced a detectable product incorporating the 3'-O-propargyl dNTP, and three plusses ("+++") indicates that the polymerase produced a substantial amount of 3'-O-propargyl dNTP incorporation product. NEB1, NEB2, NEB3, NEB4, and NEB5 indicate each of the five non-commercial New England BioLabs polymerases tested.

It is to be understood that assays (e.g., as described herein, as described elsewhere, and as are known in the art) are available to identify any polymerases that incorporate modified nucleotides (e.g., the 3'-O-propargyl dNTPs provided herein) into a nucleic acid. Accordingly, the technology is not limited by the use of the *Thermococcus* sp. 9∘N (THERMINATOR I and THERMINATOR II) polymerases and contemplates the use of any appropriate extant or yet to be discovered polymerase that incorporates the modified nucleotides (e.g., the 3'-O-propargyl dNTPs provided herein) into a nucleic acid. Experiments described herein using the *Thermococcus* sp. 9∘N (THERMINATOR II) polymerases are exemplary and do not limit the technology to the use of any particular polymerase.

Example 4—Incorporation of 3'-O-Propargyl-dNTP into a Nucleic Acid

During the development of embodiments of the technology provided herein, experiments were conducted to assess the incorporation of 3'-O-propargyl-dNTPs into a nucleic acid by a polymerase. In particular, experiments were conducted to evaluate the accurate incorporation of 3'-O-propargyl-dNTPs into a nucleic acid and to evaluate the terminating activity of the 3'-O-propargyl-dNTPs. To assess these characteristics of the nucleotide analogs provided herein, polymerase extension assays were conducted using a template nucleic acid having a sequence from human KRAS (e.g., KRAS exon 2 and flanking intron sequences) and a complementary primer (Table 2).

TABLE 2 template & primer sequences used to test incorporation of 3'-O-propargyl-dNTP

| Name | Sequence (5' to 3') | length (bases) | SEQ ID NO: |
|---|---|---|---|
| KRAS template | TTATTATAAGGCCTGCTGAAAATGACTGAA TATAAACTTGTGGTAGTTGGAGCTGGTGGC GTAGGCAAGAGTGCCTTGACGATACAGCTA ATTCAGAATCATTTTGTGGACGAATATGAT CCAACAATAGAGGTAAATCTTGTTTTAATA TGCATATTACTGGTGCAGGACCATTCT | 177 | 1 |
| R_ke2_trP1_T_bio | bTAAUCCTCTCTATGGGCAGTCGGTGATAG AATGGTCCTGCACCAGTAA | 48 | 2 |
| R_ke2_trP1_A_bio | bTAAUCCTCTCTATGGGCAGTCGGTGATAG AATGGTCCTGCACCAGTAAT | 49 | 3 |
| R_ke2_trP1_G_bio | bTAAUCCTCTCTATGGGCAGTCGGTGATAG AATGGTCCTGCACCAGTAATAT | 51 | 4 |
| R_ke2_trP1_C_bio | bTAAUCCTCTCTATGGGCAGTCGGTGATAG AATGGTCCTGCACCAGTAATATG | 52 | 5 |

In Table 2, a "b" indicates a biotin modification and a "U" indicates a deoxyuridine modification. Incorporation of the primers into extension products produces extension products comprising a uracil. The uracil is useful, e.g., for cleavage of the product (e.g., using uracil cleavage reagents) in a number of molecular biological manipulations (e.g., cleaving the product from a solid support).

To test incorporation of a 3'-O-propargyl-dTTP into a nucleic acid, a polymerase extension reaction mix was assembled comprising 20 mM Tris-HCl, 10 mM (NH$_4$)SO$_4$, 10 mM KCl, 2 mM MnCl$_2$, 0.1% Triton X-100, 200 μmol 3'-O-propargyl-dTTP, 6.25 μmol of primer R_ke2_trP1_T_bio (SEQ ID NO: 2), and 2 units of Therminator II DNA polymerase (New England BioLabs) in a 25-μl final reaction volume. A volume of 0.5 μmol of the KRAS template (SEQ ID NO: 1) was used as template (Table 2). The polymerase extension reaction was performed using a temperature cycling profile comprising exposing the reaction to a temperature of 95° C. for 2 minutes followed by 35 cycles of 95° C. for 15 seconds, 55° C. for 25 seconds, and 65° C. for 35 seconds.

After the polymerase extension reaction, 1 μl of the reaction mix was used directly for nucleic acid size analysis by gel electrophoresis (e.g., using an Agilent 2100 Bioanalyzer and High Sensitivity DNA Assay Chip). Data collected from size analysis showed the presence of a population of nucleic acids having a length corresponding to the length of the primer used in the reaction (e.g., 48 bases) and a population of nucleic acids having a length corresponding to the length of the primer plus one base (e.g., 49 bases). Accordingly, the data collected indicated the successful incorporation of the 3'-O-propargyl-dTTP at the 3' end of the primer. Further, the amounts of the two populations of nucleic acids were approximately equal, thus indicating the robust incorporation of the 3'-O-propargyl-dTTP at the 3' end of the primer to form the extension product.

Additional polymerase extension experiments were performed using the reaction conditions described above and replacing the 3'-O-propargyl-dTTP and the primer R_ke2_trP1_T_bio with 3'-O-propargyl-dATP and the primer R_ke2_trP1_A bio (SEQ ID NO: 3); 3'-O-propargyl-dCTP and the primer R_ke2_trP1_C bio (SEQ ID NO: 5); and 3'-O-propargyl dGTP and the primer R_ke2_trP1_G bio (SEQ ID NO: 4). The data collected from these experiments similarly indicated the successful incorporation of 3'-O-propargyl-dATP, 3'-O-propargyl-dCTP, and 3'-O-propargyl-dGTP, respectively, at the 3' end of the primers.

Example 5—Ladder Fragment Generation

During the development of embodiments of the technology provided herein, experiments were conducted to assess using the nucleotide analogs of the present technology to generate nucleic acid fragments that terminate at base-specific positions. In particular, reaction mixtures were produced and tested that included both natural dNTPs and each of the 3'-O-propargyl-dNTPs individually.

To test the fragment generation by 3'-O-propargyl-dTTP, a DNA fragment generation reaction mix was prepared comprising 20 mM Tris-HCl, 10 mM (NH$_4$)SO$_4$, 10 mM KCl, 2 mM MnCl$_2$, 0.1% Triton X-100, 1000 μmol dATP, 1000 μmol dCTP, 1000 μmol dGTP, 1000 μmol dTTP, 200 μmol 3'-O-propargyl-dTTP, 6.25 μmol of primer R_ke2_trP1_T_bio (SEQ ID NO: 2), and 2 units of THERMINATOR II DNA polymerase (New England BioLabs) in a 25-μl final reaction volume. A volume of 0.5 μmol of the KRAS template (SEQ ID NO: 1) was used as template. The polymerase extension reaction was performed using a temperature cycling profile comprising exposing the reaction to a temperature of 95° C. for 2 minutes followed by 50 cycles of 95° C. for 15 seconds, 55° C. for 25 seconds, and 65° C. for 35 seconds.

After the polymerase extension reaction, 1 μl of the reaction mix was used directly for nucleic acid size analysis by gel electrophoresis (e.g., using an Agilent 2100 Bioanalyzer and High Sensitivity DNA Assay Chip). Data collected from size analysis showed that the reaction generated a population of nucleic acid fragments having a range of sizes corresponding to the expected lengths of nucleic acids that are complementary to the template and terminated by 3'-O-propargyl-dT at each position where termination is expected.

Additional polymerase extension experiments were performed using the reaction conditions described above and replacing the 3'-O-propargyl-dTTP with 3'-O-propargyl-dATP, 3'-O-propargyl-dCTP, or 3'-O-propargyl dGTP. The data collected from these experiments similarly indicated that the reactions generated populations of nucleic acid fragments having a range of sizes corresponding to the expected lengths of nucleic acids that are complementary to the template and terminated by 3'-O-propargyl-dA, 3'-O-propargyl-dC, or 3'-O-propargyl-dG at each position where termination is expected.

Example 6—Synthesis of 5'-Azido-Methyl-Modified Oligonucleotide

During the development of embodiments of the technology provided herein, an oligonucleotide comprising a 5'-azido-methyl modification was synthesized and characterized. Synthesis of the modified oligonucleotide was performed using phosphoramidite chemical synthesis. In the last synthetic step, phosphoramidite chemical synthesis was used to incorporate a 5'-iodo-dT phosphoramidite at the terminal 5' position. The oligonucleotide attached to the solid support in the reaction column was then treated as follows.

First, sodium azide (30 mg) was resuspended in dry DMF (1 ml), heated for 3 hours at 55° C., and cooled to room temperature. The supernatant was taken up with a 1-ml syringe and passed back and forth through the reaction column comprising the 5'-iodo-modified oligonucleotide and incubated overnight at ambient (room) temperature. After incubation, the column was washed with dry DMF, washed with acetonitrile, and then dried via argon gas. The resulting 5'-azido-methyl-modified oligonucleotide was cleaved from the solid support and deprotected by heating in aqueous ammonia for 5 hours at 55° C. The final product was an oligonucleotide having the sequence shown below:

```
                                         (SEQ ID NO: 6)
Az-TCTGAGTCGGAGACACGCAGGGATGAGATGGT
```

The "Az" indicates the azido-methyl modification at the 5' end (e.g., 5'-azido-methyl modification), e.g., to provide an oligonucleotide having a structure according to:

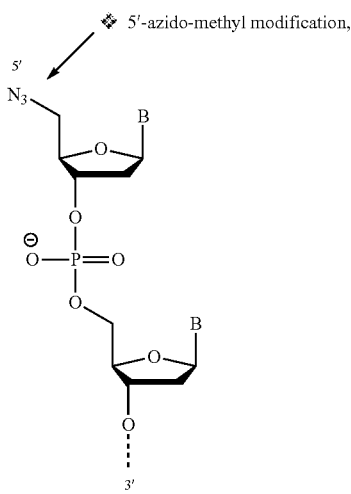

where B is the base of the nucleotide (e.g., adenine, guanine, thymine, cytosine, or a natural or synthetic nucleobase, e.g., a modified purine such as hypoxanthine, xanthine, 7-methylguanine; a modified pyrimidine such as 5,6-dihydrouracil, 5-methylcytosine, 5-hydroxymethylcytosine; etc.).

Example 7—Conjugation of 5'-Azido-Methyl-Modified Oligonucleotide and 3'-O-Propargyl-Modified Nucleic Acid Fragments During the development of embodiments of the technology provided herein, experiments were conducted to test the conjugation of a 5'-azido-methyl-modified oligonucleotide (e.g., see Example 6) to 3'-O-propargyl-modified nucleic acid fragments (e.g., see Example 5) by click chemistry. In particular, experiments were conducted in which a 5'-azido-methyl-modified oligonucleotide was chemically conjugated to 3'-O-propargyl-modified DNA fragments using copper (I) catalyzed 1,3-dipolar alkyne-azide cycloaddition chemistry ("click chemistry").

Click chemistry was performed using commercially available reagents (baseclick GmbH, Oligo-Click-M Reload kit) according to the manufacturer's instructions. Briefly, approximately 0.1 µmol of 3'-O-propargyl-modified DNA fragments comprising a 5'-biotin modification were reacted with approximately 500 µmol of 5'-azido-methyl-modified oligonucleotide (see, e.g., Example 6, e.g., SEQ ID NO: 6) using the click chemistry reagent in a total volume of 10 µl. The reaction mixture was incubated at 45° C. for 30 minutes. Following the incubation, the supernatant was transferred to a new microcentrifuge tube and a 40-µl volume of the commercially supplied binding and wash buffer (e.g., 1 M NaCl, 10 mM Tris-HCl, 1 mM EDTA, pH 7.5) was added. The conjugated reaction product was isolated from the excess 5'-azido-methyl-modified oligonucleotide by incubating the click chemistry reaction mixture with streptavidin-coated magnetic beads (Dynabeads, MyOne Streptavidin C1, Life Technologies) at ambient (room) temperature for 15 minutes. The beads were separated from the supernatant using a magnet and the supernatant was removed. Subsequently, the beads were washed twice using the binding and wash buffer and then resuspended in 25 µl of TE buffer (10 mM Tris-HCl, 0.1 mM EDTA, pH approximately 8).

The product was cleaved from the solid support (bead) using uracil cleavage (Uracil Glycosylase and Endonuclease VIII, Enzymatics). In particular, uracil cleavage reagents were used to cleave the reaction products at the site of the deoxyuridine modification located near the 5'-terminal location of the conjugated product (see SEQ ID NOs: 2-5). Finally, the supernatant comprising the conjugated product was purified using Ampure XP (Beckman Coulter) following the manufacturer's protocol and eluted in 20 µl of TE buffer.

Example 8—Amplification of Conjugated Product

During the development of embodiments of the technology described herein, experiments were performed to characterize the chemical conjugation of the 5'-azido-methyl-modified oligonucleotide to the 3'-O-propargyl modified nucleic acid fragments and to evaluate the triazole linkage as a mimic of a natural phosphodiester bond in a nucleic acid backbone. To test the ability of a polymerase to recognize the conjugated product as a template and traverse the triazole linkage during synthesis, PCR primers were designed to produce amplicons that span the triazole linkage of the conjugation products:

```
Primer 1
                                         SEQ ID NO: 7
CCTCTCTATGGGCAGTCGGTGAT Primer 2
                                         SEQ ID NO: 8
CCATCTCATCCCTGCGTGTCTC
```

A commercially available PCR pre-mix (KAPA 2G HS, KAPA Biosystems) was used to provide a 25-µl reaction mixture comprising, in addition to components provided by the mix (e.g., buffer, polymerase, dNTPs), 0.25 µM Primer 1 (SEQ ID NO: 7), 0.25 µM of Primer 2 (SEQ ID NO: 8), and 2 µl of purified conjugated product (see Example 7) as template for amplification. The reaction mixture was thermally cycled by incubating the sample at 95° C. for 5 minutes, followed by 30 cycles of 98° C. for 20 seconds, 60° C. for 30 seconds, and 72° C. for 20 seconds. The amplification products were analyzed by gel electrophoresis (e.g., using an Agilent Bioanalyzer 2100 system and High-Sensitivity DNA Chip) to determine the size distributions of the reaction products.

Analysis of the amplification products indicated that the amplification reaction successfully produced amplicons using the conjugated products of the click chemistry reaction (see Example 7) as templates for amplification. In particular, analysis of the amplification products indicated that the polymerase processed along the template and through the triazole linkage to produce amplicons from the template. Further, the amplification produced a heterogeneous population of amplicons having a range of sizes corresponding to the expected sizes produced by amplification of the base-specific terminated DNA fragments via incorporation of the 3'-O-propargyl-dNTP. The fragment analysis also showed the proper fragment size increase corresponding to thirty one (31) additional bases from the conjugated 5'-azido-methyl-modified oligonucleotide.

Example 9—Ladder Generation Using 3'-O-Propargyl dNTP Termination

During the development of embodiments of the technology provided herein, experiments were conducted to assess the generation of terminated nucleic acid fragments in a reaction comprising a mixture of 3'-O-propargyl-dNTPs and natural (standard) dNTPs. In particular, experiments were conducted to assess the generation of fragments terminated at each position within the target region by incorporation of chain-terminating 3'-O-propargyl-dNTPs by DNA polymerase during synthesis.

Experiments were conducted using a mixture of natural dNTPs and all four of the 3'-O-propargyl-dNTPs in a single reaction. The DNA fragment generation reaction mix comprised 20 mM Tris-HCl, 10 mM (NH$_4$)SO$_4$, 10 mM KCl, 2 mM MnCl$_2$, 0.1% Triton X-100, 1000 µmol dATP, 1000 µmol dCTP, 1000 µmol dGTP, 1000 µmol dTTP, 100 µmol of 3'-O-propargyl-dATP, 100 µmol of 3'-O-propargyl-dCTP, 100 µmol of 3'-O-propargyl-dGTP, 100 µmol of 3'-O-propargyl-dTTP, 6.25 µmol of primer R_ke2_trP1_T_bio (SEQ ID NO: 2), and 2 units of Therminator II DNA polymerase (New England BioLabs) in a 25-µl reaction volume. 0.5 µmol of purified amplicon corresponding to a region in KRAS exon 2 (SEQ ID NO: 1) was used as template. The polymerase extension reaction was thermocycled by heating to 95° C. for 2 minutes, followed by 45 cycles at 95° C. for 15 seconds, 55° C. for 25 seconds, and 65° C. for 35 seconds.

After the polymerase extension reaction, 1 µl of the reaction mix was used directly for DNA fragment size analysis using gel electrophoresis (Agilent 2100 Bioanalyzer and High Sensitivity DNA Assay Chip). Fragment size analysis of the reaction products indicated that the fragment generation reaction successfully produced a ladder of nucleic acid fragments having the expected sizes.

Subsequently, a 5'-azido-methyl-modified oligonucleotide (see, e.g., Example 6, e.g., SEQ ID NO: 6) was chemically conjugated to the terminated DNA fragments comprising 3'-O-propargyl-dN using click chemistry as described in Example 6 and Example 7 above. After the conjugation, an amplification reaction was performed to amplify the conjugated products as described in Example 8. DNA fragment size analysis of the amplicons produced from the conjugated products showed the expected shift in size resulting from conjugation of the 5'-azido-modified oligonucleotide to the amplicons produced from the fragment ladder.

Example 10—Control of Fragment Size

During the development of embodiments of the technology provided herein, experiments were conducted to control the size distribution of terminated nucleic acid fragments produced in a reaction comprising a mixture of 3'-O-propargyl-dNTPs and natural (standard) dNTPs by adjusting the ratio of 3'-O-propargyl-dNTPs to natural (standard) dNTPs. It was contemplated that the molar ratio of 3'-O-propargyl-dNTPs and natural dNTPs affects the fragment size distribution due to competition between the 3'-O-propargyl-dNTPs (that terminate extension) and natural dNTPs (that elongate the polymerase product) for incorporation into the synthesized nucleic acid by the polymerase.

Accordingly, experiments were performed in which the products of fragment ladder generation reactions were assessed at various molar ratios of 3'-O-propargyl-dNTPs to natural dNTPs. Fragment ladder generation reactions were performed using 2:1, 10:1, and 100:1 molar ratios of natural dNTPs to 3'-O-propargyl-dNTPs. The fragment generation reaction mixtures used in these experiments comprised 20 mM Tris-HCl, 10 mM (NH$_4$)SO$_4$, 10 mM KCl, 2 mM MnCl$_2$, 0.1% Triton X-100, 1000 µmol dATP, 1000 µmol dCTP, 1000 µmol dGTP, 1000 µmol dTTP, 6.25 µmol of primer R_ke2_trP1_T_bio (SEQ ID NO: 2), 2 units of Therminator II DNA polymerase (New England BioLabs), and 0.5 µmol of purified amplicon corresponding to a region in KRAS exon 2 (SEQ ID NO: 1) as template in a 25-µl final reaction volume.

In addition, reactions testing a 2:1 ratio of natural dNTPs to 3'-O-propargyl-dNTPs comprised 500 µmol of 3'-O-propargyl-dATP, 500 µmol of 3'-O-propargyl-dCTP, 500 µmol of 3'-O-propargyl-dGTP, and 500 µmol of 3'-O-propargyl-dTTP. Reactions testing a 10:1 ratio of natural dNTPs to 3'-O-propargyl-dNTPs comprised 100 µmol of 3'-O-propargyl-dATP, 100 µmol of 3'-O-propargyl-dCTP, 100 µmol of 3'-O-propargyl-dGTP, and 100 µmol of 3'-O-propargyl-dTTP. Reactions testing a 100:1 ratio of natural dNTPs to 3'-O-propargyl-dNTPs comprised 10 µmol of 3'-O-propargyl-dATP, 10 µmol of 3'-O-propargyl-dCTP, 10 µmol of 3'-O-propargyl-dGTP, and 10 µmol of 3'-O-propargyl-dTTP The polymerase extension reactions were temperature cycled by incubating at 95° C. for 2 minutes, followed by 45 cycles at 95° C. for 15 seconds, 55° C. for 25 seconds, and 65° C. for 35 seconds. After the polymerase extension reaction, 5'-azido-methyl-modified oligonucleotides (see, e.g., Example 6, e.g., SEQ ID NO: 6) were chemically conjugated to the nucleic acid fragments terminated with 3'-O-propargyl-dN using click chemistry as described in Example 6 and Example 7. After the conjugation, the conjugation products were used as templates for amplification to produce amplicons corresponding to the conjugated products as described in Example 8. Fragment size analysis was performed on the conjugated products.

Fragment size analysis of the amplified conjugation products produced from the products of the three different molar ratio conditions indicated that the fragment size depended on the ratio of 3'-O-propargyl-dNTPs to natural dNTPs. Analysis of the fragment sizes shows a in fragment size distribution shift as a function of the molar ratios of dNTP to 3'-O-propargyl-dNTP. At the 2:1 molar ratio, larger populations of shorter fragments were detected compared to the other two molar ratio conditions. At the 10:1 molar ratio, a larger fraction of longer fragments was present relative to the 2:1 molar ratio. At the 100:1 molar ratio, the major population of fragments comprised longer DNA fragments relative to the other two molar ratios.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A kit, comprising:
   a) a primer;
   b) a nucleotide analog comprising an alkyne moiety comprising a carbon-carbon triple bond attached to a 3' sugar of said nucleotide analog; and
   c) a polymerase wherein said polymerase incorporates said nucleotide analog comprising an alkyne moiety comprising a carbon-carbon triple bond attached to a 3' sugar of said nucleotide analog into a nucleic acid.

2. The kit of claim 1, wherein said nucleotide analog is a 3'-O-propargyl-dNTP nucleotide analog and N is selected from the group consisting of A, C, G, T and U.

3. The kit of claim 1, further comprising a dNTP.

4. The kit of claim 1, further comprising a 5'-azide-modified DNA fragment.

5. The kit of claim 1, wherein said primer comprises an index or barcode.

6. The kit of claim 1, further comprising an adaptor oligonucleotide.

7. The kit of claim 6, wherein said adaptor oligonucleotide comprises an azide moiety.

8. The kit of claim 1, wherein said polymerase is a polymerase from a *Thermococcus* species 9° N-7 comprising a mutation selected from the group consisting of D141A, E143A, Y409V, and A485L.

9. The kit of claim 1, further comprising a click chemistry catalytic reagent.

10. The kit of claim 9, wherein said click chemistry catalytic reagent is a copper-based catalytic reagent.

11. The kit of claim 1, further comprising a ligase.

12. The kit of claim 1, further comprising a 5'-azido-methyl oligonucleotide.

13. The kit of claim 12, wherein said 5'-azido-methyl oligonucleotide comprises a barcode.

14. The kit of claim 1, further comprising one or more of a buffer, a salt, a reaction vessel, an instruction, a solid support and computer software.

15. The kit of claim 14, wherein said computer software is configured to extract nucleotide sequence data from data produced by a sequencer, to identify barcodes and target subsequences from said data produced by said sequencer, to align and/or assemble subsequences from said data produced by said sequencer to produce a consensus sequence, and/or to align subsequences and/or a consensus sequence to a reference sequence.

16. The kit of claim 1, further comprising one or more reagents for polymerase chain reaction (PCR) amplification.

17. The kit of claim 1, further comprising one or more reagents for isothermal amplification.

18. The kit of claim 1, further comprising one or more reagents for next generation sequencing (NGS).

19. A kit, comprising:
   a) a primer;
   b) a nucleotide analog comprising an alkyne moiety comprising a carbon-carbon triple bond attached to a 3' sugar of said nucleotide analog; and
   c) a polymerase wherein said polymerase incorporates said nucleotide analog comprising an alkyne moiety comprising a carbon-carbon triple bond attached to a 3' sugar of said nucleotide analog into a nucleic acid; and
   d) a negative control oligonucleotide wherein said negative control oligonucleotide is said primer.

20. A kit, comprising:
   a) a primer;
   b) a nucleotide analog comprising an alkyne moiety comprising a carbon-carbon triple bond attached to a 3' sugar of said nucleotide analog; and
   c) a polymerase wherein said polymerase incorporates said nucleotide analog comprising an alkyne moiety comprising a carbon-carbon triple bond attached to a 3' sugar of said nucleotide analog into a nucleic acid; and
   d) a positive control oligonucleotide wherein said positive control oligonucleotide is a synthetic positive control oligonucleotide having the length and structure of a reaction product expected from a successful incorporation.

* * * * *

```
                        SEQUENCE LISTING

<160> NUMBER OF SEQ ID NOS: 10

<210> SEQ ID NO 1
<211> LENGTH: 177
<212> TYPE: DNA
<213> ORGANISM: homo sapiens

<400> SEQUENCE: 1
ttattataag gcctgctgaa aatgactgaa tataaacttg tggtagttgg agctggtggc      60
gtaggcaaga gtgccttgac gatacagcta attcagaatc attttgtgga cgaatatgat     120
ccaacaatag aggtaaatct tgttttaata tgcatattac tggtgcagga ccattct        177

<210> SEQ ID NO 2
<211> LENGTH: 48
<212> TYPE: DNA
<213> ORGANISM: Artificial
<220> FEATURE:
<223> OTHER INFORMATION: Synthetic

<400> SEQUENCE: 2
taaucctctc tatgggcagt cggtgataga atggtcctgc accagtaa                  48

<210> SEQ ID NO 3
<211> LENGTH: 49
<212> TYPE: DNA
<213> ORGANISM: Artificial
<220> FEATURE:
<223> OTHER INFORMATION: Synthetic

<400> SEQUENCE: 3
taaucctctc tatgggcagt cggtgataga atggtcctgc accagtaat                 49

<210> SEQ ID NO 4
<211> LENGTH: 51
<212> TYPE: DNA
<213> ORGANISM: Artificial
<220> FEATURE:
<223> OTHER INFORMATION: Synthetic

<400> SEQUENCE: 4
taaucctctc tatgggcagt cggtgataga atggtcctgc accagtaata t              51

<210> SEQ ID NO 5
<211> LENGTH: 52
<212> TYPE: DNA
<213> ORGANISM: Artificial
<220> FEATURE:
<223> OTHER INFORMATION: Synthetic

<400> SEQUENCE: 5
taaucctctc tatgggcagt cggtgataga atggtcctgc accagtaata tg             52
```

<210> SEQ ID NO 6
<211> LENGTH: 32
<212> TYPE: DNA
<213> ORGANISM: Artificial
<220> FEATURE:
<223> OTHER INFORMATION: Synthetic

<400> SEQUENCE: 6
tctgagtcgg agacacgcag ggatgagatg gt                                       32

<210> SEQ ID NO 7
<211> LENGTH: 23
<212> TYPE: DNA
<213> ORGANISM: Artificial
<220> FEATURE:
<223> OTHER INFORMATION: Synthetic

<400> SEQUENCE: 7
cctctctatg ggcagtcggt gat                                                 23

<210> SEQ ID NO 8
<211> LENGTH: 22
<212> TYPE: DNA
<213> ORGANISM: Artificial
<220> FEATURE:
<223> OTHER INFORMATION: Synthetic

<400> SEQUENCE: 8
ccatctcatc cctgcgtgtc tc                                                  22

<210> SEQ ID NO 9
<211> LENGTH: 21
<212> TYPE: PRT
<213> ORGANISM: Artificial
<220> FEATURE:
<223> OTHER INFORMATION: Synthetic

<400> SEQUENCE: 9

Cys Trp Leu Ser Glu Ala Gly Pro Val Val Thr Val Arg Ala Leu Arg
1               5                   10                  15

Gly Thr Gly Ser Trp
            20

<210> SEQ ID NO 10
<211> LENGTH: 7
<212> TYPE: PRT
<213> ORGANISM: homo sapiens

<400> SEQUENCE: 10

Val His Ser Pro Asn Lys Lys
1               5